US011578358B2

(12) United States Patent
Hayden et al.

(10) Patent No.: US 11,578,358 B2
(45) Date of Patent: Feb. 14, 2023

(54) DEVICES AND METHODS FOR SAMPLE ANALYSIS

(71) Applicant: Abbott Laboratories, Abbott Park, IL (US)

(72) Inventors: Mark A. Hayden, Ingleside, IL (US); Jeffrey B. Huff, Lincolnshire, IL (US); Sophie Laurenson, Allschwil (CH); Andrew Fischer, Euless, TX (US); John Robinson, Gurnee, IL (US); Shelley R. Holets-McCormack, Waukegan, IL (US)

( * ) Notice: Subject to any disclaimer, the term of this patent is extended or adjusted under 35 U.S.C. 154(b) by 96 days.

(21) Appl. No.: 16/312,489

(22) PCT Filed: Sep. 14, 2017

(86) PCT No.: PCT/US2017/051627
§ 371 (c)(1),
(2) Date: Dec. 21, 2018

(87) PCT Pub. No.: WO2018/053174
PCT Pub. Date: Mar. 22, 2018

(65) Prior Publication Data
US 2019/0153524 A1     May 23, 2019

Related U.S. Application Data

(60) Provisional application No. 62/395,255, filed on Sep. 15, 2016.

(51) Int. Cl.
C12Q 1/6853     (2018.01)

(52) U.S. Cl.
CPC ................... C12Q 1/6853 (2013.01)

(58) Field of Classification Search
None
See application file for complete search history.

(56) References Cited

U.S. PATENT DOCUMENTS

| | | |
|---|---|---|
| 4,582,788 A | 4/1986 | Erlich |
| 5,234,809 A | 8/1993 | Boom et al. |
| 5,750,338 A | 5/1998 | Collins et al. |
| 5,780,224 A | 7/1998 | Collins |
| 6,110,678 A | 8/2000 | Weisburg et al. |
| 6,280,952 B1 | 8/2001 | Weisburg et al. |
| 6,294,326 B1 | 9/2001 | Carrino et al. |
| 6,410,278 B1 | 6/2002 | Notomi et al. |
| 6,534,273 B2 | 3/2003 | Weisburg et al. |
| 7,070,921 B2 | 7/2006 | Huang et al. |
| 7,270,981 B2 | 9/2007 | Armes et al. |
| 7,485,428 B2 | 2/2009 | Armes et al. |
| 7,517,969 B2 | 4/2009 | Reitan et al. |
| 8,017,340 B2 | 9/2011 | Collier et al. |
| 8,236,574 B2 | 8/2012 | Duffy et al. |
| 8,415,171 B2 | 4/2013 | Rissin et al. |
| 8,460,875 B2 | 6/2013 | Armes et al. |
| 9,051,601 B2 | 6/2015 | Becker et al. |
| 2006/0121544 A1 | 6/2006 | Boge et al. |
| 2009/0017453 A1 | 1/2009 | Maples et al. |
| 2011/0212462 A1* | 9/2011 | Duffy ..................... G01N 33/53 435/7.1 |
| 2011/0212846 A1 | 9/2011 | Spier |
| 2011/0212848 A1* | 9/2011 | Duffy ............... G01N 33/54313 506/9 |
| 2014/0194305 A1* | 7/2014 | Kayyem .............. C12Q 1/6825 506/18 |
| 2015/0167067 A1 | 6/2015 | Spier |

FOREIGN PATENT DOCUMENTS

| | | |
|---|---|---|
| CN | 102884431 A | 3/2011 |
| JP | 2009529883 A | 8/2009 |
| WO | WO2011100057 A2 | 8/2011 |
| WO | 2012070618 | 5/2012 |
| WO | 2014113502 A1 | 7/2014 |

OTHER PUBLICATIONS

Rodiger, Nucleic acid detection based on the use of microbeads: a review, Microchimica Acta, 181: 1151-1168, 2014. (Year: 2014).*
Boom, et al. (1990) "Rapid and Simple Method for Purification of Nucleic Acids" Journal of Clinical Microbiology 28(3): 495-503.
Chatterjee, et al. (2006) "Droplet-based microfluidics with nonaqueous solvents and solutions" Lab Chip 6: 199-206.
Collins and Mccarthy (2003) "Purification and characterization of Thermus thermophilus UvrD" Extremophiles 7: 35-41.
Dafforn, et al. (2004) "Linear mRNA amplification from as little as 5 ng total RNA for global gene expression analysis" BioTechniques 37(5): 854-857.
Dean, et al. (2002) "Comprehensive human genome amplification using multiple displacement amplification" PNAS 99(8): 5261-5266.
Grainge, et al. (2003) "Biochemical analysis of components of the pre-replication complex of Archaeoglobus fulgidus" Nucleic Acids Research 31(16): 4888-4898.
Jangam, et al. (2009) "Rapid, Point-of-Care Extraction of Human Immunodeficiency Virus Type 1 Proviral DNA from Whole Blood for Detection by Real-Time PCR" J Clin Microbiol 47(8): 2363-2368.

(Continued)

*Primary Examiner* — Angela M. Bertagna
*Assistant Examiner* — Carolyn L Greene
(74) *Attorney, Agent, or Firm* — Edward J. Baba; Mandar A. Joshi; Bozicevic, Field & Francis LLP

(57) ABSTRACT

Integrated devices that include a sample preparation component integrated with a detection component are disclosed. The sample preparation component may be a digital microfluidics module or a surface acoustic wave module which modules are used for combing a sample droplet with a reagent droplet and for performing additional sample preparation step leading to a droplet that contains beads/particles/labels that indicate presence or absence of an analyte of interest in the sample. The beads/particles/labels may be detected by moving the droplet to the detection component of the device, which detection component includes an array of wells. The detection modules disclosed here can be used for detecting analytes of interest which analytes may have been enriched by amplification, isolation, or other techniques.

33 Claims, 27 Drawing Sheets

(56) References Cited

OTHER PUBLICATIONS

Kaplan, et al. (1999) "DnaB from Thermus aquaticus Unwinds Forked Duplex DNA with an Asymmetric Tail Length Dependence" J Biol Chem 274(11): 6889-6897.

Kievits, et al. (1991) "NASBA™ isothermal enzymatic in vitro nucleic acid amplification optimized for the diagnosis of HIV-1 infection" Journal of Virological Methods 35: 273-286.

Liu, et al. (1996) "Rolling Circle DNA Synthesis: Small Circular Oligonucleotides as Efficient Templates for DNA Polymerases" J Am Chem Soc 118(7): 1587-1594.

Notomi, et al. (2000) "Loop-mediated isothermal amplification of DNA" Nucleic Acids Research 28(12): e63, 7 pages.

Piepenburg, et al. (2006) "DNA Detection Using Recombination Proteins" PLoS Biol 4(7)e204: 1115-1121.

Sur, et al. (2010) "Immiscible Phase Nucleic Acid Purification Eliminates PCR Inhibitors with a Single Pass of Paramagnetic Particles through a Hydrophobic Liquid" Journal of Molecular Diagnostics 12(5): 620-628.

Vincent, et al. (2004) "Helicase-dependent isothermal DNA amplification" EMBO Reports 5(8): 795-800.

Vuorinen, et al. (1995) "Direct Detection of *Mycobacterium tuberculosis* complex in respiratory Specimens by Gen-Probe Amplified *Mycobacterium tuberculosis* Direct Test and Roche Amplicor *Mycobacterium tuberculosis* Test" J Clin Microbiol 33(7): 1856-1859.

Walker, et al. (1992) "Strand displacement amplification—an isothermal, in vitro DNA amplification technique" Nucleic Acids Research 20(7): 1691-1696.

Wang, et al. (2004) "DNA amplification method tolerant to sample degradation" Genome Res 14: 2357-2366.

Wu, et al. (1989) "The ligation amplification reaction (LAR)—Amplification of specific DNA sequences using sequential rounds of template-dependent ligation" Genomics 4(4): 560-569.

Cohen, Limor, et al., "Digital direct detection of microRNAs using single molecule arrays", Nucleic Acids Research 45 (14), 2017, e137, 9 pages.

Guan, Weihua, et al., "Droplet Digital Enzyme-Linked Oligonucleotide Hybridization Assay for Absolute RNA Quantification", Scientific Reports 5(1), 2015, 1-9.

Lagerstrom, Maria, et al., "Capture PC: Efficient Amplification of DNA Fragments Adjacent to a Known Sequence in Human and YAC DNA", Genome Res 1, 1991, 111-119.

Li, Zhaohui, et al., "Detection of Single-Molecule DNA Hybridization Using Enzymatic Amplification in an Array of Femtoliter-Sized Reaction Vessels", J. Am. Chem. Soc. 130, 2008, 12622-12623.

Song, Linan, et al., "Direct Detection of Bacterial Genomic DNA at Sub-Femtomolar Concentrations Using Single Molecule Arrays", Analytical Chemistry 85, 2013, 1932-1939.

Wilde, J T, et al., "A novel ELISA-based primer extension assay for the detection of the factor V Leiden mutation", British Journal of Haematology 106, 1999, 427-430.

\* cited by examiner

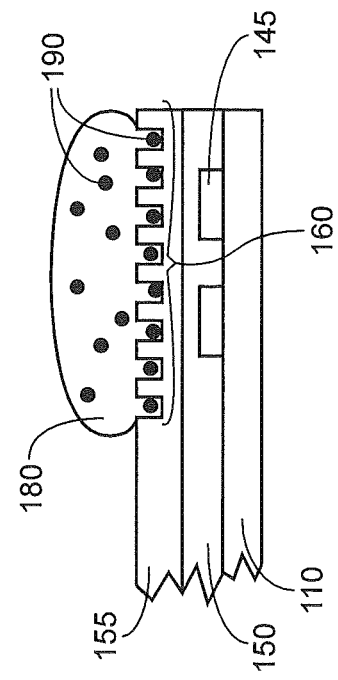
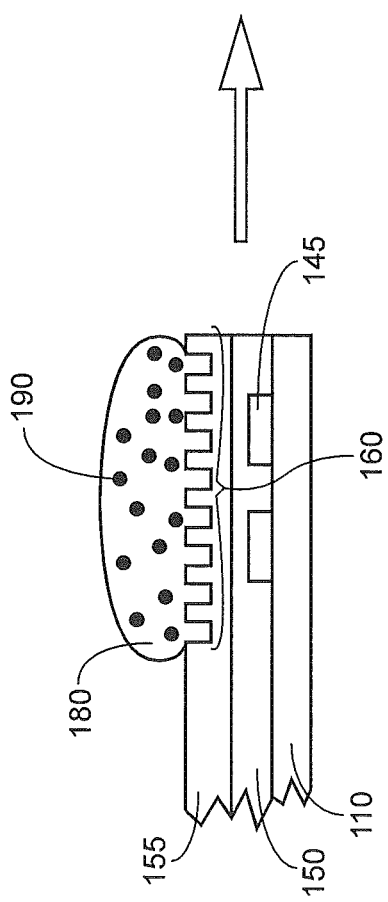
FIG. 4A
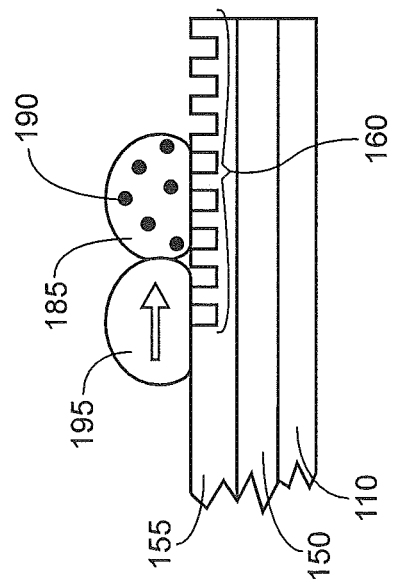
FIG. 4B

| Threshold Copy Number for Detection (using digital IA format) for 150 µl rxn | Number of Cycles | Fold Amplification | Actual Numbers of Molecules (theoretical) per RXN | Threshold Copy Number for Detection (using analog IA format), assumes a 150 µl sample |
|---|---|---|---|---|
| Not detectible | 0 | 1 | 8 | Not detectible |
| Not detectible | 1 | 2 | 15 | Not detectible |
| Not detectible | 2 | 4 | 30 | Not detectible |
| Not detectible | 3 | 8 | 60 | Not detectible |
| Not detectible | 4 | 16 | 120 | Not detectible |
| Not detectible | 5 | 32 | 240 | Not detectible |
| Not detectible | 6 | 64 | 480 | Not detectible |
| Not detectible | 7 | 128 | 960 | Not detectible |
| Not detectible | 8 | 256 | 1,920 | Not detectible |
| Not detectible | 9 | 512 | 3,840 | Not detectible |
| >6,000 | 10 | 1,024 | 7,680 | Not detectible |
| >6,000 | 11 | 2,048 | 15,360 | Not detectible |
| >6,000 | 12 | 4,096 | 30,720 | Not detectible |
| >6,000 | 13 | 8,192 | 61,440 | Not detectible |
| >6,000 | 14 | 15,384 | 122,880 | Not detectible |
| >6,000 | 15 | 32,768 | 245,760 | Not detectible |
| >6,000 | 16 | 65,536 | 491,520 | Not detectible |
| >6,000 | 17 | 131,072 | 983,040 | Not detectible |
| >6,000 | 18 | 262,144 | 1,966,080 | Not detectible |
| >6,000 | 19 | 524,288 | 3,932,160 | Not detectible |
| >6,000 | 20 | 1,048,576 | 7,864,320 | Not detectible |
| >6,000 | 21 | 2,097,152 | 15,728,640 | Not detectible |
| >6,000 | 22 | 4,194,304 | 31,457,280 | Not detectible |
| >6,000 | 23 | 8,388,608 | 62,914,560 | Not detectible |
| >6,000 | 24 | 16,777,216 | 125,829,120 | >90,000,000 |
| >6,000 | 25 | 33,554,432 | 251,658,240 | >90,000,000 |
| >6,000 | 26 | 67,108,864 | 503,316,480 | >90,000,000 |
| >6,000 | 27 | 134,217,728 | 1,006,632,960 | >90,000,000 |
| >6,000 | 28 | 268,435,456 | 2,013,265,920 | >90,000,000 |
| >6,000 | 29 | 536,870,912 | 4,026,531,840 | >90,000,000 |
| >6,000 | 30 | 1,073,741,824 | 8,053,063,680 | >90,000,000 |
| >6,000 | 31 | 2,147,483,648 | 16106127360 | >90,000,000 |
| >6,000 | 32 | 4,294,967,296 | 32212254720 | >90,000,000 |
| >6,000 | 33 | 8,589,934,592 | 64424509440 | >90,000,000 |
| >6,000 | 34 | 17,179,869,184 | 1.28849E+11 | >90,000,000 |
| >6,000 | 35 | 34,359,738,368 | 2.57698E+11 | >90,000,000 |
| >6,000 | 36 | 68,719,476,736 | 5.15396E+11 | >90,000,000 |
| >6,000 | 37 | 1.37439E+11 | 1.03079E+12 | >90,000,000 |
| >6,000 | 38 | 2.74878E+11 | 2.06158E+12 | >90,000,000 |
| >6,000 | 39 | 5.49756E+11 | 4.12317E+12 | >90,000,000 |
| >6,000 | 40 | 1.09951E+12 | 8.24634E+12 | >90,000,000 |

FIG. 21

| #beads | volume (L) | concentration (M) | #molecules | AEB | foff | fon | expected signal (%) | Measured signal (%) | Standard deviation (n=3) |
|---|---|---|---|---|---|---|---|---|---|
| 140000 | 0.0001 | 10 fM | 602200 | 4.30 | 0.01 | 0.99 | 98.658 | 95.20 | 5.49 |
| 140000 | 0.0001 | 5 fM | 301100 | 2.15 | 0.12 | 0.88 | 88.36 | 81.05 | 7.43 |
| 140000 | 0.0001 | 1 fM | 60220 | 0.43 | 0.65 | 0.35 | 34.96 | 36.73 | 4.01 |
| 140000 | 0.0001 | 500 aM | 30110 | 0.22 | 0.81 | 0.19 | 19.35 | 17.25 | 2.18 |
| 140000 | 0.0001 | 100 aM | 6022 | 0.04 | 0.96 | 0.04 | 4.218 | 5.52 | 0.98 |
| 140000 | 0.0001 | 10 aM | 602.2 | 0.004 | 0.995 | 0.005 | 0.43 | 4.08 | 2.12 |
| 140000 | 0.0001 | 0 | 0 | 0 | 1 | 0 | 0 | 1.20 | 0.74 |

FIG. 23

DEVICES AND METHODS FOR SAMPLE ANALYSIS

CROSS-REFERENCE TO RELATED APPLICATIONS

This application is a 371 of International Application No. PCT/US2017/051627 filed Sep. 14, 2017, which claims the benefit of U.S. Provisional Patent Application No. 62/395,255 filed Sep. 15, 2016, which applications are incorporated herein by reference in their entirety.

INTRODUCTION

Analyte analysis is usually performed by carrying out a sample preparation step that is either performed manually or using complicated robotics. After sample preparation, the assaying of an analyte in the prepared sample further involves use of expensive and complicated systems for transporting the prepared sample to a machine that then performs analysis of an analyte in the prepared sample.

Integrated devices that can be used to prepare a sample and assay the prepared sample are highly desirable in the field of analyte analysis. Such integrated devices would offer a low cost option and would considerably increase the ease of performing analyte analysis, especially in clinical applications, such as point-of-care applications.

As such, there is an interest in integrated devices for performing analyte analysis.

SUMMARY

A method for detecting presence of a target nucleic acid in a sample is provided. In certain embodiments, the method includes amplifying the target nucleic acid in the sample by amplification to generate an amplification product, wherein the amplifying incorporates a tag into the amplification product, wherein the amplification comprises less than 15 cycles of amplification; capturing the amplification product on a plurality of capture objects comprising a binding member that specifically binds to the tag thereby generating a complex comprising capture object-amplification product; detectably labeling the amplification product in the complex to generate a detectably labeled complex; spatially segregating the capture objects into a plurality of wells, wherein the wells are sized to contain no more than one capture object per well; and detecting the presence of the detectably labeled complex in the plurality of wells.

In certain embodiments, the amplification comprises less than 14 cycles, less than 13 cycles, less than 11 cycles, or less than 10 cycles of amplification. In certain embodiments, the amplification comprises 5-15 cycles, 5-13 cycles, 6-15 cycles, 6-10 cycles, 8-15 cycles, 8-13 cycles, 8-10 cycles, 2-10 cycles, 3-10 cycles, 4-10 cycles, 5-10 cycles, or 3-5 cycles of amplification. Each amplification cycle doubles the number of target nucleic acid present at the beginning of the amplification cycle. In certain cases, the amplification generated about 6000 target nucleic acid molecules which are then detected. In certain case, the number of target nucleic acid molecules generated by the amplification cycles and detectable by the methods described herein is less than 10000, such as, 9000, 8000, 7000, 6000, 5000, 4000, 3000, 1000 such as, 10,000-100, 8000-3000, 7000-5000, or 6500-5500. The present methods may be used to detect as low as 100, 50, 30, 10 or 5 target nucleic acid present in a sample, prior to the amplification. In certain embodiments, the present methods are suitable for detection of a low number of target nucleic acid molecules in a sample, such as, 5-100 or 5-50 molecules in a sample after only 15 or less rounds of amplification.

In certain embodiments, a method for detecting presence of a target nucleic acid in a sample includes amplifying the target nucleic acid in the sample by amplification to generate an amplification product, wherein the amplifying incorporates a tag into the amplification product, wherein the amplification is performed for less than 30 minutes or less than 10 minutes; capturing the amplification product on a plurality of capture objects comprising a binding member that specifically binds to the tag thereby generating a complex comprising capture object-amplification product; detectably labeling the amplification product in the complex to generate a detectably labeled complex; spatially segregating the capture objects into a plurality of wells, wherein the wells are sized to contain no more than one capture object per well; and detecting the presence of the detectably labeled complex in the plurality of wells.

In certain embodiments, the amplification is performed for less than 9 minutes, less than 8 minutes, less than 7 minutes, less than 6 minutes, less than 5 minutes, less than 4 minutes, less than 3 minutes, less than 2 minutes, less than 1 minutes, or less than 30 seconds.

In certain embodiments, a method for detecting presence of a target nucleic acid in a sample includes amplifying the target nucleic acid in the sample by amplification to generate amplification product molecules that are as low as 1000 molecules in number, wherein the amplifying incorporates a tag into the amplification product molecules; capturing the amplification product on a plurality of capture objects comprising a binding member that specifically binds to the tag thereby generating a complex comprising capture object-amplification product; detectably labeling the amplification product in the complex to generate a detectably labeled complex; spatially segregating the capture objects into a plurality of wells, wherein the wells are sized to contain no more than one capture object per well; and detecting the presence of the detectably labeled complex in the plurality of wells.

In certain embodiments, the amplification produces amplification product molecules that are as low as 1500 molecules, as low as 2000 molecules, as low as 3000 molecules, as low as 4000 molecules, as low as 5000 molecules, or as low as 6000 molecules, as low as 7000 molecules, as low as 8000 molecules, as low as 10,000 molecules, in number.

In certain embodiments, a method for detecting presence of a target nucleic acid in a sample includes amplifying the target nucleic acid in the sample by amplification to generate an amplification product molecules that are as low as 10 aM in concentration, wherein the amplifying incorporates a tag into the amplification product molecules; capturing the amplification product on a plurality of capture objects comprising a binding member that specifically binds to the tag thereby generating a complex comprising capture object-amplification product; detectably labeling the amplification product in the complex to generate a detectably labeled complex; spatially segregating the capture objects into a plurality of wells, wherein the wells are sized to contain no more than one capture object per well; and detecting the presence of the detectably labeled complex in the plurality of wells.

In certain embodiments, the amplification product has a concentration as low as 20 aM-30 aM, as low as 30 aM-100 aM, as low as 100 aM-1 fM, as low as 1 fM-10 fM, as low as 10 fM-100 fM, or as low as 100 fM-1 pM, as low as 1 pM-10 pM, as low as 10 pM-100 pM, or as low as 100 pM, as low as 20 aM, as low as 30 aM, as low as 100 aM, as low as 1 fM, as low as 10 fM, or as low as 100 fM, as low as 1 pM, as low as 10 pM.

In certain embodiments, the method further comprises determining a percentage of wells containing the detectably labeled complex, wherein the percentage of wells is used to determine a concentration of the target nucleic acid in the fluid sample.

In other embodiments, wherein the method further comprises determining a measure of the concentration of the target nucleic acid in the fluid sample based at least in part on a measured intensity level of a signal of the detectably labeled complex in the wells.

In certain embodiments, the method comprises prior to the capturing the amplification product on a plurality of capture objects denaturing the amplification product to generate a first nucleic acid strand and a second nucleic acid strand, wherein the first nucleic acid strand includes the tag, wherein the tag is a first tag; annealing probe to the first nucleic acid strand, wherein the probe is complementary to a segment of the first nucleic acid strand, wherein the probe comprises a second tag which is different from the first tag; capturing the first nucleic acid strand comprising the first tag on the plurality of capture objects comprising the binding member, which is a first binding member that specifically binds to the first tag to generate a capture object-first nucleic acid complex; contacting the capture object-first nucleic acid complex with a second binding member that specifically binds to the second tag in the probe, wherein the second binding member is detectably labeled, thereby generating the detectably labeled complex.

In certain embodiments, the amplification product comprises a first nucleic acid strand and a second nucleic acid strand and wherein the amplifying incorporates a first tag in the first nucleic acid strand and a second tag into the second nucleic acid strand, wherein the capturing the amplification product comprises; (a) capturing the first nucleic acid strand on a plurality of capture objects comprising a first binding member that specifically binds to the first tag thereby generating the complex comprising capture object-amplification product, wherein detectably labeling the amplification product in the complex to generate the detectably labeled complex comprises: contacting the complex with a second binding member that specifically binds to the second tag, wherein the second binding member is detectably labeled, thereby generating the detectably labeled complex; or (b) capturing the second nucleic acid strand on a plurality of capture objects comprising a second binding member that specifically binds to the second tag thereby generating a complex comprising capture object-amplification product, wherein detectably labeling the amplification product in the complex to generate the detectably labeled complex comprises contacting the complex with a first binding member that specifically binds to the first tag, wherein the first binding member is detectably labeled, thereby generating the detectably labeled complex.

In another embodiment, a first nucleic acid strand in the amplification product comprises a first tag and wherein the plurality of capture objects comprise a first binding member that specifically binds to the first tag and wherein the first nucleic acid strand comprises a plurality of nucleotides that comprise a second tag, wherein capturing the amplification product comprises contacting the amplification product with the plurality of capture object comprising the first binding member to generate the complex comprising the capture object-amplification product, wherein the detectably labeling the amplification product in the complex to generate a detectably labeled complex comprises: contacting the complex with a second binding member that specifically binds to the second tag, wherein the second binding member is detectably labeled, thereby generating the detectably labeled complex.

In some embodiments, the detectably labeled complex comprises a signaling moiety that produces a detectable signal. In some embodiments, the signaling moiety is an enzyme that acts on a substrate to produce a detectable signal.

An integrated microfluidic and analyte detection device is also disclosed. Also provided herein are exemplary methods for using an integrated microfluidic and analyte detection device and associated systems.

In certain embodiments, an integrated digital microfluidic and analyte detection device may include a first substrate and a second substrate, wherein the second substrate is positioned over the first substrate and separated from the first substrate by a gap; the first substrate comprising: a series of electrodes positioned on an upper surface of the first substrate; a first layer disposed on the upper surface of the first substrate and covering the series of electrodes; wherein the first substrate comprises a proximal portion at which a liquid droplet is introduced and a distal portion toward which a liquid droplet is moved, wherein the series of electrodes and the first layer extend from the proximal portion to the distal portion; and an array of wells positioned in the distal portion of the first substrate, where the array of wells is positioned in the distal portion and does not extend to the proximal portion of the device.

In certain cases, the second substrate includes a proximal portion and a distal portion, wherein the proximal portion overlays the proximal portion of the first substrate and the distal portion overlays the array of wells, wherein the distal portion of the second substrate is substantially transparent to facilitate optical interrogation of the array of wells. In certain cases, a second layer is disposed on an upper surface of the first layer. The second layer may extend over the proximal and distal portions of the first substrate.

The first layer may be made of a material that is dielectric and hydrophobic. The array of wells may be positioned in the first layer. In other cases, the first layer may be made of dielectric layer and the second layer may be a hydrophobic layer. The array of wells may be positioned in the second layer. In certain cases, the array of wells may have a hydrophilic surface.

In certain cases, the array of wells may include a sidewall that is oriented to facilitate receiving and retaining of beads or particles or labels or other molecules present in droplets moved over the well array. The wells may comprise a first sidewall opposite to a second side wall, wherein the first sidewall is oriented at an obtuse angle with reference to a bottom of the wells, and wherein the second sidewall is oriented at an acute angle with reference to the bottom of the wells, wherein the movement of droplets is in a direction parallel to the bottom of the wells and from the first sidewall to the second sidewall. The wells may have a frustoconical shape with the narrower part of the frustoconical shape providing the opening of the wells.

In certain cases, the wells comprise a first sidewall opposite to a second side wall, wherein a top portion of the first sidewall is oriented at an obtuse angle with reference to a bottom of the wells and a bottom portion of the sidewall is oriented perpendicular to the bottom of the wells, and wherein the second sidewall is oriented perpendicular with reference to the bottom of the wells, wherein the movement of droplets is in a direction parallel to the bottom of the wells and from the first sidewall to the second sidewall, wherein the top portion of the first side wall is at an opening of the wells.

In certain embodiments, an integrated digital microfluidic and analyte detection device is provided that includes a first substrate and a second substrate, wherein the second substrate is positioned over the first substrate and separated from the first substrate by a gap; the first substrate comprising: a proximal portion at which a liquid droplet is placed on the first substrate and a distal portion towards which the liquid droplet is moved; a series of electrodes positioned on an upper surface of the first substrate at the proximal portion of the first substrate, wherein the series of electrodes are not positioned in the distal portion of the first substrate; a first layer disposed on the upper surface of the array of electrodes and covering the series of electrodes; and an array of wells positioned in the distal portion of the first substrate.

In certain cases, the second substrate includes a proximal portion and a distal portion, wherein the proximal portion overlays the proximal portion of the first substrate and the distal portion overlays the array of wells, wherein the distal portion of the second substrate is substantially transparent to facilitate optical interrogation of the array of wells, the series of electrodes are configured to move a droplet placed in the gap towards the distal portion of the device, the device comprising a capillary portion fluidically connecting the proximal portion to the distal portion, wherein the capillary comprises a hydrophilic material to facilitate movement of the droplet from the proximal portion to the distal portion via the capillary portion in absence of an electric force. In certain cases, a second layer is disposed on an upper surface of the first layer. In certain cases, the second layer extends over the proximal and distal portions of the first substrate.

Also disclosed herein is an integrated surface acoustic wave microfluidic and analyte detection device, comprising: a first substrate and a second substrate, wherein the second substrate is positioned over the first substrate and separated from the first substrate by a gap; the first substrate comprising: a proximal portion and a distal portion, where the proximal portion is adjacent to a sample inlet element and the distal portion is downstream from the proximal portion, the proximal portion comprising a superstrate coupled to a surface acoustic wave generating component; and the distal portion comprising an array of wells positioned on an upper surface of the first substrate.

In certain embodiments, the superstrate includes phononic structures on an upper surface of the superstrate. In certain embodiments, the superstrate overlays a piezoelectric crystal layer. In certain embodiments, the second substrate is substantially transparent.

In another embodiment, an integrated surface acoustic wave microfluidic and analyte detection device is provided that includes: a first substrate spaced apart from a second substrate; the first substrate comprising an array of wells and the second substrate comprising phononic structure, wherein the array of wells and the phononic structures are located across to each other, wherein the second substrate is a superstrate or wherein a superstrate is disposed on the second substrate and the phononic structure are located on the superstrate.

BRIEF DESCRIPTION OF THE DRAWINGS

FIG. 4A illustrates a side view of the device of FIG. 2A with a droplet containing nanoparticles/nanobeads being moved onto an array of wells.

FIG. 4B illustrates a side view of the device of FIG. 2B with a droplet containing nanoparticles/nanobeads being moved onto an array of wells with a droplet of an immiscible fluid.

FIG. 21 depicts comparison of level of amplification required for digital vs. analog detection for NAT.

FIG. 23 provides measured and expected signal expressed as percentage of beads that are bound to the DL-DNA.

DETAILED DESCRIPTION OF THE INVENTION

Figure 1A:
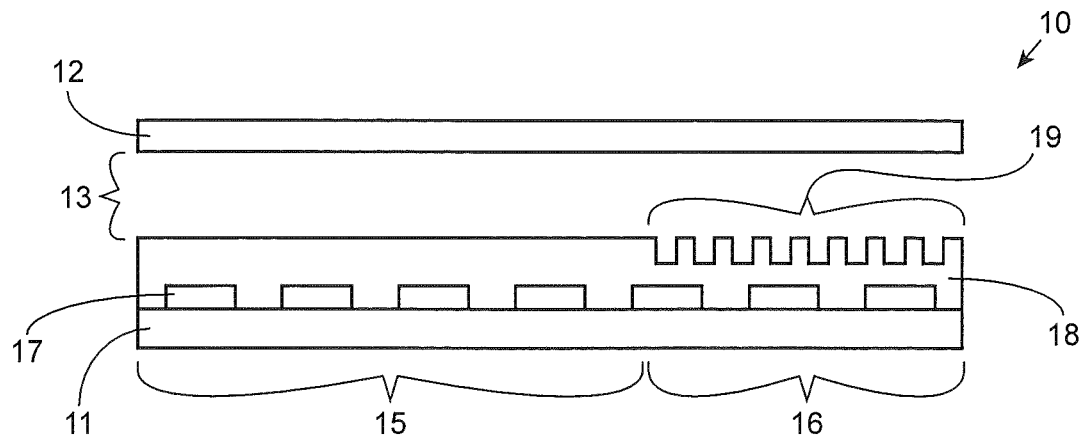
FIG. 1A illustrates a side view of an integrated digital microfluidic and analyte detection device according to one embodiment.

An integrated microfluidic and analyte detection device is disclosed. Also provided herein are exemplary methods for using an integrated microfluidic and analyte detection device and associated systems.

Before the present invention is described in greater detail, it is to be understood that this invention is not limited to a particular embodiment described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "an" and "the" include plural referents unless the context clearly dictates otherwise. Thus, for example, refer to "an electrode" includes plurality of such electrodes and reference to "the well" includes reference to one or more wells and equivalents thereof known to those skilled in the art, and so forth.

All publications mentioned herein are incorporated herein by reference to disclose and describe the methods and/or materials in connection with which the publications are cited. The present disclosure is controlling to the extent there is a contradiction between the present disclosure and a publication incorporated by reference.

Integrated Digital Microfluidic and Analyte Detection Device

Systems, devices, and method are described herein that relate to an integrated digital microfluidic and analyte detection device.

In certain embodiments, the integrated digital microfluidic and analyte detection device may have two modules: a sample preparation module and an analyte detection module. The sample preparation module may include a series of electrodes for moving, merging, diluting, mixing, separating droplets of samples and reagents. The analyte detection module may include an array of wells in which an analyte related signal is detected. In certain cases, the detection module may also include the series of electrodes for moving a droplet of prepared sample to the array of wells. In other embodiments, the series of electrodes may be limited to the sample preparation module and a droplet of prepared sample (and/or a droplet of immiscible fluid) may be moved to the detection module using other means.

In certain embodiments, the sample preparation module may be used for performing steps of an immunoassay. Any immunoassay format may be used to generate a detectable signal which signal is indicative of presence of an analyte of interest in a sample and is proportional to the amount of the analyte in the sample. Exemplary immunoassays are described herein.

In certain cases, the detection module includes the array of wells that are optically interrogated to measure a signal related to the amount of analyte present in the sample. The array of wells may have sub-femtoliter volume, femtoliter volume, sub-nanoliter volume, nanoliter volume, sub-microliter volume, or microliter volume. For example the array of wells may be array of femtoliter wells, array of nanoliter wells, or array of microliter wells. In certain embodiments, the wells in an array may all have substantially the same volume. The array of wells may have a volume up to 100 µl, e.g., about 0.1 femtoliter, 1 femtoliter, 10 femtoliter, 25 femtoliter, 50 femtoliter, 100 femtoliter, 0.1 pL, 1 pL, 10 pL, 25 pL, 50 pL, 100 pL, 0.1 nL, 1 nL, 10 nL, 25 nL, 50 nL, 100 nL, 0.1 microliter, 1 microliter, 10 microliter, 25 microliter, 50 microliter, or 100 microliter.

In certain embodiments, the sample preparation module and the detection module may both be present on a single base substrate and both the sample preparation module and the detection module may include a series of electrodes for moving liquid droplets. In certain embodiments, such a device may include a first substrate and a second substrate, where the second substrate is positioned over the first substrate and separated from the first substrate by a gap. The first substrate may include a proximal portion at which the sample preparation module is located, where a liquid droplet is introduced into the device, and a distal portion towards which the liquid droplet moves, at which distal portion the detection module is located. The first substrate may include a series of electrodes overlayed on an upper surface of the first substrate and extending from the proximal to the distal portion. The first substrate may include a layer disposed on the upper surface of the first substrate, covering the series of electrodes, and extending from the proximal to the distal portion. The first layer may be made of a material that is a dielectric and a hydrophobic material. Examples of a material that is dielectric and hydrophobic include polytetrafluoroethylene material (e.g., Teflon®) or a fluorosurfactant (e.g., FluoroPel™). The first layer may be deposited in a manner to provide a substantially planar surface. An array of wells may be positioned in the distal portion of the first substrate and overlying a portion of the series of electrodes, and form the detection module. The array of wells may be positioned in the first layer. In certain embodiments, prior to or after fabrication of the array of wells in the first layer, a hydrophilic layer may be disposed over the first layer in the distal portion of the first substrate to provide an array of wells that have a hydrophilic surface. The space/gap between the first and second substrates may be filled with air or an immiscible fluid. In certain embodiments, the space/gap between the first and second substrates may be filled with air.

In certain embodiments, the sample preparation module and the detection module may both be fabricated using a single base substrate but a series of electrodes for moving liquid droplets may only be present only in the sample preparation module. In such an embodiment, the first substrate may include a series of electrodes overlayed on an upper surface of the first substrate at the proximal portion of the first substrate, where the series of electrodes do not extend to the distal portion of the first substrate. A first layer of a dielectric/hydrophobic material (e.g., Teflon), as described above, may be disposed on the upper surface of the first substrate and may cover the series of electrodes. In certain embodiments, the first layer may be disposed only over a proximal portion of the first substrate. In other embodiments, the first layer may be disposed over the upper surface of the first substrate over the proximal portion as well as the distal portion. An array of wells may be positioned in the first layer in the distal portion of the first substrate, forming the detection module that does not include a series of electrodes present under the array of wells.

In certain cases, the first layer may be a dielectric layer and a second layer of a hydrophobic material may be disposed over the dielectric layer. The array of wells may be positioned in the hydrophobic layer. Prior to or after fabrication of the array of wells in the hydrophobic layer, a hydrophilic layer may be disposed over the hydrophobic layer in the distal portion of the first substrate.

In certain embodiments, the second substrate may extend over the proximal and distal portions of the first substrate. In such an embodiment, the second substrate may be substantially transparent, at least in region overlaying the array of wells. In other cases, the second substrate may be disposed in a spaced apart manner over the proximal portion of the first substrate and may not be disposed over the distal portion of the first substrate. Thus, in certain embodiments, the second substrate may be present in the sample preparation module but not in the detection module.

In certain cases, the second substrate may include a conductive layer that forms an electrode. The conductive layer may be disposed on a lower surface of the second substrate. The conductive layer may be covered by a first layer made of a dielectric/hydrophobic material, as described above. In certain cases, the conductive layer may be covered by a dielectric layer. The dielectric layer may be covered by a hydrophobic layer. The conductive layer and any layer(s) covering it may be disposed across the lower surface of the second substrate or may only be present on the proximal portion of the second substrate. In certain embodiments, the second substrate may extend over the proximal and distal portions of the first substrate. In such an embodiment, the second substrate and any layers disposed thereupon (e.g., conductive layer, dielectric layer, etc.) may be substantially transparent, at least in region overlaying the array of wells.

In other cases, the array of electrodes on the first substrate may be configured as co-planar electrodes and the second substrate may not include an electrode.

In certain cases, the electrodes present in the first layer and/or the second layer may be fabricated from a substantially transparent material, such as indium tin oxide, fluorine doped tin oxide (FTC)), doped zinc oxide, and the like.

In some embodiments, the sample preparation module and the detection modules may be fabricated on a single base substrate. In other embodiments, the sample preparation module and the detection modules may be fabricated on separate substrates that may subsequently be joined to form an integrated microfluidic and analyte detection device. In certain embodiments, the first and second substrates may be spaced apart using a spacer that may be positioned between the substrates.

The devices described herein may be planar and may have any shape, such as, rectangular or square, rectangular or square with rounded corners, and the like.

Droplet-based microfluidics refer to generating and actuating (such as moving, merging, splitting, etc.) liquid droplets via active or passive forces. Examples of active forces include, but are not limited to, electric field. Exemplary active force techniques include electrowetting, dielectrophoresis, opto-electrowetting, electrode-mediated, electric-field mediated, electrostatic actuation, and the like or a combination thereof. In some examples, the device may actuate liquid droplets across the upper surface of the first layer (or upper surface of the second layer, when present) in the gap via droplet-based microfluidics, such as, electrowetting or via a combination of electrowetting and continuous fluid flow of the liquid droplets. In other examples, the device may include micro-channels to deliver liquid droplets from the sample preparation module to the detection module. In other examples, the device may rely upon the actuation of liquid droplets across the surface of the hydrophobic layer in the gap via droplet based microfluidics. Electrowetting may involve changing the wetting properties of a surface by applying an electrical field to the surface, and affecting the surface tension between a liquid droplet present on the surface and the surface. Continuous fluid flow may be used to move liquid droplets via an external pressure source, such as an external mechanical pump or integrated mechanical micropumps, or a combination of capillary forces and electrokinetic mechanisms. Examples of passive forces include, but are not limited to, T-junction and flow focusing methods. Other examples of passive forces include use of denser immiscible liquids, such as, heavy oil fluids, which can be coupled to liquid droplets over the surface of the first substrate and displace the liquid droplets across the surface. The denser immiscible liquid may be any liquid that is denser than water and does not mix with water to an appreciable extent. For example, the immiscible liquid may be hydrocarbons, halogenated hydrocarbons, polar oil, non-polar oil, fluorinated oil, chloroform, dichloromethane, tetrahydrofuran, 1-hexanol, etc.

The space between the first and second substrates may be up to 1 mm in height, e.g., 0.1 µm, 0.5 µm, 1 µm, 5 µm, 10 µm, 20 µm, 50 µm, 100 µm, 140 µm, 200 µm, 300 µm, 400 µm, 500 µm, 1 µm-500 µm, 100 µm-200 µm, etc. The volume of the droplet generated and moved in the devices described herein may range from about 10 µl to about 5 picol, such as, 10 µl-1 picol, 7.5 µl-10 picol, 5 µl-1 nL, 2.5 µl-10 nL, or 1 µl-100 nL, 800-200 nL, 10 nL-0.5 µl e.g., 10 µl, 1 µl, 800 nL, 100 nL, 10 nL, 1 nL, 0.5 nL, 10 picol, or lesser.

FIG. 1A illustrates an exemplary integrated digital microfluidic and analyte detection device 10. The device 10 includes a first substrate 11 and a second substrate 12, where the second substrate 12 is positioned over the first substrate 11 and separated from the first substrate by a gap 13. As illustrated in FIG. 1A, the second substrate 12 is the same length as the first substrate 11. However, in other exemplary devices, the first substrate and the second substrate may be of different lengths. The second substrate may or may not include an electrode. The first substrate 11 includes a proximal portion 15, where liquid droplet, such as, a sample droplet, reagent droplet, etc., is introduced onto the first substrate 11. The first substrate 11 includes a distal portion 16, towards which a liquid droplet is moved. The proximal portion may also be referred to as the sample preparation module and the distal portion may be referred to as the analyte detection module. The first substrate 11 includes a series of electrodes 17 positioned on the upper surface of the first substrate. A layer 18 of dielectric/hydrophobic material (e.g., Teflon which is both dielectric and hydrophobic) is disposed on the upper surface of the first substrate and covers the series of electrodes 17. An array of wells 19 is positioned in the dielectric layer 18 on the distal portion of the first substrate 16.

Figure 1B:
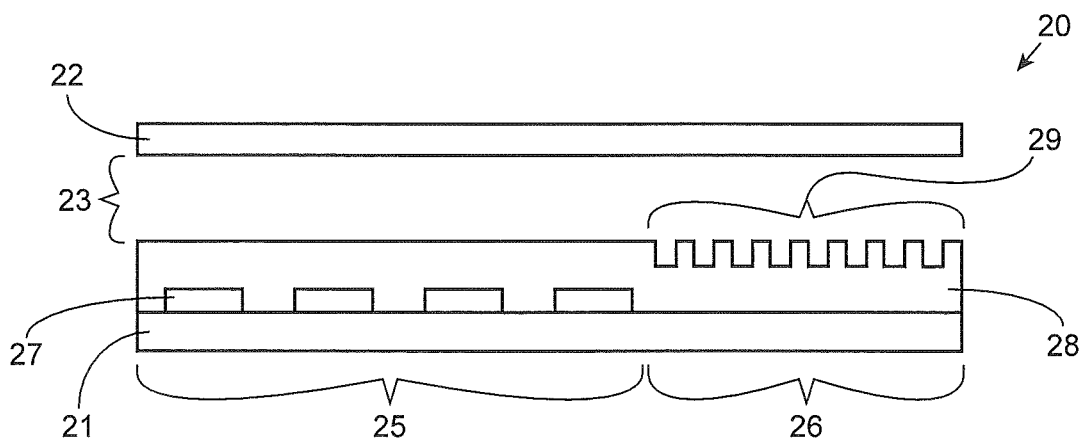
FIG. 1B illustrates a side view of the integrated digital microfluidic and analyte detection device according to another embodiment.

FIG. 1B illustrates another example of an integrated digital microfluidic and analyte detection device 20 that includes a first substrate 21 and a second substrate 22, where the second substrate 22 is positioned over the first substrate 20 and separated from an upper surface of the first substrate by a gap 23. The first substrate 21 includes a proximal portion 25, where a liquid is introduced onto the first substrate 21, and a distal portion 26, towards which liquid is directed for detection of an analyte related signal. The first substrate 21 includes a series of electrodes 27 positioned on the upper surface of the first substrate. A layer 28 of dielectric material is positioned on the upper surface of the first substrate 21 and covers the series of electrodes 27. In this exemplary device, the series of electrodes 27 is positioned on only the proximal portion of the first substrate 21. The second substrate may or may not include an electrode. An array of wells 29 is positioned in the dielectric layer 28 on the distal portion of the first substrate 21.

Figure 2A:
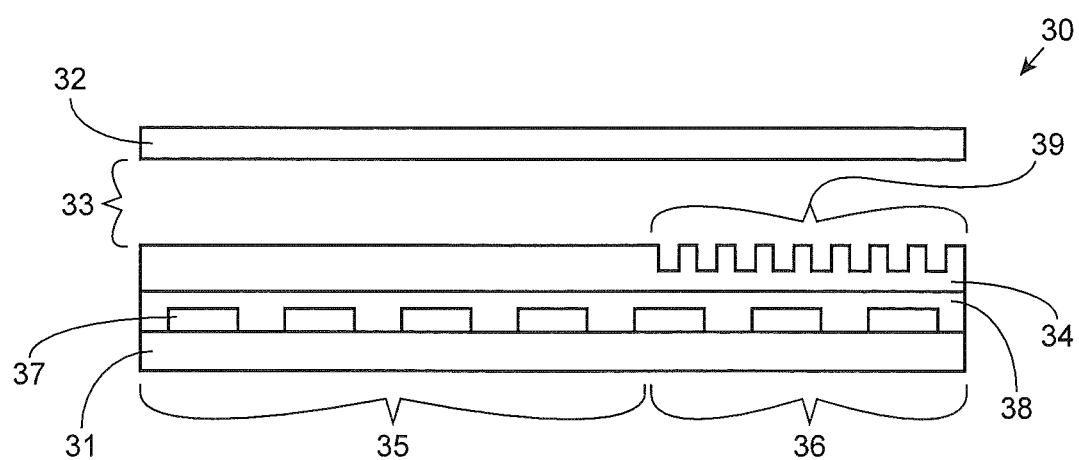
FIG. 2A illustrates a side view of an integrated digital microfluidic and analyte detection device according to an embodiment.

FIG. 2A illustrates another exemplary integrated digital microfluidic and analyte detection device 30. The device 30 includes a first substrate 31 and a second substrate 32, where the second substrate 32 is positioned over the first substrate 31 and separated from an upper surface of the first substrate by a gap 33. The first substrate 31 includes a proximal portion 35, where liquid droplet, such as, a sample droplet, reagent droplet, etc., is introduced onto the first substrate 31. The first substrate 31 includes a distal portion 36, towards which a liquid droplet is moved. The proximal portion may also be referred to as the sample preparation module and the distal portion may be referred to as the detection module. The first substrate 31 includes a series of electrodes 37 positioned on the upper surface of the first substrate. A layer 38 of dielectric material is disposed on the upper surface of the first substrate and covers the series of electrodes 37. A layer 34 of hydrophobic material is overlayed on the dielectric layer 38. An array of wells 39 is positioned in the hydrophobic layer 34 on the distal portion of the first substrate 31. The array of wells may have a hydrophilic or hydrophobic surface.

Figure 2B:
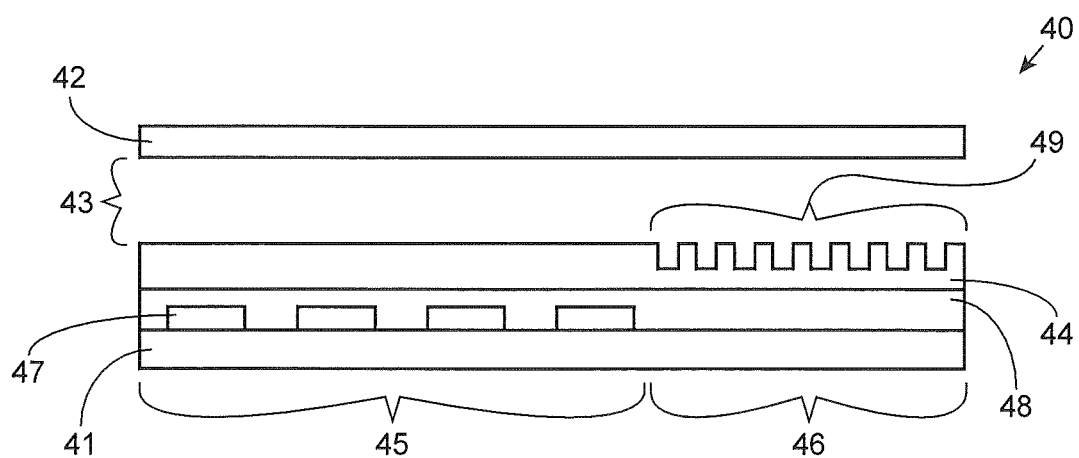
FIG. 2B illustrates a side view of the integrated digital microfluidic and analyte detection device according to another embodiment.

FIG. 2B illustrates another example of an integrated digital microfluidic and analyte detection device 40 that includes a first substrate 41 and a second substrate 42, where the second substrate 42 is positioned over the first substrate 40 and separated from an upper surface of the first substrate by a gap 43. The first substrate includes a proximal portion 45, where a liquid is introduced onto the first substrate 41, and a distal portion 46, towards which liquid is directed for detection of an analyte related signal. The first substrate 41 includes a series of electrodes 47 positioned on the upper surface of the first substrate. A layer 48 of dielectric material is positioned on the upper surface of the first substrate 41 and covers the series of electrodes 47. In this exemplary device, the series of electrodes 47 is positioned on only the proximal portion 45 of the first substrate 41. The dielectric layer 48 covers the entire upper surface of the first substrate 41 and the hydrophobic layer 44 covers the entire upper surface of the dielectric layer. An array of wells 49 is positioned in the hydrophobic layer 44, and the array of wells 49 are positioned at only a portion of the hydrophobic layer overlaying the distal portion 46 of the first substrate 41. In this example, the dielectric layer 48 is shown as extending over the entire upper surface of the first substrate 41. In other examples, the dielectric layer and the hydrophobic layer may be limited to the proximal portion and the wells may be positioned in a hydrophilic layer positioned on the distal portion of the first substrate.

In some examples, liquid may be introduced into the gap via a droplet actuator (not illustrated). In other examples, liquid may be into the gap via a fluid inlet, port, or channel. Additional associated components of the device are not illustrated in the figures. Such figures may include chambers for holding sample, wash buffers, binding members, enzyme substrates, waste fluid, etc. Assay reagents may be contained in external reservoirs as part of the integrated device, where predetermined volumes may be moved from the reservoir to the device surface when needed for specific assay steps. Additionally, assay reagents may be deposited on the device in the form of dried, printed, or lyophilized reagents, where they may be stored for extended periods of time without loss of activity. Such dried, printed, or lyophilized reagents may be rehydrated prior or during analyte analysis.

In some examples, the first substrate can be made from a flexible material, such as paper (with ink jet printed electrodes), polymers. In other examples, the first substrate can be made from a non-flexible material, such as for example, printed circuit board, plastic or glass or silicon. In some examples, the first substrate is made from a single sheet, which then may undergo subsequent processing to create the series of electrodes. In some examples, multiple series of electrodes may be fabricated on a first substrate which may be cut to form a plurality of first substrates overlayed with a series of electrodes. In some examples, the electrodes may be bonded to the surface of the conducting layer via a general adhesive agent or solder. The second substrate may be made from any suitable material including but not limited to a flexible material, such as paper (with or without ink jet printed electrodes), polymers, printed circuit board, and the like.

In some examples, the electrodes are comprised of a metal, metal mixture or alloy, metal-semiconductor mixture or alloy, or a conductive polymer. Some examples of metal electrodes include copper, gold, indium, tin, indium tin oxide, and aluminum. In some examples, the dielectric layer comprises an insulating material, which has a low electrical conductivity or is capable of sustaining a static electrical field. In some examples, the dielectric layer may be made of porcelain (e.g., a ceramic), polymer or a plastic. In some examples, the hydrophobic layer may be made of a material having hydrophobic properties, such as for example Teflon, poly(p-xylylene) polymers and generic fluorocarbons. In another example, the hydrophobic material may be a fluorosurfactant (e.g., FluoroPel). In embodiments including a hydrophilic layer deposited on the dielectric layer, it may be a layer of glass, quartz, silica, metallic hydroxide, or mica.

One having ordinary skill in the art would appreciate that the series of electrodes may include a certain number of electrodes per unit area of the first substrate, which number may be increased or decreased based on size of the electrodes and a presence or absence of inter-digitated electrodes. Electrodes may be fabricated using a variety of processes including, photolithography, atomic layer deposition, laser scribing or etching, laser ablation, and ink-jet printing of electrodes.

In some examples, a special mask pattern may be applied to a conductive layer disposed on an upper surface of the first substrate followed by laser ablation of the exposed conductive layer to produce a series of electrodes on the first substrate.

In some examples, the electrical potential generated by the series electrodes transfer liquid droplets formed on an upper surface of the first layer (or the second layer when present) covering the series of electrodes, across the surface of the digital microfluidic device to be received by the array of wells. Each electrode may be capable of independently moving the droplets across the surface of the digital microfluidic device.

Figure 3A:
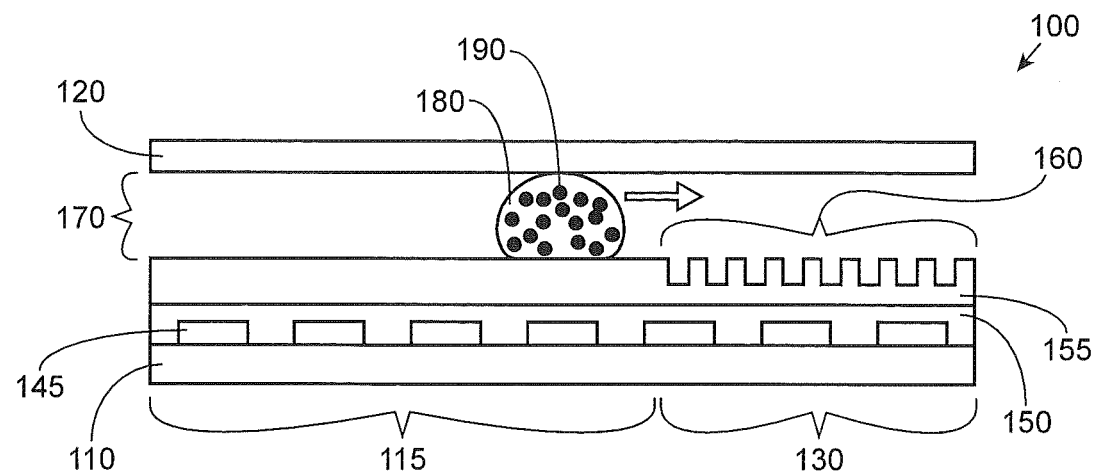
FIG. 3A illustrates a side view of the device of FIG. 2A with a liquid droplet being moved in the device.

FIG. 3A illustrates a side view of an exemplary integrated digital microfluidic and analyte detection device 100 with a droplet being moved in the gap 170. The integrated digital microfluidic device 100 includes a first substrate 110 and a second substrate 120, where the second substrate 120 is positioned over the first substrate 110 and separated from an upper surface of the first substrate by a gap 170. A layer 150 of dielectric material is positioned on the upper surface of the first substrate 110 and covers the series of electrodes 145. The dielectric layer 150 covers the entire upper surface of the first substrate 110 and the hydrophobic layer 155 covers the entire upper surface of the dielectric layer. As illustrated in FIG. 3A, a liquid droplet is illustrated as being actuated from the proximal portion 115 to the distal portion 130 containing the array of wells 160. A liquid droplet 180 containing a plurality of nanobeads or nanoparticles 190 is being moved across the proximal portion 115 and over to the distal portion 130 via active directional movement using the series of electrodes 145. The arrow indicates the direction of movement of the liquid droplet. Although not shown here, polarizable oil may be used to move the droplet and seal the wells. Although nanobeads/nanoparticles are illustrated here, the droplet may include analyte molecules instead of or in addition to the nanobeads/nanoparticles.

Figure 3B:
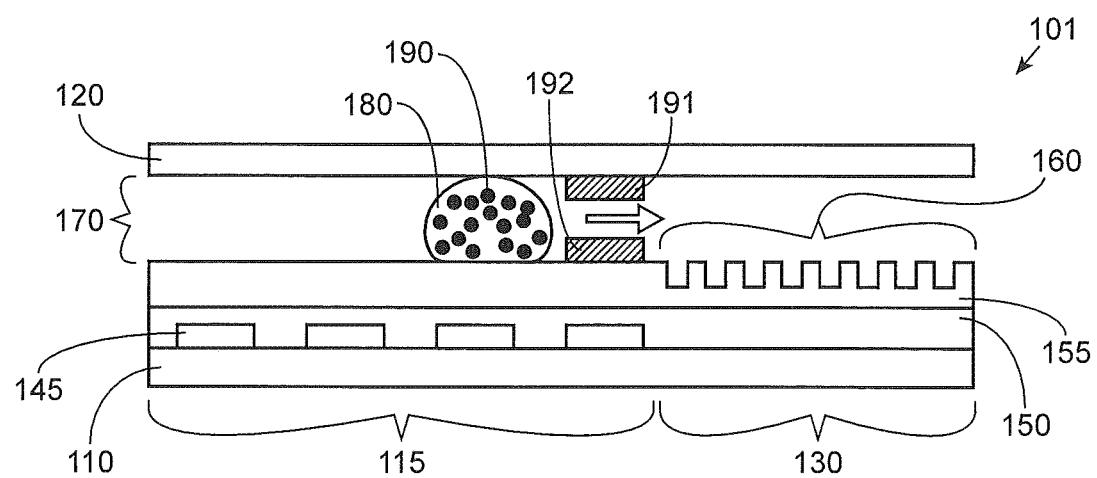
FIG. 3B illustrates a side view of the device of FIG. 2B with of droplet being moved in the device.

FIG. 3B illustrates a side view of an exemplary integrated digital microfluidic and analyte detection device 101 with a droplet 180 being moved in the gap 170 from the proximal portion 115 to the distal portion 130 that includes the array of wells 160. The integrated digital microfluidic device 101 includes a first substrate 110 and a second substrate 120, where the second substrate 120 is positioned over the first substrate 110 and separated from an upper surface of the first substrate by a gap 170. A layer 150 of dielectric material is positioned on the upper surface of the first substrate 110 and covers the series of electrodes 145. The dielectric layer 150 covers the entire upper surface of the first substrate 110 and the hydrophobic layer 155 covers the entire upper surface of the dielectric layer. Movement across the surface of the proximal portion of the device is via the electrodes 145 and then the droplet 180 is moved to the distal portion using passive fluid force, such as capillary movement through capillary element formed by 191 and 192. In some examples, the capillary element may include a hydrophilic material for facilitating movement of the aqueous droplet from the proximal portion to the distal portion in the absence of an applied electric field generated by the series of electrodes. In some examples, a striping of a hydrophobic material may be disposed next to the hydrophilic capillary space. The striping of hydrophobic material may be used to move a droplet of immiscible fluid over to the array of wells in absence of the digital microfluidics electrodes. Some examples of liquids that may flow through a hydrophobic capillary element includes heavy oil fluids, such as fluorinated oils, can be used to facilitate liquid droplet movement over the array of wells. In other examples, oil droplets may also be utilized to remove excess droplets.

In addition to moving aqueous-based fluids, organic-based immiscible fluids may also be moved by electrical-mediated actuation. It is understood that droplet actuation is correlated with dipole moment and dielectric constant, which are interrelated, as well as with conductivity. In certain embodiments, the immiscible liquid may have a molecular dipole moment greater than about 0.9 D, dielectric constant greater than about 3 and/or conductivities greater than about $10^{-9}$ S m$^{-1}$. Examples of movable immiscible liquids and characteristics thereof are discussed in Chatterjee, et al. Lab on Chip, 6, 199-206 (2006). Examples of use of the immiscible liquid in the analyte analysis assays disclosed herein include aiding aqueous droplet movement, displacing aqueous fluid positioned above the nanowells, displacing undeposited beads/particles/analyte molecules from the wells prior to optical interrogation of the wells, sealing of the wells, and the like. Some examples of organic-based immiscible fluids that are moveable in the devices disclosed herein include 1-hexanol, dichloromethane, dibromomethane, THF and chloroform. Organic-based oils that satisfy the above mentioned criteria would also be expected to be moveable under similar conditions. In embodiments using immiscible fluid droplets, the gap/space in the device may be filled with air.

FIG. 4A illustrates a liquid droplet 180 containing nanobeads or nanoparticles 190 that has been moved to the distal portion of the integrated device and is positioned over the array of wells 160. The device includes a first substrate 110, a layer 150 of dielectric material positioned on the upper surface of the first substrate and a hydrophobic layer 155 that covers the upper surface of the dielectric layer. The droplet may be continuously moved over the array of wells or movement may be paused over the array of wells. Moving of the droplet and/or pausing the droplet over the array of wells facilitates the deposition of the nanoparticles or nanobeads 190 into the array of wells 160. The wells are dimensioned to include one nanobead/nanoparticle. In the device illustrated in FIG. 4A, the droplet is moved over the array of wells using the series of electrodes 145. Although nanobeads/nanoparticles are depicted here, droplets contain analyte molecules may also be moved in a similar manner, and by pausing the droplet containing the analyte molecules above the wells for a sufficient period of time to allow for the analyte molecules to diffuse into the wells before the immiscible fluid seals the wells. The wells are dimensioned to include one nanobead/nanoparticle. The wells can also be dimensioned to include one analyte molecule per well.

FIG. 4B illustrates a liquid droplet 185 containing nanobeads or nanoparticles 190 that has been moved to the distal portion of the integrated device and is positioned over the array of wells without using a series of electrodes. The device includes a first substrate 110, a layer 150 of dielectric material positioned on the upper surface of the first substrate and a hydrophobic layer 155 that covers the upper surface of the dielectric layer. In FIG. 4B, a droplet of hydrophobic liquid 195 is being used to move the liquid droplet over the nanowell array to facilitate deposition of the nanobeads/nanoparticles 190 into the wells 160. The direction of the arrow indicates the direction in which the droplet 185 is being moved.

Figure 5:
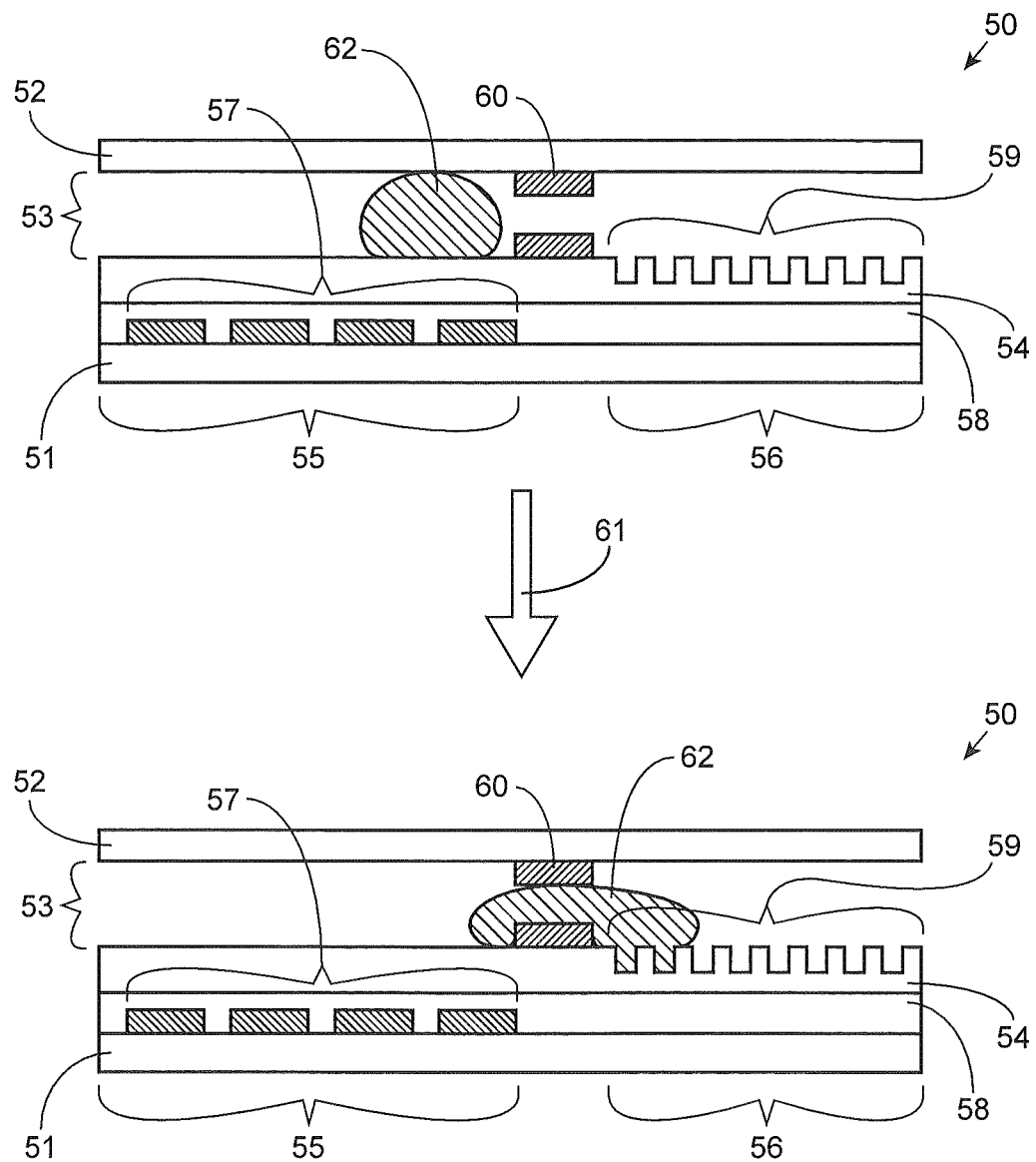
FIG. 5 illustrates an aqueous droplet being moved over the array of wells using a hydrophilic capillary region of the device 50.

FIG. 5 illustrates an exemplary integrated digital microfluidic and analyte detection device 50 having a first substrate 51 and a second substrate 52, where the second substrate 52 is positioned over the first substrate 51 and separated from an upper surface of the first substrate by a gap 53. FIG. 5 shows a hydrophobic fluid droplet 62 (e.g., polarizable oil) being moved over the proximal portion 55 using the array of electrodes 57. The device includes a first substrate 51, a layer 58 of dielectric material positioned on the upper surface of the first substrate and a hydrophobic layer 54 that covers the upper surface of the dielectric layer. A capillary element 60 is formed by deposition of two stripes of a hydrophobic material on the first 51 and second substrates 52. The hydrophobic capillary facilitates movement (indicated by the arrow 61) of the polarizable oil droplet 62 to the array of wells 59, in absence of the array of electrodes in the distal portion 56. In other embodiments, the capillary element may be formed by deposition of two stripes of a hydrophilic material on the first 51 and second substrates 52. The hydrophobic material facilitates movement of an aqueous droplet to the array of wells 59, in absence of the array of electrodes in the distal portion 56. In certain embodiments, the capillary element may include a pair of stripes of hydrophilic material alternating with a pair of stripes of hydrophobic material. An aqueous droplet may be directed to the region at which a pair of hydrophilic stripes is positioned, while a droplet of immiscible fluid may be directed to the region at which a pair of hydrophobic stripes is positioned.

Figure 6:
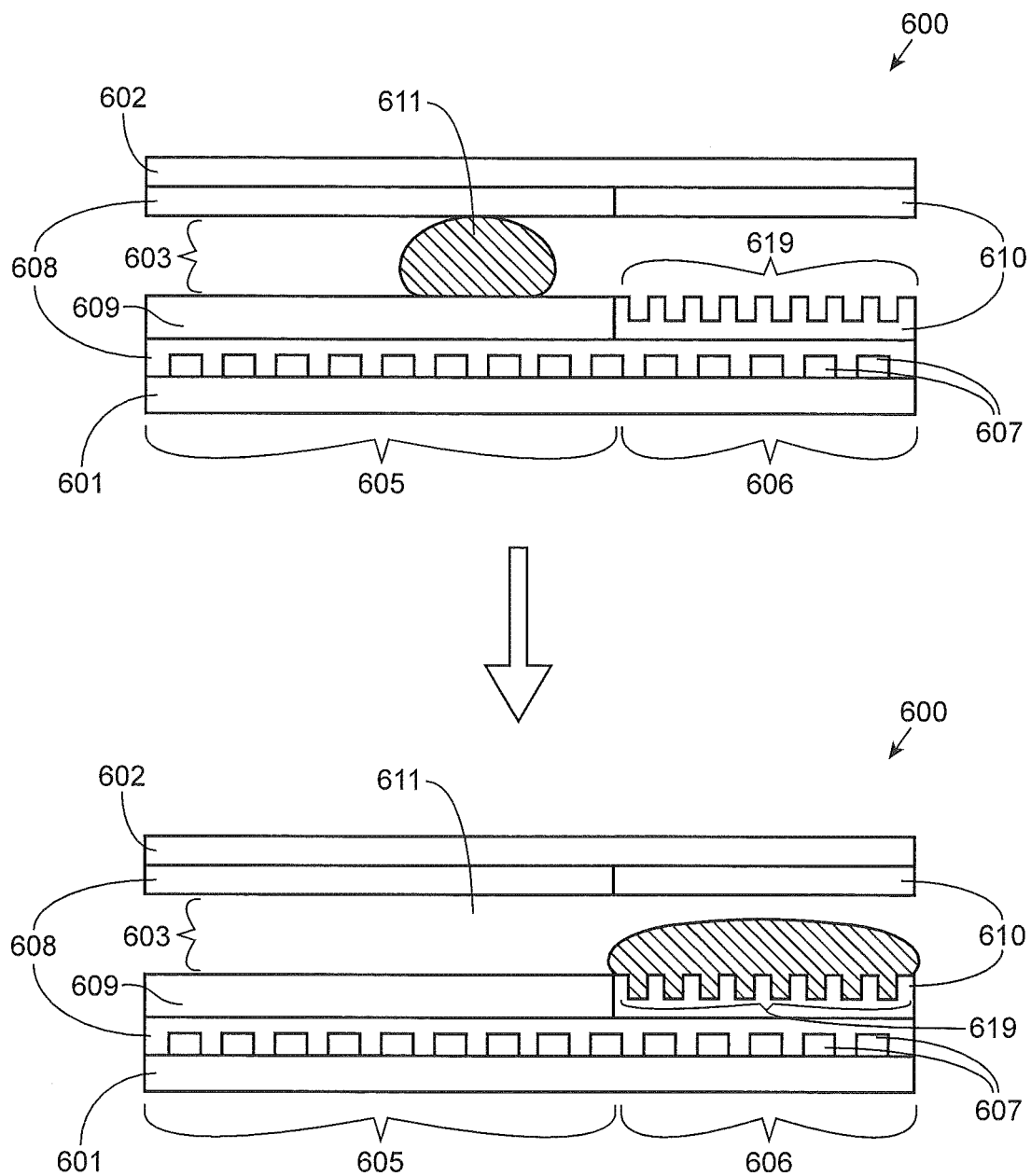
FIG. 6 illustrates an aqueous droplet being moved over the array of wells.

FIG. 6 depicts another embodiment of an integrated digital microfluidics and detection module. The device 600 includes a bottom layer 601 over which an array of electrodes 607 is formed. The array of electrodes is covered by a dielectric layer 608. A hydrophobic layer 609 is disposed only in the proximal portion 605 of the bottom substrate. A hydrophilic layer 610 is disposed on the distal portion 606 of the bottom substrate 601. An array of wells is located in the distal portion in the hydrophilic layer 610. A top substrate 602 separated from the bottom substrate by a gap/space 603 is also depicted. The top substrate 602 includes a dielectric layer 608 disposed on a bottom surface of the top substrate over the proximal portion of the bottom substrate. The top substrate includes a hydrophilic layer 610 disposed on a bottom surface of the top substrate across from the proximal portion of the bottom substrate. An aqueous droplet 611 does not wet the hydrophobic layer and upon reaching the hydrophilic distal portion the droplet 611 spreads over the array of wells 619, thereby facilitating movement of the aqueous phase via passive capillary forces. In a similar manner, the above concept may be reversed to facilitate wetting and spreading of an organic-based immiscible fluid over the wells. In this case, the top and bottom substrate on the distal portion can be coated with a hydrophobic material/coating, thereby allowing an organic-based immiscible fluid to flow over the wells via passive capillary forces.

As used herein, digital microfluidics refers to use of an array of electrodes to manipulate droplets in a microfluidics device, e.g., move droplets, split droplets, merge droplets, etc. in a small space. As used herein, the terms "droplet(s)" and "fluidic droplet(s)" are used interchangeably to refer to a discreet volume of liquid that is roughly spherical in shape and is bounded on at least one side by a wall or substrate of a microfluidics device. Roughly spherical in the context of the droplet refers to shapes such as spherical, partially flattened sphere, e.g., disc shaped, slug shaped, truncated sphere, ellipsoid, hemispherical, or ovoid. The volume of the droplet in the devices disclosed herein may range from about 10 □l to about 5 pL, such as, 10 µl-1 pL, 7.5 µl-10 pL, 5 µl-1 nL, 2.5 µl-10 nL, or 1 µl-100 nL, e.g., 10 µl, 5 µl, 1 µl, 800 nL, 500 nL, or lesser.

In some examples, the array of wells includes a plurality of individual wells. The array of wells may include a plurality of wells that may range from $10^9$ to 10 in number per 1 $mm^2$. In certain cases, an array of about 100,000 to 500,000 wells (e.g., femtoliter wells) covering an area approximately 12 $mm^2$ may be fabricated. Each well may measure about 4.2 µm wide×3.2 µm deep (volume approximately 50 femtoliters), and may be capable of holding a single bead/particle (about 3 µm diameter). At this density, the femtoliter wells are spaced at a distance of approx. 7.4 µm from each other. In some examples, the nanowell array may be fabricated to have individual wells with a diameter of 10 nm to 10,000 nm.

The placement of single nanobeads/nanoparticles/analyte molecules in the wells allows for either a digital readout or analog readout. For example, for a low number of positive wells (<~70% positive) Poisson statistics can be used to quantitate the analyte concentration in a digital format; for high numbers of positive wells (>~70%) the relative intensities of signal-bearing wells are compared to the signal intensity generated from a single nanobead/nanoparticle/analyte molecule, respectively, and used to generate an analog signal. A digital signal may be used for lower analyte concentrations, whereas an analog signal may be used for higher analyte concentrations. A combination of digital and analog quantitation may be used, which may expand the linear dynamic range. As used herein, a "positive well" refers to a well that has a signal related to presence of a nanobead/nanoparticle/analyte molecule, which signal is above a threshold value. As used herein, a "negative well" refers to a well that may not have a signal related to presence of a nanobead/nanoparticle/analyte molecule. In certain embodiments, the signal from a negative well may be at a background level, i.e., below a threshold value.

The wells may be any of a variety of shapes, such as, cylindrical with a flat bottom surface, cylindrical with a rounded bottom surface, cubical, cuboidal, frustoconical, inverted frustoconical, or conical. In certain cases, the wells may include a sidewall that may be oriented to facilitate the receiving and retaining of a nanobead or nanoparticle present liquid droplets that have been moved over the well array. In some examples, the wells may include a first sidewall and a second sidewall, where the first sidewall may be opposite the second side wall. In some examples, the first sidewall is oriented at an obtuse angle with reference to the bottom of the wells and the second sidewall is oriented at an acute angle with reference to the bottom of the wells. The movement of the droplets may be in a direction parallel to the bottom of the wells and from the first sidewall to the second sidewall.

In some examples, the array of wells can be fabricated through one or more of molding, pressure, heat, or laser, or a combination thereof. In some examples, the array of wells may be fabricated using nanoimprint/nanosphere lithography.

Figure 7A:
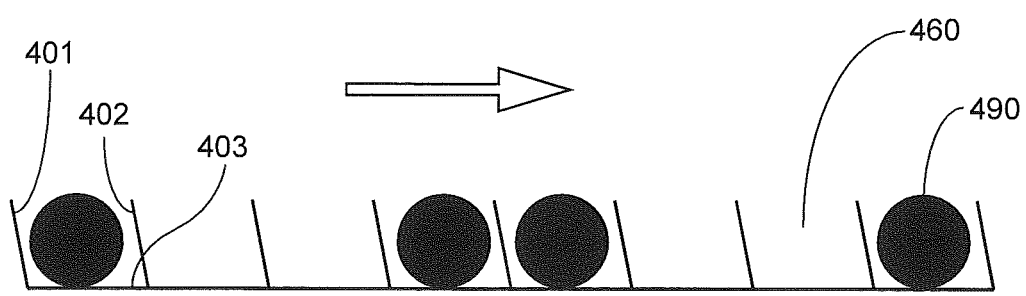
FIGS. 7A and 7B illustrate various exemplary orientations of the sidewalls of the wells.
Figure 7B:
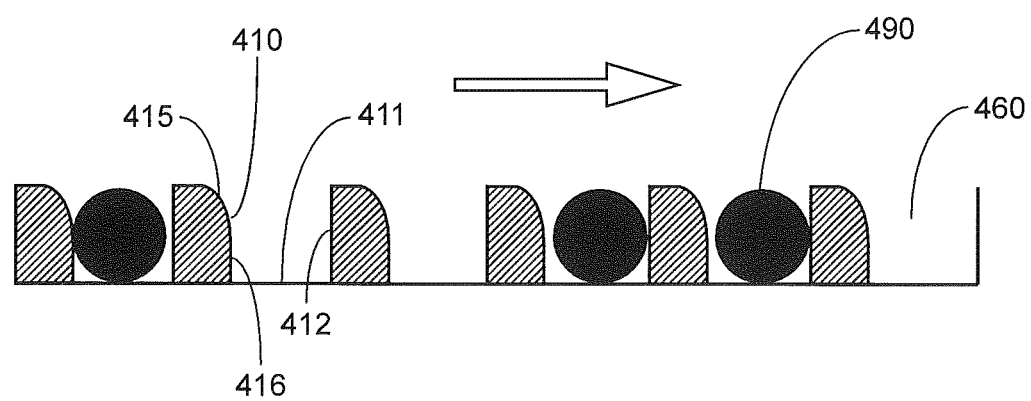

FIGS. 7A-7B illustrate several exemplary sidewall orientations of the wells. As illustrated in FIGS. 7A-B, the wells comprise a first sidewall opposite to a second sidewall. FIG. 7A illustrates a vertical cross-section showing individual wells 460 in the array of wells. FIG. 7A illustrates a first sidewall 401 and a second sidewall 402. The first side wall is at an obtuse angle with reference to a bottom surface 403 of the well and the second side wall is at an acute angle with reference to a bottom surface 403 of the well. The arrow illustrates the direction in which a liquid droplet moves across the array. This orientation of the sidewalls of the wells facilitates receiving and retaining nanobeads/nanoparticles/analyte molecules 490.

In FIG. 7B, a top portion 415 of the first sidewall 410 is oriented at an obtuse angle with reference to a bottom 412 of the wells and a bottom portion 416 of the first sidewall 410 is oriented perpendicular to the bottom 412 of the wells, and the second sidewall 411 is oriented perpendicular to the bottom 412 of the wells, where movement of liquid droplets is in a direction parallel to the bottom of the wells and from the first sidewall to the second sidewall, where the top portion of the first sidewall is at an opening of the wells.

The integrated devices described herein may be fabricated by a number of methods. In certain cases, the methods may involve a combination of laser ablation, spray coating, roll to roll, and nanoimprint lithography (NIL) to construct the first substrate, series of electrode, dielectric layer and hydrophobic layer.

In some examples, a plurality of rollers may unwind a first roll to drive the first substrate to a first position. A conductive material may then be applied to the first substrate. The conductive material may be patterned into a series of electrodes. In some examples, the printer device comprising one or more coating rollers to apply the at least one of the hydrophobic or the dielectric material to the at least one electrode pattern on the first substrate. In some examples, the coating rollers are to apply an anti-fouling material to the first substrate.

In some examples, the system further comprises a merger to align the first substrate with the second substrate. In some examples, the merger comprises two rollers. Also, some of the disclosed examples include a curing station to cure the hydrophobic material or the dielectric material. Some of the disclosed examples also include a bonding station to bond at least a first portion of the first substrate with at least a first portion of the second substrate. The bonded portions include the electrode pattern. The method also includes associating the first substrate and the second substrate at a spaced apart distance. The space between the first and second substrates may be about 0.01 mm to 1 mm in height, e.g., 1 µm, 5 µm, 10 µm, 20 µm, 50 µm, 100 µm, 200 µm, 300 µm, 400 µm, 500 µm, 1 µm-500 µm, 100 µm-200 µm, etc.

In some examples, the method includes embossing the first substrate to create one or more projections on the first substrate. In such examples, the projections are to separate the first substrate and the second substrate at the spaced apart distance.

The devices of the present disclosure may be operated manually or automatically or semiautomatically. In certain cases, the devices may be operated by a processor that runs a program for carrying out the steps required for generating an analyte related signal and detecting the signal. As used hereon, the phrase "analyte related signal" or "analyte associated signal" refers to a signal that is indicative of presence of an analyte and is proportional to the amount of the analyte in a sample. The signal may be fluorescence, chemiluminescence, colorimetric, turbidimetric, etc, in certain cases, the read out may be digital, for example, the number of positive counts (e.g., wells) is compared to the number of negative counts (e.g., wells) to obtain a digital count.

Figure 8:
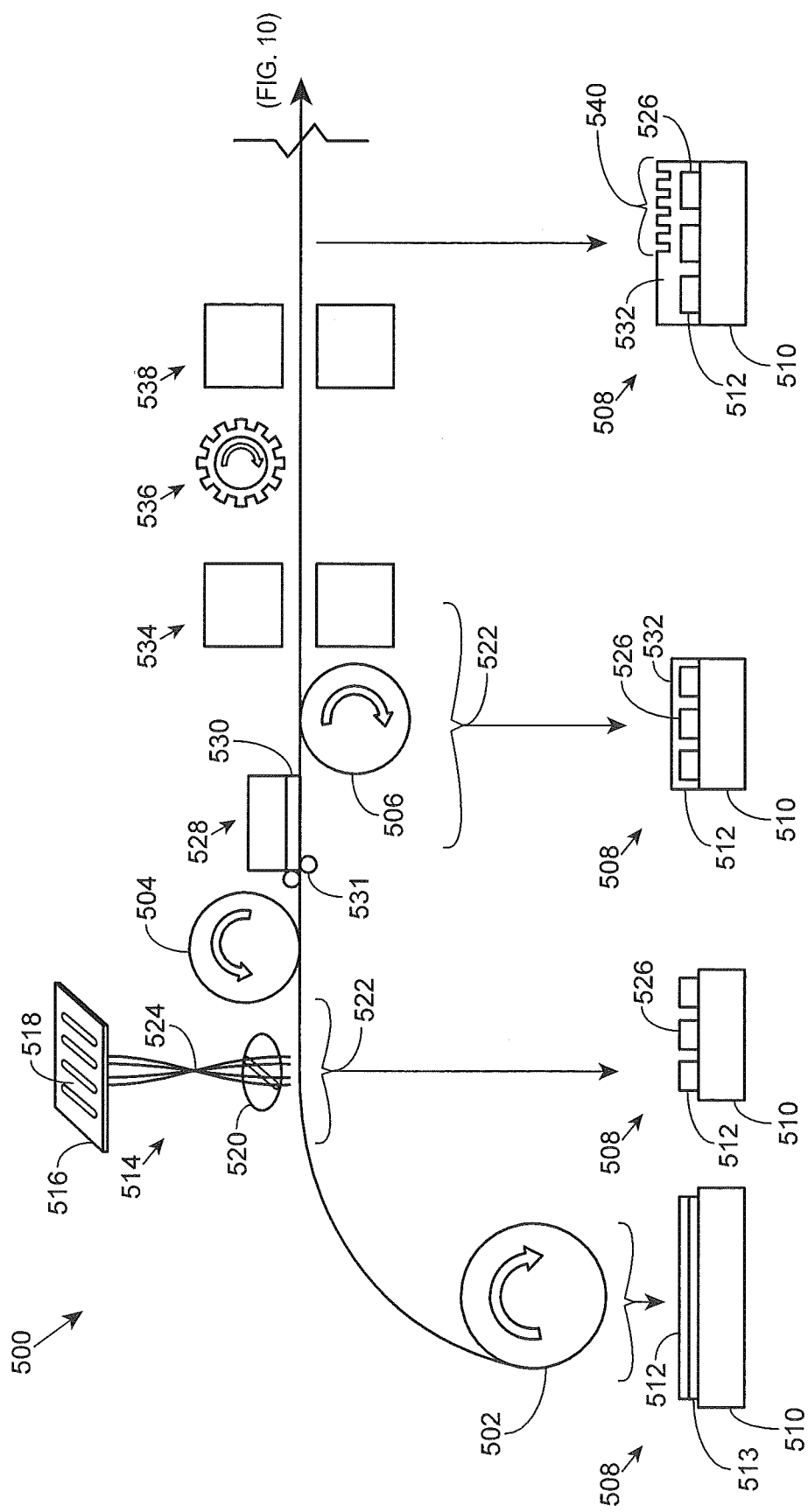
FIG. 8 illustrates an example of fabricating a bottom substrate of the digital microfluidic and analyte detection device.

FIG. 8 is a diagram of a first exemplary system or assembly 500 for creating a base substrate of an integrated digital microfluidics and analyte detection device. The first example assembly 500 includes a series or a plurality of rollers, including a first roller 502, a second roller 504, and a third roller 506, which operate in synchronized rotation to drive a base substrate 508 through the first example assembly 500. The first example assembly 500 can include rollers in addition to the first through third rollers 502, 504, 506 to move the base substrate 508 through the assembly using roll-to-roll techniques. Other examples may use conveyors, pulleys and/or any other suitable transport mechanism(s).

In the first example assembly 500, the first roller 502 rotates to unwind the base substrate 508, which, in some examples, is a single sheet in a rolled configuration. The base substrate 508 includes a first layer 510 and a second layer 512. In this example, the first layer 510 comprises a non-conductive flexible substrate or web, such as for example a plastic, and the second layer 512 includes a conductive material. The conductive material of the second layer 512 can be, for example, a metal such as gold, silver, or copper, or a non-metallic conductor, such as a conductive polymer. In other examples different metal(s) or combination(s) of metal(s) and/or conductive polymer(s) may be used. In some examples, the base substrate 508 includes an adhesive layer 513 disposed between the non-conductive first layer 510 and the conductive second layer 512. As an example, the adhesive layer 513 can comprise chrome, with a layer of gold disposed on top of the chrome adhesive layer 513 to form the conductive second layer 512. Thus, in the base substrate 108 of FIG. 5, the non-conductive first layer 510 and the conductive second layer 512 are pre-adhered to form the base substrate 508 prior to being unwound by the first roller 502.

In the example base substrate 508 of FIG. 8, the non-conductive first layer 510 has a thickness of less than about 500 nm. As will be described below, such a thickness allows for the base substrate 508 to move through the example first assembly 500 via the plurality of rollers. Also, in some examples, the thickness of the nonconductive first layer 510 is greater than a thickness of the conductive second layer 512. As an example, the thickness of the conductive second layer 512 can be approximately 30 nm. In other examples, the thickness of the conductive second layer 512 is less than about 500 nm. In some examples, the thickness of the non-conductive first layer 510 and/or the conductive second layer 512 is selected based on, for example, the materials of the first and/or second layers 510, 512 and/or an operational purpose for which the droplet actuator formed from the base substrate 508 is to be used.

The first roller 502 drives the base substrate 508 to a laser ablation station 514. The laser ablation station 514 includes a mask 516 containing a master pattern 518 that is to be projected onto the conductive second layer 512 of the base substrate 108. The master pattern 518 associated with the mask 516 may be predefined based on characteristics such as resolution (e.g., number of electrodes per an area of the base substrate 508 to be ablated), electrode size, configuration of lines defining the electrode pattern, inter-digitation of the electrodes, gaps or spacing between the electrodes, and/or electrical traces for connecting the electrodes to an instrument, such as, a power source. In some examples, the characteristics of the master pattern 518 are selected based on one or more operational uses of the droplet actuator with which the base substrate 508 is to be associated (e.g., for use with biological and/or chemical assays). Also, in some examples, the master pattern 518 is configurable or reconfigurable to enable the laser ablation station 514 to form different patterns on the base substrate 508. Additionally or alternatively, in some examples the mask 516 is replaceable with one or more alternative masks.

The laser ablation station 514 includes a lens 520. As the base substrate 508 encounters the laser ablation station 514 as result of the rotation of the rollers (e.g., the first roller 502), a portion 522 of the base substrate 508 passes under or past the lens 520. The portion 522 may be, for example, a rectangular or square section of the base substrate 508 having an area less than the area of the base substrate 508 and including the conductive second layer 512. The lens 520 images or projects at least a portion of the master pattern 518 onto the conductive second layer 512 associated with the portion 522. A laser beam 524 is directed onto the portion 522 via the mask 516 and the lens 520 such that the laser beam 524 selectively penetrates the conductive second layer 512 based on the projected master pattern 518. In some examples, the non-conductive first layer 500 or a portion (e.g., a fraction of the thickness of the non-conductive first layer 510) may also be penetrated by the laser beam 524 based on the projected master pattern 518. The solid portions of the mask 516 block the laser beam 524, and the open portions of the mask 516 allow the laser beam 524 to pass through the mask 516 and into contact with the base substrate 508. The laser beam 524 can be associated with, for example, an excimer laser.

As a result of exposure to the laser beam 524, the irradiated nonconductive first layer 510 of the portion 522 absorbs energy associated with the laser beam 524. The irradiated non-conductive first layer 510 undergoes photochemical dissociation, resulting in a selective breaking up of the structural bonds of nonconductive first layer 510 and ejection of fragments of the non-conductive first layer 510 and portions of the conductive second layer 512 overlaying the irradiated non-conductive first layer 510 in accordance with the master pattern 518. In some examples, a depth (e.g., a radiation intensity) to which the laser beam 524 penetrates the base substrate 508 is predefined based on a depth (e.g., a thickness) of the non-conductive first layer 510 and/or the conductive second layer 512. In some examples, the laser beam 524 penetration depth is adjustable to change the depth at which the laser beam 524 ablates the conductive second layer 512 as a result of the fragmentation of the underlying nonconductive first layer 510. In some examples, this adjustment is dynamic as the example system 500 operates. Also, in some examples, the base substrate 508 undergoes cleaning after exposure to the laser beam 524 to remove particles and/or surface contaminants.

As illustrated in FIG. 8, after exposure to the laser ablation station 514, the portion 522 of the base substrate 508 includes an electrode array 526. The electrode array 526 is made up of a plurality of electrodes formed into the conductive second layer 512. As a result of the exposure to the laser beam 524 and fragmentation of the non-conductive first layer 510, portions of the conductive second layer 512 are removed from the base substrate 508. The removed portions associated with the electrode array 526 are based on the master pattern 518. In some examples, the removed portions match the open portions of the mask 516.

Returning to FIG. 8, after the portion 522 undergoes laser ablation at the laser ablation station 514 to form the electrode array 526, the portion 522 is moved, via rotation of the first through third rollers 502, 504, 506, to a printer 528. In the first example assembly 500, the printer 528 includes an apparatus or an instrument capable of applying at least one layer of material 530 having a hydrophobic and/or a dielectric property to the electrode array 526. In the first example assembly 500, the printer 528 can deposit the hydrophobic and/or dielectric material 530 via deposition techniques including, but not limited to, web-based coating (e.g., via rollers associated with the printer 528), slot-die coating, spin coating, chemical vapor deposition, physical vapor deposition, and/or atomic layer deposition. The printer 528 can also apply other materials in addition to the hydrophobic and/or dielectric material 530 (e.g., anti-fouling coatings, anti-coagulants). Also, the printer 528 can apply one or more layers of the material(s) with different thicknesses and/or covering different portions of the base substrate 508.

As described above, in the first example assembly 500, at least one of the first through third rollers 502, 504, 506 advance the base substrate 508 to the printer 528 for application of the hydrophobic and/or dielectric material 530 to the electrode array 526. In some examples, the printer 528 includes a plurality of registration rollers 531 to facilitate accuracy in feeding and registration of the base substrate 508 as part of operation of the printer 528 in applying the hydrophobic and/or dielectric material 530, for example, via roller coating methods.

In the first example assembly 500, the hydrophobic and/or dielectric material 530 is applied to the electrode array 526 to completely or substantially completely insulate the electrode array 526.

In some examples, the hydrophobic and/or dielectric material 530 is deposited via the printer 528 in substantially liquid form. To create a structural or treated layer 532 on the base substrate 508 to support a droplet, the portion 522 is moved via the rollers (e.g., the first through third rollers 502, 504, 506) through a curing station 534. At the curing station 534, the hydrophobic and/or dielectric material is treated and/or modified to form the first treated layer 532. Treating and/or modifying the hydrophobic and/or dielectric material can include curing the material. For example, at the curing station 534, heat is applied to facilitate the hardening of the hydrophobic and/or dielectric material 530. In some examples, the portion 522 is exposed to an ultraviolet light to cure the hydrophobic and/or dielectric material 530 and form the treated layer 532 to insulate the electrode array 526. In other examples, the curing and/or modification of the hydrophobic and/or dielectric material is accomplished without heat and/or a photon source. In some examples, the treated layer 532 supports a droplet as an electric field is applied (e.g., in connection with electrode array 526) to manipulate the droplet. For example, during an electrowetting process, a contact angle of the droplet with respect to the treated layer 532 changes as a result of an applied voltage, which affects the surface tension of the droplet on the treated surface 532. Electrowetting is merely exemplary, the droplet may be moved using other forces as well.

After passing through the curing station 534, the portion 522 is prepared to serve as a bottom substrate of a droplet actuator and/or as a digital microfluidic chip. Because the base substrate 508 includes the non-conductive first layer 510 bonded with the conductive second layer 512, as disclosed above, additional adhesion of, for example the electrode array 526 to the non-conductive first layer 510 is not required. Such a configuration increases the efficiency of the preparation of the base substrate 508 for the droplet actuator by reducing processing steps. Also, as described above, when the portion 522 is at any one of the laser ablation station 514, the printer 528, or the curing station 534, other portions of the base substrate 508 are concurrently moving through the others of the respective stations 514, 528, 534 of the first example assembly 500. For example, when the portion 522 is at the curing station 534, the first through third rollers 502, 504, 506 are continuously, periodically, or aperiodically advancing one or more other portions n of the base substrate 508 through, for example, the laser ablation station 514 and/or the printer 528. In such a manner, preparation of the base substrate 508 for the droplet actuator is achieved via a substantially continuous, high-speed, automated process.

After the curing step, a pattern roller 536 is rolled over a distal portion of the base substrate and cured in the curing station 538 to create an array of wells 540. The array wells 540 may subsequently be coated with a hydrophilic material (not shown).

Although the base substrate 508 may be considered as including successive portions, during some example operations of the first example assembly 500, the base substrate 508 remains as a single sheet as the successive portions undergo processing to create the electrode arrays 526 (e.g., via the electrode pattern) and receive the coating of hydrophobic and/or dielectric material 530. Thus, to create one or more droplet actuators using the processed base substrate 508, the base substrate 508, in some examples, is cut (e.g., diced) to form individual units comprising the electrode arrays 526, as will be further disclosed below. In some examples, prior to dicing, the base substrate 508, including the portion 522, is rewound in a rolled configuration similar to the initial rolled configuration of the base substrate 508 prior to being unwound by the first roller 502. Such rewinding may be accomplished via one or more rollers as part of the roll-to-roll processing. In such examples, the base substrate 508 may be diced or otherwise separated at a later time. In other examples, the rollers (e.g., the second and third rollers 504, 506), advance the base substrate 508 for merging with a top substrate.

Figure 9:
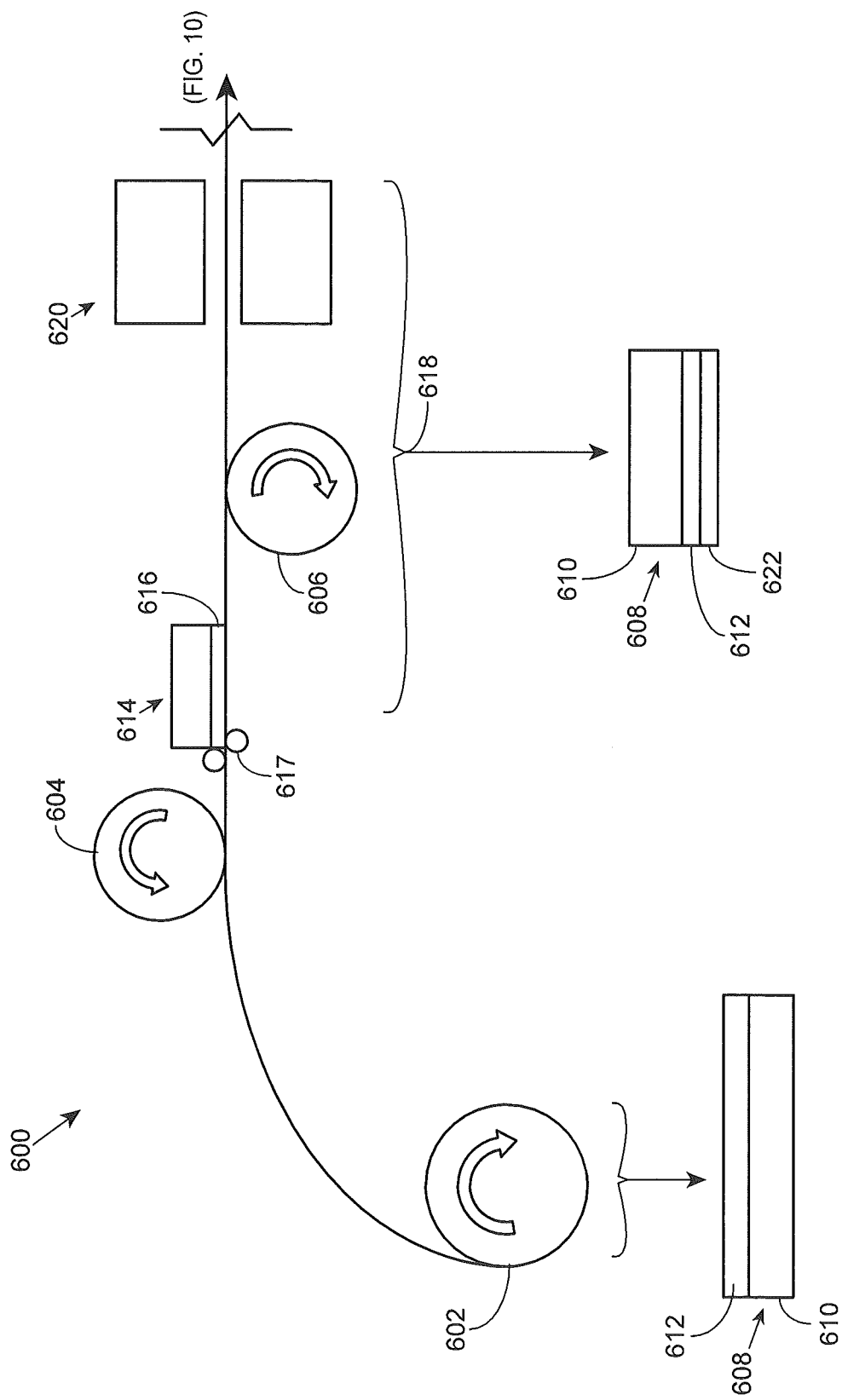
FIG. 9 illustrates an example of fabricating a top substrate of the digital microfluidic and analyte detection device.

FIG. 9 illustrates a second example assembly 600 for creating an example top substrate of a droplet actuator having a single electrode. The second example assembly 600 includes a series or a plurality of rollers, including a first roller 602, a second roller 604, and a third roller 606, which operate in synchronized rotation to drive a top substrate 608 through the second example assembly 600. The second example assembly 600 can include rollers in addition to the first through third rollers 602, 604, 606 to move the top substrate 608 through the assembly 600.

In the second example assembly 600, the first roller 602 rotates to unwind the top substrate 608, which, in some examples, is a sheet in a rolled configuration. The example top substrate 608 of FIG. 9 includes a first layer 610 and a second layer 612. As with the example base substrate 508, in this example, the example first layer 610 of the top substrate 608 comprises a non-conductive material such as, for example, a plastic, and the example second layer 612 includes a conductive material, such as a metal including, for example, one or more of gold, chrome, silver, indium tin oxide, or copper and/or any other suitable metal(s), conductive polymer(s), or combination(s) of metal(s) and/or conductive polymer(s). In some examples, the conductive second layer 612 is adhered to the nonconductive first layer via an adhesive layer (e.g., chrome).

In the second example assembly 600, the first through third rollers 602, 604, 606 rotate to advance the top substrate 612 to a printer 614. The printer 614 coats the conductive second layer 612 with a hydrophobic and/or dielectric material 616 (e.g. Teflon® or parylene C, or a dielectric such as a ceramic). The printer 614 is substantially similar to the printer 528 of the first example assembly 500 of FIG. 8. For example, the printer 614 can apply the hydrophobic and/or dielectric material 616 to the top substrate 608 via web-based coating, slot-die coating, spin coating, chemical vapor deposition, physical vapor deposition, atomic layer deposition, and/or other deposition techniques. The printer 614 can include registration rollers 617 to facilitate alignment of the top substrate 608 with respect to the printer 614 during application of the hydrophobic and/or dielectric material 616 and/or other coating materials.

After receiving the coating of the hydrophobic and/or dielectric material 616, the second roller 504 and the third roller 506 advance the portion 618 to a curing station 620. As disclosed in connection with the curing station 534 of FIG. 8, the curing station 620 of the second example assembly 600 facilitates the modification (e.g., curing) of the hydrophobic material via heat to form a treated layer 622. The treated layer 622 insulates the conductive second layer 612, which serves as the single electrode of the top substrate 608, by completely or substantially completely covering the conductive second layer 612. Thus, in coating the second layer 612 of the portion 618, electrical potential conducting portion of the top substrate 608 is insulated from a droplet that may be applied to a droplet actuator that includes the portion 618.

After passing through the curing station 620, the portion 618 is prepared to serve as a top substrate of a droplet actuator. Because the top substrate 608 includes the non-conductive first layer 610 pre-adhered to the conductive second layer 612, additional adhesion of, for example, an electrode to the non-conductive first layer 610 is not required, thereby increasing the efficiency of the preparation of the top substrate 608 for the droplet actuator.

In the second example assembly 600, the first through third rollers 602, 604, 606 rotate to advance the top substrate 608 such that portions of the top substrate pass through one of the printer 614 or the curing station 620 in substantially continuous, periodic and/or aperiodic succession as part of the roll-to-roll operation of the second example assembly 60. Thus, although the second example assembly 600 is described in association with the portion 618, it is to be understood that successive portions of the top substrate 608 are prepared in substantially the manner as the portion 618 as a result of rotation of the first through third rollers 602, 604, 606. In such as manner, the top substrate 308 is provided with a treated layer 622 along the length of the top substrate 608.

In the example top substrate 608, the conductive second layer 612 serves an electrode. However, in some examples, the conductive second layer 612 undergoes laser ablation to form one or more electrode arrays. In such examples, the second example assembly 600 includes a laser ablation station. Thus, prior to receiving the hydrophobic material 616, the top substrate 608 is exposed to a laser beam, which creates an electrode pattern in the irradiated conductive second layer 612. Also, in some examples, the electrode array is not formed on/in the base substrate but only on/in the top substrate 608.

During operation of the second example assembly 600, the top substrate remains single sheet as successive portions of the top substrate 608 are coated with the hydrophobic material 616. As part of the fabrication of one or more droplet actuators, the top substrate 608 is aligned with the base substrate. In some examples, after passing through the curing station 620, the top substrate is rewound into a rolled configuration via one or more rollers. In such examples, the finished roll may be diced or otherwise cut and/or separated into individual units that are aligned at a spaced apart distance and bonded with individual diced units of the base substrate to create a droplet actuator.

In other examples, after passing through the curing station 620, the rollers (e.g., the first through third rollers 602, 604, 606) continue to advance the top substrate 608 to merge the top substrate 608 with the base substrate via automated roll-to-roll processing. In such examples, to prepare the top substrate 608 for alignment with the base substrate 508, the first through third rollers 602, 604, 606 rotate so as to reverse the orientation of the top substrate relative to the base substrate such that the treated layer of the base substrate faces the treated layer 622 of the top substrate 608 when the base substrate 508 and the top substrate 608 are aligned in parallel configuration.

Figure 10:
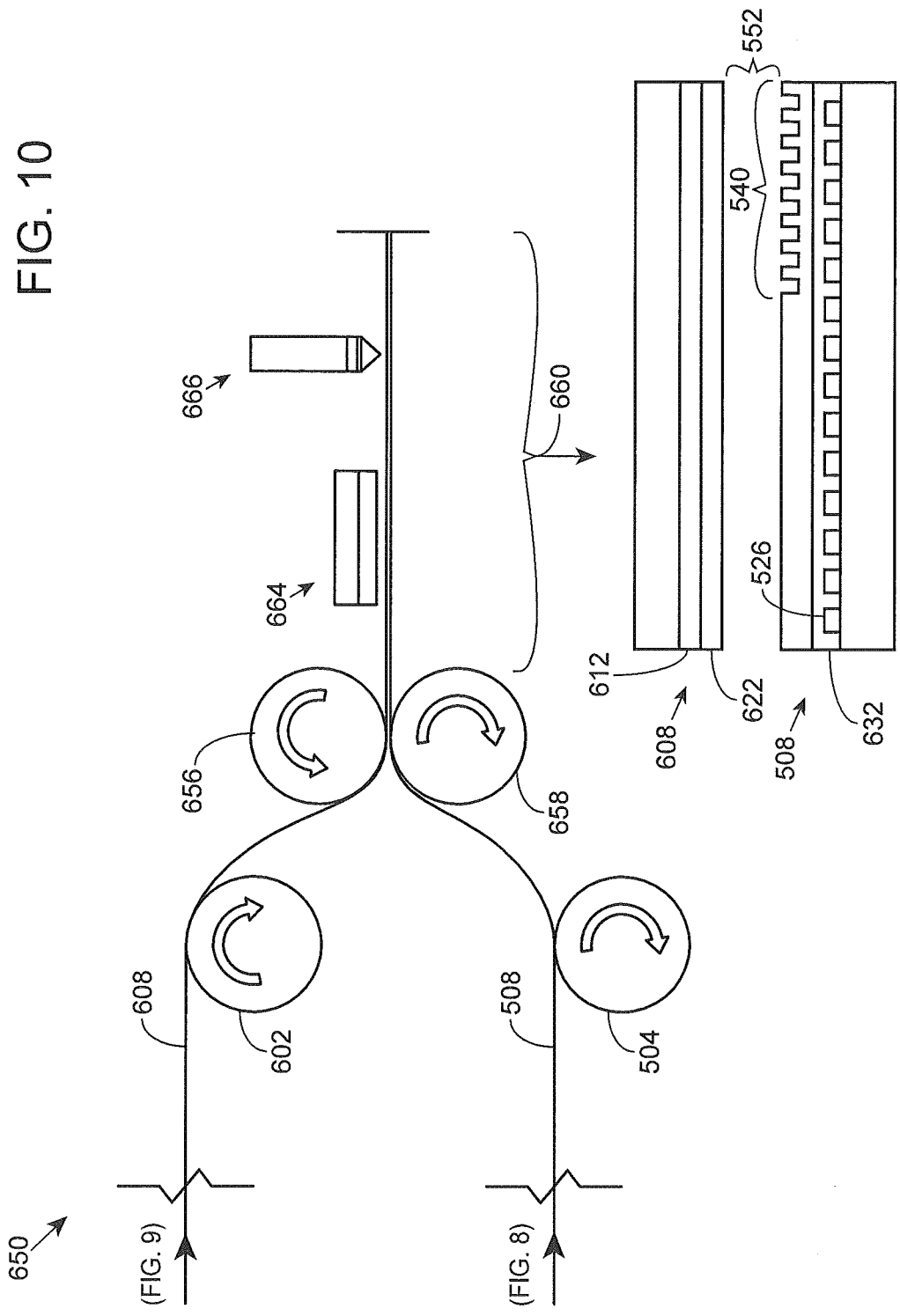
FIG. 10 illustrates an example of assembling the top and bottom substrates to manufacture a plurality of digital microfluidic and analyte detection devices.

As show in FIG. 10, the third example assembly 650 includes a third roller 656 and a fourth roller 608 that form a pair of merging rollers to which the base substrate 508 and the top substrate 608 are fed via the respective first roller 652 and the second roller 654 of the third example assembly 650. As each of the merging rollers 656, 658 rotates, the base substrate 658 and the top substrate 658 are aligned in a parallel configuration at a predetermined spaced apart distance, or gap. In the resultant device, the electrode array 526 is made up of a plurality of electrodes formed into the conductive second layer 632. The top substrate 608 and the base substrate 508 are separated by the gap 552.

The example third assembly 650 includes a bonding station 664. The bonding station 664 joins, or bonds, the base substrate 508 and the top substrate 608 as part of fabricating the droplet actuator. For example, at the bonding station 664, one or more adhesives may be selectively applied to a predefined portion of the base substrate 508 and/or the top substrate 608 (e.g., a portion of the base substrate 508 and/or the top substrate 608 defining a perimeter of the resulting droplet actuator) to create a bond between the base substrate 508 and the top substrate 608 while preserving the gap 662. In some examples, bonding the substrates 508, 608 at the bonding station 664 including forming the gap 662 (e.g., in advance of applying the adhesive).

Examples of adhesive(s) that may be used at the bonding station 664 include epoxies, foils, tapes, and/or ultraviolet curable adhesives. In some examples, layers of polymers such as SU-8 and/or polydimethylsiloxane (PDMS) are applied to the base substrate 508 and/or the top substrate 608 to bond the substrates. Also, in some examples, the bonding station 664 provides for curing of the adhesive(s) via, for example, ultraviolet light. The bonding station 664 may apply one more methods involving, for example, heat (e.g. thermal bonding), pressure, curing, etc. to bond the base substrate 658 and the top substrate 608.

In the example third assembly 650, the merged portion 660 can be selectively cut, diced or otherwise separated to form one or more droplet actuators, as substantially represented in FIG. 10 by the merged portion 660. The example third assembly 650 includes a dicing station 666. The dicing station 666 can be, for example, a cutting device, a splitter, or more generally, an instrument to divide the continuous merged portion 660 into discrete units corresponding to individual droplet actuators. The merged portion 660 may be cut into individual droplet actuators based on, for example, the electrode pattern such that each droplet actuator includes a footprint of the electrode array and the other electrodes that are formed via the electrode pattern.

Figure 11B:
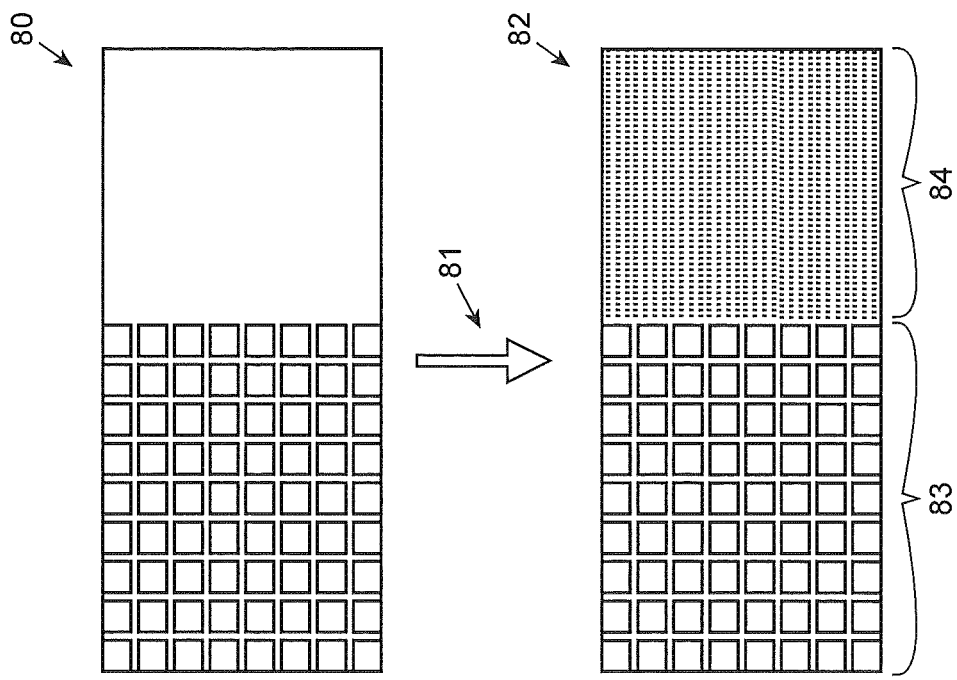
FIGS. 11A and 11B show a view from the top of a bottom substrate of exemplary digital microfluidic and analyte detection devices of the present disclosure.
Figure 11A:
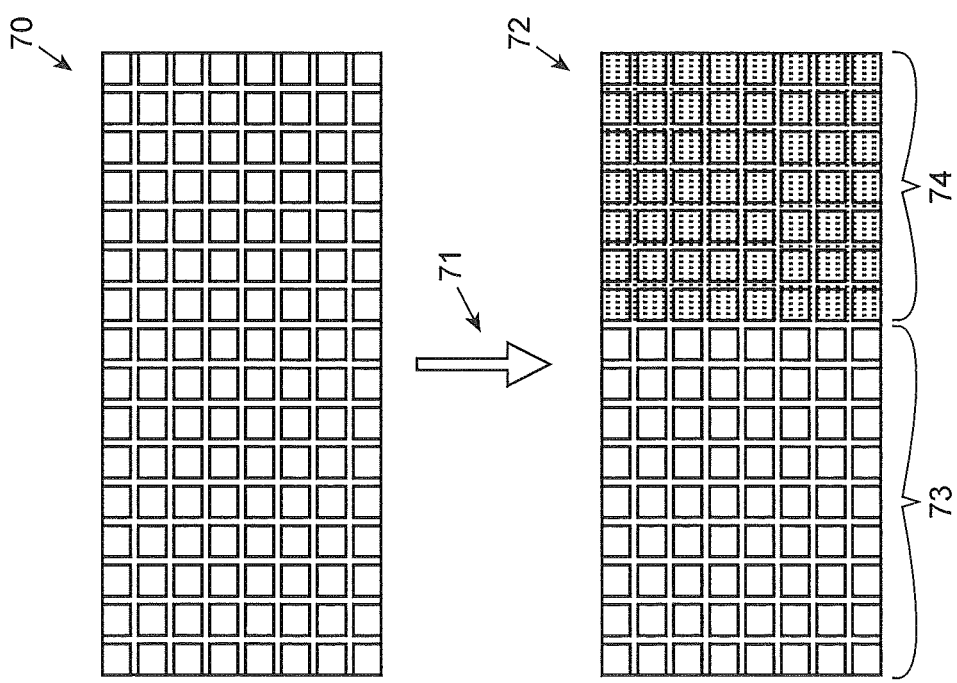

FIG. 11A depicts a top view of the bottom substrate 70 on which an array of electrodes is present in the proximal portion 73 and distal portion 74. The bottom substrate 72, after step 71 of fabrication of an array of wells on the distal portion, is shown. FIG. 11B depicts a top view of a bottom substrate 80 with an array of electrodes disposed only in the proximal portion 83. The bottom substrate 82 is depicted after the step 81 in which an array of wells is formed in the distal portion 84.

Figure 12A:
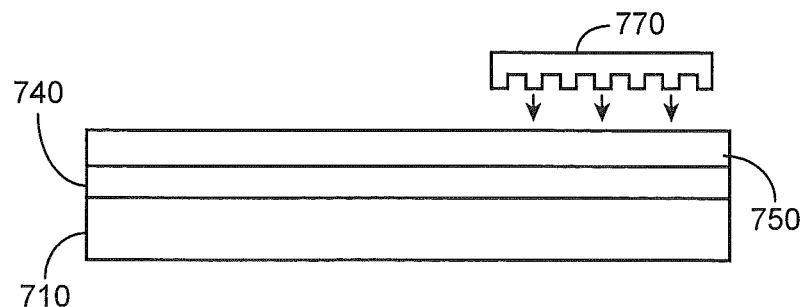
FIGS. 12A-12D illustrate examples of fabricating the array of wells into the integrated digital microfluidic and analyte detection device.

The nanowell array may be fabricated onto the dielectric/hydrophobic layer, hydrophobic layer (if present), or hydrophilic layer (if present). One exemplary method for fabricating a nanowell array onto the hydrophobic layer of the first substrate uses thermal or ultraviolet nanoimprint lithography. FIG. 12A illustrates one exemplary method for fabricating a nanowell array by utilizing a flat nanoimprint mold 770 to apply sufficient pressure to the hydrophobic layer 750 at the distal portion of the first substrate 710 in order to form the nanowell array 760 pattern. In this example, the nanoimprint stamper may be a flat stamping element whose stamping contours correspond to the upper surface of the second layer.

Figure 12B:
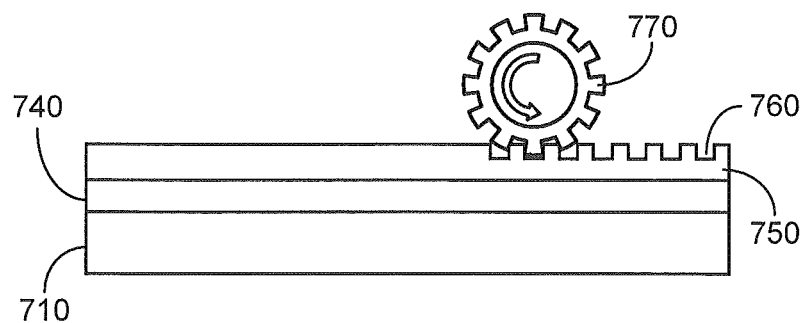

FIG. 12B illustrates another exemplary method in which a nanoimprint roller 775 may be utilized to apply the pattern of nanowell arrays to the hydrophobic layer of the distal portion of the first substrate. The nanoimprint roller may imprint the pattern onto the hydrophobic layer 750 of the first substrate 710 by advancing the roller 775 in one direction. As the roller advances in the one direction, the roller leaves behind an imprint of a pattern of the nanowell array 760 that corresponds to the imprint pattern on the roller. In one example, the roller 775 rolls in a counter clock-wise direction as the roller 775 imprints pattern onto the hydrophobic layer 750 of the first substrate 710. It is understood that the roller or stamper may be changed to form wells of suitable volume, for example, a femtolitre roller or stamper may be used for forming femtoliter wells.

Figure 12C:
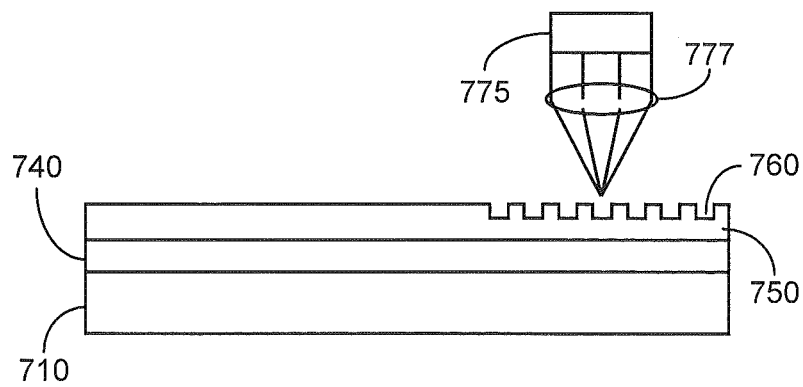

FIG. 12C illustrates another exemplary method of forming a pattern of nanowell arrays to the hydrophobic layer of the distal portion of the first substrate. In this example, a laser may be applied to ablate the upper surface of the hydrophobic layer 750. The laser ablation step can produce a nanowell array 760 pattern on the second layer. Some examples of suitable lasers for ablating the second layer include parameters with femtosecond and picosecond lasers. In some examples, the laser ablation step includes use of a special mask to define the nanowell array pattern required. In some examples, the laser 775 utilizes a focusing element 777 (e.g., lens) to accurately target and ablate the pattern. In some examples, following the laser ablation step, the nanowell array may be coated with a dielectric and/or hydrophobic layer.

Figure 12D:
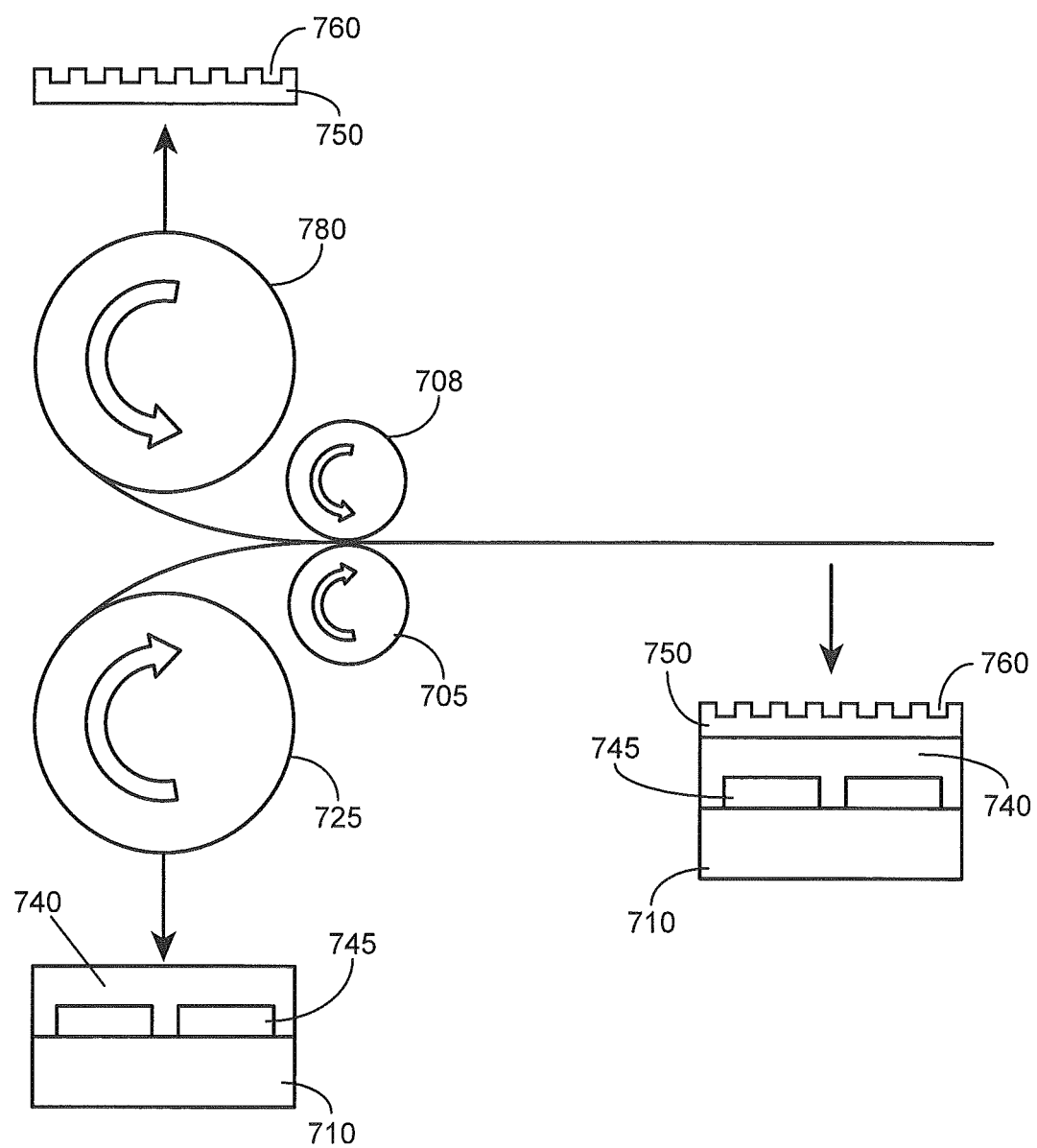

FIG. 12D illustrates yet another example of forming a pattern of nanowell arrays 760 onto the dielectric layer 740 of the distal portion of the first substrate 710. As illustrated in FIG. 12D, the method utilizes roll-to-roll fabrication to separately fabricate microfluidic component and the well array. In one example, a first roll 725 contains a microfluidic component, which includes the first substrate 710, where the first substrate comprises a series of electrodes 745, and a dielectric layer 740 disposed over the upper surface of the first substrate and covering the series of electrodes 745. A second roll 780 contains a substrate 750 with the pattern of well array 760 already included on the substrate. In some examples, the pattern of well array 760 previously included on the substrate 750 can be applied through thermal or UV nanoimprint lithography. In other examples, the pattern of nanowell array can be previously included on the substrate through laser ablation. As illustrated in FIG. 12D, the imprinted second roll 780 may also include a hydrophobic coating imprinted onto the substrate of the well array. The separate rolls are unwound via rollers 705 and 708, and then subject to a lamination process where the two films may be laminated together by overlying the nanowell substrate over the microfluidic component substrate to form a stacked configuration of the well array and microfluidic components.

As described herein, "roll-to-roll" may include the equivalent term "reel-to-reel" (R2R) and operates by moving a substrate through various components at high speeds, including, for example, rates of meters per second. Roll-to-roll assemblies facilitate the unwinding of a rolled substrate, the advancement of the substrate through the components, and the rewinding of the processed substrate into a roll.

As previously noted, the detection module formed by the distal portions of the first and second substrates is used for detecting an analyte related signal. In some examples, detection of the analyte or biological sample of interest may occur through optical signal detection. For example, shining an excitation light (e.g., laser) in order to measure the signal intensity result, in other examples, the analyte desired may be detected by measuring an optical signal emanating from each well chamber and quantified by quantifying the result. For example, the number of positive counts (e.g., wells) is compared to the number of negative counts (e.g., wells) via digital analysis. A variety of signals from the wells of the device may be detected. Exemplary signals include fluorescence, chemiluminescence, colorimetric, turbidimetric, etc.

Figure 15:
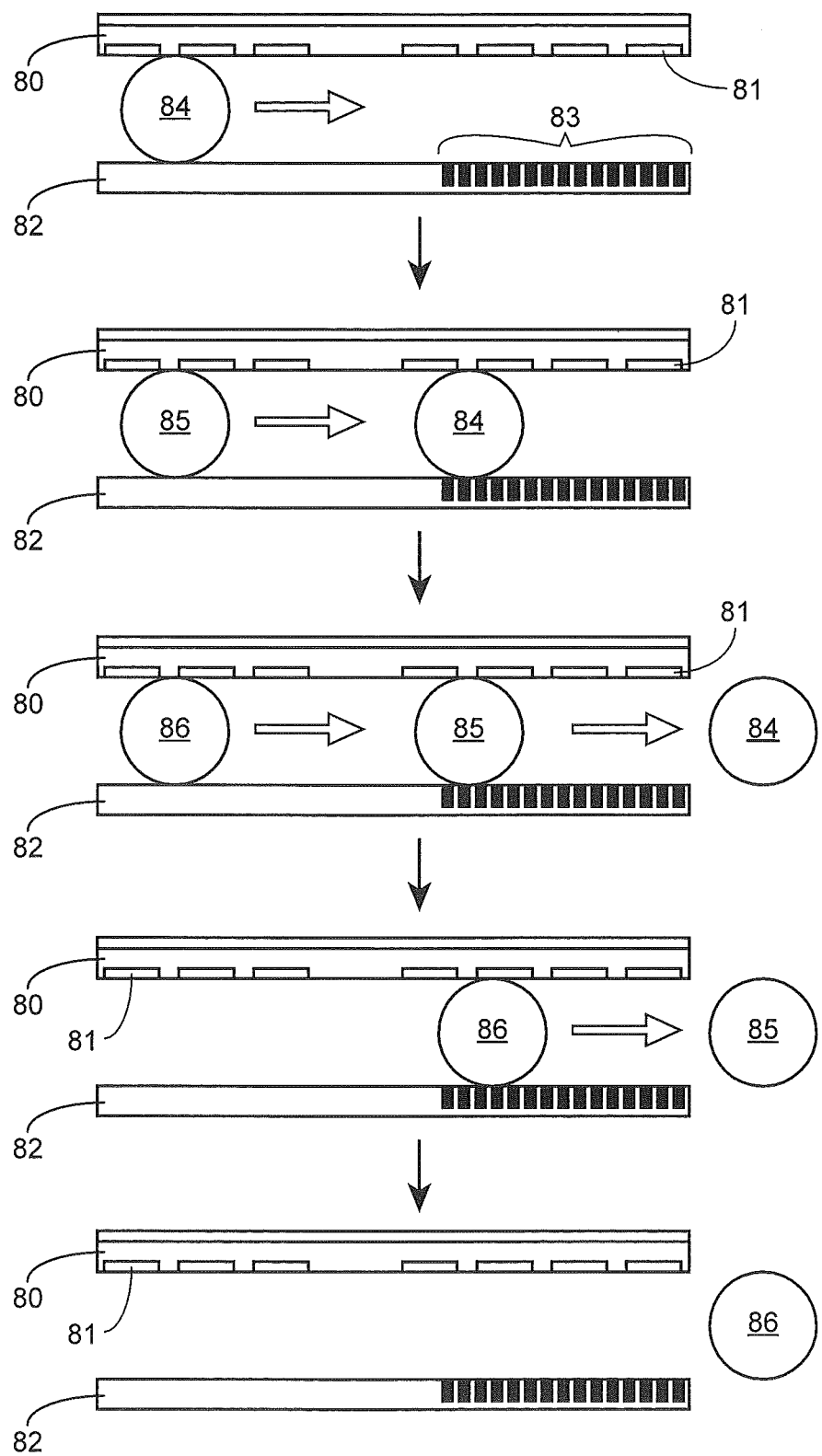
FIG. 15 depicts an exemplary method of the present disclosure.

The devices described herein may be used to generate an analyte related signal and quantitate the signal. Exemplary method is depicted in FIG. 15. The device in FIG. 15 includes a top substrate 80 with an array of electrodes 81. The top substrate is positioned in a spaced apart manner from the bottom substrate 82 which includes an array of wells 83 in a distal portion of the device. A droplet 84 containing particles or beads or analyte molecules (not shown) may be moved to the array of wells 83 using the electrodes 81. After a sufficient period of time to allow the particles or beads or analyte molecules to move into the wells, the droplet 84 may be moved to a waste chamber/absorption pad and the like. A droplet of buffer 85 may then be moved to the array of wells to remove any particles or beads not deposited into the wells. In some cases, the buffer droplet may push the droplet 84 over to the waste chamber. A droplet of immiscible fluid 86 may be moved over the array of wells and seal the wells. Any excess droplet 86 may be removed prior to optically interrogating the wells.

Figure 16:
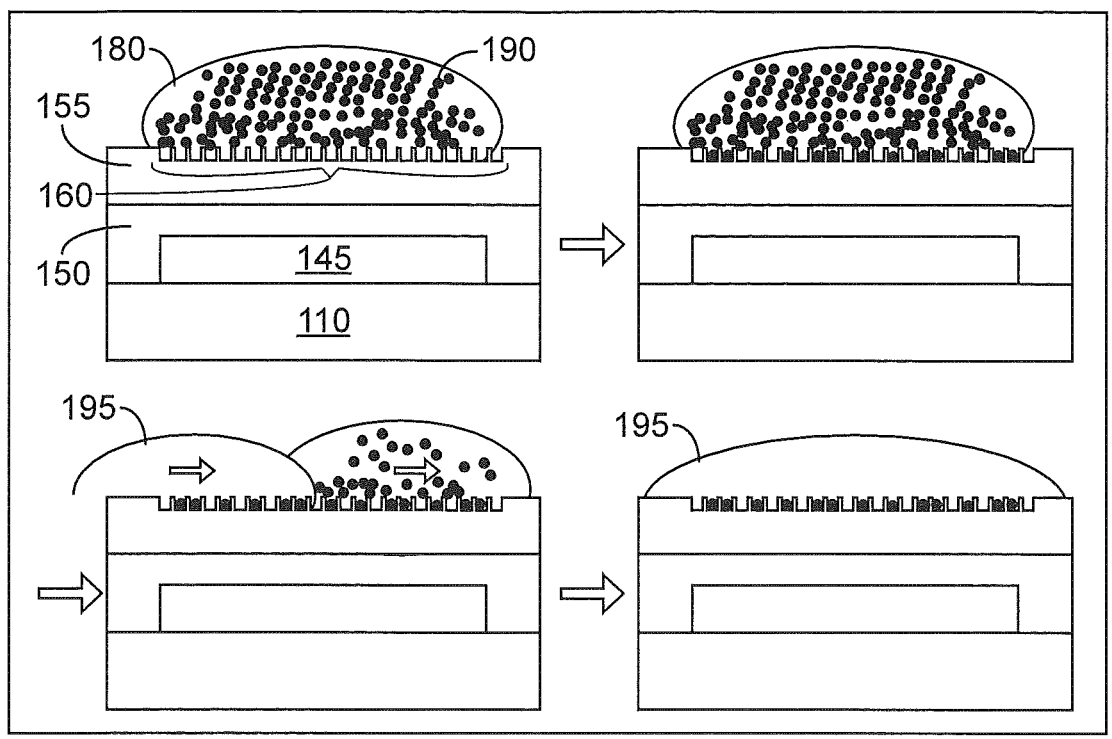
FIG. 16 illustrates an exemplary method for removing beads not located in the wells of the depicted device.

FIG. 16 depicts a method in which the digital microfluidics electrodes (e.g. electrode 145) position the droplet 180 containing particles/beads or analyte molecules 190 over the array of wells 160. The device includes a first substrate 110, a layer 150 of dielectric material positioned on the upper surface of the first substrate and a hydrophobic layer 155 that covers the upper surface of the dielectric layer. After a period of time sufficient for deposition of particles/beads/analyte molecules into the wells, the droplet is displaced by a droplet of immiscible liquid 195 (or an immiscible liquid as explained herein). The droplet of immiscible liquid functions to move droplet 180 with any bead/particles/analyte molecules not deposited into the wells away from the wells and to cover the wells.

Figure 17:
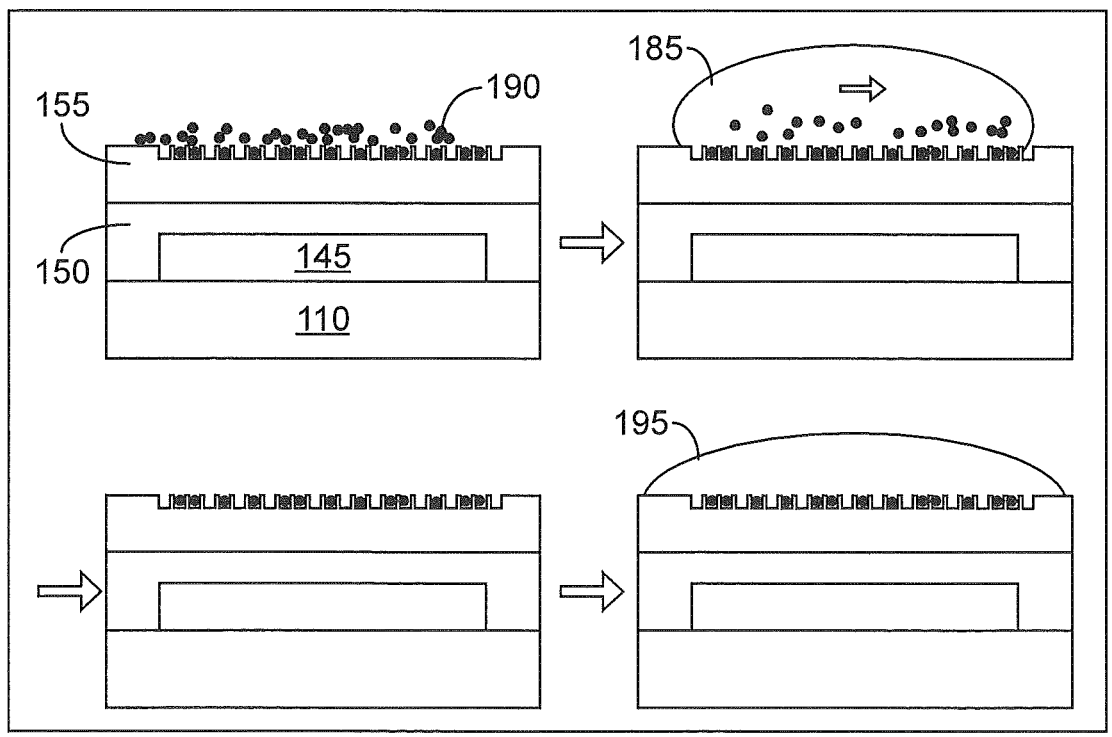
FIG. 17 illustrates another exemplary method for removing beads not located in the wells of the depicted device.

FIG. 17 depicts another method for removing any beads not deposited into wells. In FIG. 17, many beads 190 are remaining over the wells after removal of the droplet containing the beads. The device includes a first substrate 110, a layer 150 of dielectric material positioned on the upper surface of the first substrate and a hydrophobic layer 155 that covers the upper surface of the dielectric layer. These beads are washed away using an aqueous droplet. 185 After removal of the aqueous droplet, the array of wells contains the deposited beads. An immiscible fluid 195 is then moved over the array of wells to seal the wells.

A number of forces may be utilized to facilitate the movement of particles/beads from a droplet positioned over the array of wells into the wells. Such forces include gravity, electrical force, magnetic force, etc. Permanent magnets or electromagnets may be used as source of magnetic force. In certain embodiments, the magnets are not located on the integrated microfluidic and detection chip. Analyte molecules may be deposited into the wells via diffusion.

Immunoassays

The devices provided herein may be used to measure amount of an analyte of interest in a sample. As used herein, the terms "analyte", "target analyte", "analyte of interest" refer to the analyte being measured in the methods and devices disclosed herein. An analyte may be a small molecule, peptide, protein, RNA, DNA, lipid, carbohydrate, toxin, or a cell. Samples which may assayed to determine the amount of analyte present in the sample may include biological fluid samples such as, for example, blood, plasma, serum, saliva, sweat, urine, etc.

As used herein, the terms "sample", "test sample", "biological sample" refer to fluid sample containing or suspected of containing an analyte of interest. The sample may be derived from any suitable source. In some cases, the sample may comprise a liquid, fluent particulate solid, or fluid suspension of solid particles. In some cases, the sample may be processed prior to the analysis described herein. For example, the sample may be separated or purified from its source prior to analysis; however, in certain embodiments, an unprocessed sample containing the analyte may be assayed directly. The source of the analyte molecule may be synthetic (e.g., produced in a laboratory), the environment (e.g., air, soil, etc.), an animal, e.g., a mammal, a plant, or any combination thereof. In a particular example, the source of an analyte is a human bodily substance (e.g., blood, serum, plasma, urine, saliva, sweat, sputum, semen, mucus, lacrimal fluid, lymph fluid, amniotic fluid, lung lavage, cerebrospinal fluid, feces, tissue, organ, or the like). Tissues may include, but are not limited to skeletal muscle tissue, liver tissue, lung tissue, kidney tissue, myocardial tissue, brain tissue, etc. The sample may be a liquid sample or a liquid extract of a solid sample. In certain cases, the source of the sample may be an organ or tissue, such as a biopsy sample, which may be solubilized by tissue disintegration/cell lysis. A sample may be processed prior to performing immunoassay on the sample. For example, the sample may be concentrated, diluted, purified, amplified, etc.

A number of immunoassay formats that generate an analyte related signal may be used. In some embodiments, a sample droplet containing the target analyte may be merged with a droplet containing magnetic beads on which a first binding member that specifically binds to the target analyte present in the sample is attached. Merging creates a single droplet which may be incubated for a time sufficient to allow binding of the first binding member to an analyte present in the sample droplet. Optionally, the single droplet may be agitated to facilitate mixing of the sample with the first binding member. Mixing may be achieved by moving the single droplet back and forth, moving the single droplet around over a plurality of electrodes, splitting a droplet and then merging the droplets, or using SAWs, and the like. Next, the single droplet may be subjected to a magnetic force to retain the beads at a location in the device while the droplet may be moved away to a waste chamber or pad and replaced with a droplet containing a second binding member. The second binding member may be detectably labeled. The label may be any label that can be optically detected. The label may be a fluorescent label. An optional wash step may be performed, prior to adding the second binding member, by moving a droplet of wash buffer to the location at which the beads are retained using the magnetic force. The beads may or may not be resuspended in the wash buffer; a magnetic force is applied to the magnetic beads and the wash buffer is transported to a waste location. After a period of time sufficient for the second binding member to bind the analyte bound to the first binding member, the droplet containing the second binding member may be moved away while the beads are retained at the location. The beads may be washed using a droplet of wash buffer. Following the wash step, the magnetic force may be removed and a droplet containing the labeled beads which has a complex of the first binding member, analyte and the second binding member may be moved over to the detection module. As explained herein, the immunoassay may be carried out in the sample preparation module. The labeled beads may be allowed to settle into the array of wells in the detection module. The beads may settle using gravitational force or by applying electric or magnetic force. Following a wash step to remove any beads not located inside the wells, the wells may be sealed by using a hydrophobic liquid.

In another embodiment, the second binding member may be attached to a particle or a bead via a cleavable linker. Following the wash step to remove any unbound second binding member, the particle or bead attached to the second binding member may be cleaved either chemically or by photocleavage. The cleaved particles/beads may be moved to the detection module and the particles/beads present in the wells quantitated.

In some cases, the particles/beads attached to the second binding member may be labeled. For example, the particles/beads may be color coded or fluorescent.

In another embodiment, the second binding member may be attached to a cleavable label. Following the wash step to remove any unbound second binding member, the label attached to the second binding member may be cleaved either chemically or by photocleavage. The cleaved label may be moved to the detection module, where the label is allowed to diffuse into the wells. Following removal of any label not deposited in the wells, the wells may be sealed with a hydrophobic fluid and the label may be quantitated.

A second immunoassay format that can generate an analyte related signal may also be used. In some embodiments, a sample droplet containing the target analyte may be merged with a droplet containing labeled analyte or labeled competitor molecule to produce a single droplet. The labeled analyte or labeled competitor molecule competes with the target analyte for binding to a first binding member. The label may be any label that can be optically detected. The label may be a fluorescent label. The single droplet may be agitated to facilitate mixing which may be achieved by moving the single droplet back and forth, moving the single droplet around over a plurality of electrodes, splitting a droplet and then merging the droplets, or using SAWs, and the like. The single droplet may then be merged with a droplet containing magnetic beads on which a first binding member that specifically binds the target analyte and the labeled analyte (or the labeled competitor molecule) is attached. Merging creates a second single droplet which may be incubated for a time sufficient to allow either target analyte or labeled analyte (or the labeled competitor molecule) present in the droplet to competitively bind with the first binding member. Optionally, the second single droplet may be agitated to facilitate mixing of the target analyte-labeled analyte mixture with the first binding member. Next, the second single droplet may be subjected to a magnetic force to retain the beads at a location in the device while the droplet may then be moved away to a waste reservoir/pad and the beads may be contacted with a droplet containing a wash buffer. If a fluorescent label is used, the beads may be re-suspended in the wash buffer and then the beads may be moved over to the detection module.

If the label used is an enzyme, then a magnetic force is applied to capture the magnetic beads and the wash buffer is transported to a waste location. A droplet which contains enzyme substrate may be contacted with the magnetic beads which have a complex of the first binding member, analyte and labeled analyte. Optional mixing may be performed, after which the beads may be moved over to the detection module. As explained herein, the immunoassay may be carried out in the sample preparation module. The labeled beads may be allowed to settle into the array of wells in the detection module. The beads may settle using gravitational force or by applying electric or magnetic force. Following a wash step to remove any beads not located inside the wells, the wells may be sealed by using an immiscible liquid.

As will be appreciated by those in the art, the binding members will be determined by the analyte to be analyzed. Binding members for a wide variety of target molecules are known or can be readily found or developed using known techniques. For example, when the target analyte is a protein, the binding members may include proteins, particularly antibodies or fragments thereof (e.g., antigen-binding fragments (Fabs), Fab' fragments, F(ab')$_2$ fragments, full-length polyclonal or monoclonal antibodies, antibody-like fragments, etc.), other proteins, such as receptor proteins, Protein A, Protein C, or the like. In case where the analyte is a small molecule, such as, steroids, bilins, retinoids, and lipids, the first and/or the second binding member may be a scaffold protein (e.g., lipocalins). In some cases, binding member for protein analytes may be a peptide. For example, when the target analyte is an enzyme, suitable binding members may include enzyme substrates and/or enzyme inhibitors which may be a peptide, a small molecule and the like. In some cases, when the target analyte is a phosphorylated species, the binding members may comprise a phosphate-binding agent. For example, the phosphate-binding agent may comprise metal-ion affinity media such as those describe in U.S. Pat. No. 7,070,921 and U.S. Patent Application No. 20060121544.

In certain cases, at least one of the binding members may be an aptamer, a nucleic acid, such as, DNA, RNA, oligonucleotides, and the like.

In certain embodiments, the binding member binds specifically to the analyte. By "specifically bind" or "binding specificity," it is meant that the binding member binds the analyte molecule with specificity sufficient to differentiate between the analyte molecule and other components or contaminants of the test sample. For example, the binding member, according to one embodiment, may be an antibody that binds specifically to an epitope on an analyte.

Surface Acoustic Wave Device, System, and Methods

Systems, device, and methods related to an integrated surface acoustic wave sample preparation and analyte detection device are provided by the subject disclosure.

In one example, the device includes a sample preparation component, e.g., a substrate with a surface that allows for liquid or fluids to propagate across the surface thereof via manipulation by acoustic forces. In the same example, the device includes an analyte detection component configured to receive the propagated liquid and perform analyte detection on the received liquid.

The term "surface acoustic waves" and grammatical equivalents thereof as used herein refer generally to propagating acoustic waves in a direction along a surface. Traveling "surface acoustic waves" (TSAWs) enable coupling of surface acoustic waves into a liquid. In some examples, the coupling may be in the form of penetration or leaking of the surface acoustic waves into the liquid. In some examples, the surface acoustic waves are Raleigh waves. Propagation of the surface acoustic waves can be performed by streaming the surface acoustic waves through a liquid. Propagation of surface acoustic waves may be conducted in a variety of different ways and by using different materials, including generating an electrical potential by a transducer, such as a series of electrodes.

The electrodes may be patterned onto a planar substrate. In some examples, the planar substrate may be a piezoelectric layer. In some examples, the electrodes may be fabricated onto the piezoelectric layer using standard lithography and lift off/wet etching processes. The structure of the electrodes, spacing between electrodes, the number of electrodes (i.e., resolution) on the substrate may vary. In some examples, interdigitated (IDT) transducers or electrodes are used. In some examples, the sample preparation component may include a liquid. In some examples, there may be multiple layers. The different layers may have different arrangement or configuration of scattering structures for scattering surface acoustic waves. As a result, liquid droplet movement across the different layers may differ due to the varied scattering structures present.

In some examples, SAW are propagated when a single transducer or electrode is activated. In other examples, a plurality (e.g., pair) of electrodes fabricated on the substrate surface may generate two traveling SAWs propagating towards each other. In some examples, SAW displacement is activated when a radio frequency (RF) range is applied to the electrodes. Upon being activated, the electrodes or transducers emit an electric potential across the surface of the substrate, where the substrate is subjected to mechanical stress. Examples of mechanical stress are continuous contraction and expansion of the surface of the substrate. As a result of this continuous deformation of the substrate, surface acoustic waves are propagated across the surface.

Surface acoustic waves can be measured according to amplitude and frequency. Therefore, the frequency and amplitude of the electric potential generated by the electrodes is responsible for the amplitude and frequency of SAW.

Propagation of SAW may be in a linear direction. In some examples, SAW may propagate across the longitudinal length of the substrate surface. In other examples, SAW may propagate across the width of the substrate surface. In other examples, propagation of SAW may be in a non-linear direction and motion. Because fluid is a dissipative system, the response to harmonic forcing via SAW may not necessarily be harmonic.

When a traveling SAW contacts liquid, the liquid absorbs part of the SAW's energy and may refract it in the form of longitudinal waves. Absorption of the refracted acoustic energy induces fluid flow or propagation across the surface of the substrate. When a surface acoustic wave is propagated along the surface of the sample preparation component, the SAW may come into contact with the liquid. As a result of the liquid interacting with SAW, results in the SAW being transferred into the liquid. SAWs manipulate fluid by means of "contact free manipulation", which is meant the liquids are propagated to the detection component by the acoustic waves leaking or penetrating into the fluid. As a result, there is a minimization of outside contamination of the biological sample or analyte.

In some examples, driving exemplary fluid actions includes pumping, mixing, jetting, etc. As a result, the liquid is propagated along the surface of the sample preparation component.

In some examples, the liquid can be dispensed as a droplet to be actuated onto the surface of the sample preparation component prior to the activation of the SAW electrodes. Droplet actuation can be used for positioning droplets and dispensing droplets onto the sample preparation component.

In other examples, instead of liquid droplet-based microfluidics, a SAW driven pump may be used to pump liquid onto the open surface. In some examples, fluid may be pumped through enclosed channels.

The liquid may be any test sample containing or suspected of containing any analyte of interest. As used herein, the terms "analyte", "target analyte", "analyte of interest" refer to the analyte being measured in the methods and devices disclosed herein. The liquid droplets may also refer to particles or beads in an aqueous solution, Samples may include biological fluid samples such as, for example, blood, plasma, serum, saliva, sweat, etc.

In some examples, the liquid can be disposed as a single particle. In other examples, the liquid can be disposed as a group of particles (e.g., thousands of particles). The liquid droplets may vary according to a wide range of length scales, size (nm to mm), as well as shape.

The propagation of surface acoustic waves may also be affected by the presence of phononic structures patterned onto the surface of the sample preparation platform. These phononic structures may control the propagation of the sound acoustic waves. For example, the phononic structures may control the direction, movement, velocity of the SAW thus, providing enhanced functionality. The phononic structures may be fabricated onto the substrate using standard lithography, lift off/wet etching processes, embossing/nanoimprint lithography, and micromachining, pressure, heat, and laser modification of the substrate to form these phononic structures. These phononic structures may assume a variety of shapes and sizes as well. In some examples, the phononic structures may be pillars, cones, or holes that form a lattice within the substrate.

Surface Acoustic Waves Sample Preparation Component

"Sample preparation component" and grammatical equivalents thereof as used herein refer to a generally planar surface on which the liquid droplets are initially dispersed upon and where steps of immunoassay as described herein may be carried out. In some examples, the substrate may be made of materials with high acoustic reflection.

In some examples, the sample preparation component includes a superstrate coupled to a substrate. In some examples, the superstrate is removably coupled to the substrate. In other examples, the superstrate is permanently coupled to the substrate. Some examples include making the substrate from a polymer-based or paper-material. The polymer-based substrate may be treated with a hydrophobic coating or fabrication may add a hydrophobic layer over the polymer-based substrate or with another substrate such that the substrate is impermeable to aqueous fluid.

In some examples, the sample preparation component may also include an assay reagent included on the superstrate. The sample preparation component further includes a superstrate coupled to a substrate.

In yet another example, the sample preparation component may include a series of scattering structures included on the superstrate. Examples of the scattering structures may include phononic structures, which are described in greater detail below.

In some examples, the substrate may be a piezoelectric material. The piezoelectric layer may be made from a composite layer, such as $LiNbO_3$. The superstrate may further include a series of electrodes or transducer. In some examples, surface acoustic waves generated by the electrodes or IDT may also be coupled into the superstrate.

In some examples, the superstrate may be made from a variety of materials, such as plastics (e.g., PET, PC, etc.).

In some examples, the superstrate may be fabricated of a material with a relatively high electromechanical coupling coefficient. In some examples, electrodes may be fabricated onto piezoelectric materials. In one example, single crystal lithium niobate ($LiNbO_3$) may be used as a substrate to pattern electrodes in SAW microfluidic applications. In another example, silicon may be used as a substrate material to pattern electrodes. Other examples of material applicable for fabricating a SAW-generating substrate include polycrystalline material, microcrystalline material, nanocrystalline material, amorphous material or a composite material. Other examples of material applicable for fabricating a SAW-generating substrate include ferroelectrical material, pyroelectric material, piezoelectric material or magnetostrictive material.

As described herein, the substrate is a material capable of generating surface acoustic waves and propagating acoustic waves.

In addition to the analyte or biological sample to be analyzed, the sample preparation component may also include buffer or wash fluids. In some examples, these buffer or wash fluids may facilitate the propagation of liquids across the sample preparation component and onto the detection component. In other instances, these fluids may be used to wash away any remaining liquid or biological samples once they have being positioned into the nanowell array. Examples of such fluids include air, inert gases, hydrophobic liquids, hydrophilic liquids, oils, organic-based solvents, and high-density aqueous solutions. In certain cases, the device may be filled with a filler fluid which may be air, inert gases, hydrophobic liquids, hydrophilic liquids, oils, organic-based solvents, and high-density aqueous solutions.

In some examples, SAW induced fluidic movement can be visualized by introducing small dyes or particles into the liquid droplet.

The sample preparation surface has a surface on which the liquid may be propagated along the surface. The surface of the sample preparation surface may be any convenient surface in planar or non-planar conformation. The surface may be coated with a hydrophobic material to facilitate movement of the liquid along the surface. In some examples, the hydrophobic material may include octadecyltrichlorosilane (OTS). In other examples, the surface may be patterned to facilitate liquid movement.

In some examples, the substrate of the sample preparation surface may be elastic or flexible. The substrate on which the surface is formed upon may be elastic so that the surface is able to deform so as to facilitate the propagation of surface acoustic waves across the surface.

In certain embodiments, the surface of the substrate may include microfluidic channels to facilitate propagating fluid. In other embodiments, a microfluidic channel is included internal of the substrate to transmit fluid into the substrate.

In some examples, a cover seal may be provided over the upper surface of the substrate of the sample preparation component. In certain instances, the cover seal may prevent contamination of the liquid contents of the surface. In other instances, the cover seal may be a liquid impermeable layer. In other instances, the cover seal may be made from a flexible material such as plastics, silicon, or other type of rubber. In other instances, the cover seal may be made from a non-flexible material such as a glass or other non-flexible material. In some examples, the cover seal may be impenetrable to heat, ultraviolet light, or other electromagnetic radiation to prevent deformation of either the surface or liquid contents present on the surface.

In some examples, a suitable spacer may be positioned between the substrate and the cover seal. By "suitable spacer" as used herein, refers to an element positioned between the substrate of the sample preparation component and the cover seal. In some examples, the suitable spacer may facilitate liquid droplets to move between the surface and the cover seal. In other examples, the suitable spacer may reduce coupling between the traveling surface acoustic waves and the surface.

In the first example sample preparation component, the first substrate Incorporates a material with a relatively high electromechanical coupling coefficient and having a flexible and deformable surface. For example, the first substrate may be a piezoelectric material or silicon.

In some examples, electrodes are arranged on the surface or embedded within the piezoelectric layer. The term "electrodes", as used in this context, refers to electric circuit including an electrode, a series of electrodes (e.g., more than one), a transducer. The electrode may also be patterned into the piezoelectric layer. In some examples, the electrodes may be fabricated onto the substrate using standard lithography and lift off/wet etching processes. The structure of the electrodes, spacing between electrodes, the number of electrodes (i.e., resolution) on the substrate may vary. In some examples, interdigitated (IDT) transducers or electrodes are used. IDT is defined as a combination of a series of electrodes and a piezoelectric layer on which the series of electrodes are included on. In some examples the transducer electrode structures are formed onto the piezoelectric layer. In other examples, the transducer electrode structures are embedded within the piezoelectric layer.

In some examples, surface acoustic waves are propagated when a single transducer or electrode is activated. In other examples, a plurality (e.g., pair) of electrodes fabricated on the substrate surface may generate two traveling surface acoustic waves propagating towards each other. In some examples, surface acoustic waves displacement is activated when a radio frequency (RF) range is applied to the electrodes. Upon being activated, the electrodes or transducers emit an electric potential across the surface of the substrate, where the material is subjected to mechanical stress. Examples of mechanical stress are continuous contraction and expansion of the surface of the substrate. As a result of this continuous deformation of the substrate, surface acoustic waves are propagated across the surface.

In some examples, wavelength of surface acoustic waves is dependent upon the pitch of the transducer (IDT) or series of electrodes.

In one example, the sample preparation component may include a series of phononic structure that are included on the surface of the superstrate. The phononic structures may control the propagation of the acoustic waves. For example, the phononic structures may control the direction, movement, velocity of the surface acoustic waves. The phononic structures may assume a variety of shapes and sizes as well. In some examples, the phononic structures may be pillars, cones, or holes that form a lattice within the substrate. The pattern of phononic structures on the surface of the superstrate may be predefined based on characteristics such as resolution (e.g., number of electrodes per area on the surface), electrode size, inter-digitation of the electrodes, and/or gaps or spacing between the electrodes. In some examples, characteristics of the pattern are selected based on one or more operational uses of the droplet actuator with which the SAW sample prep component is to be associated (e.g., for use with biological and/or chemical assays). In other configurations, the pattern of electrodes may be reconfigurable to enable different patterns to suit different applications. In some examples, an increase in the size or dimensions of the series of electrodes or each individual electrode may also reduce the amount of hydrophobic material applied between adjacent electrodes. Thus, the features of the electrode pattern may maximize the surface area of the SAW platform. Furthermore, increased inter-digitation of the series of electrodes/transducers facilitates the ease with which liquid is propagated across the surface via manipulation of their electrical potentials.

In the first example sample preparation component, hydrophobic material may be applied to the series of electrodes and surface of the substrate to make the superstrate Impermeable to aqueous solutions. As a result of the hydrophobic material, a liquid actuated through a droplet or fluid pump is in a beaded configuration forming a contact angle with the hydrophobic layer of the surface of the substrate. In operation, SAW acoustic waves propagate across the surface coupling to the liquid, for example by penetrating or leaking into the liquid. The amplitude or frequency of the SAW acoustic wave may control the resulting frequency and motion of the moving liquid.

In certain embodiments, the surface acoustic waves propagate along the surface of the substrate and are then coupled into the superstrate. Thereafter, the surface acoustic waves continue to propagate and are guided by phononic structures that may be formed in the superstrate.

In some examples, where SAW acoustic wave are generated by two or more electrodes, it may result in controlling the direction of the liquid that is coupled to the resulting surface acoustic waves. The direction of the propagating liquid may be in a linear direction or non-linear direction. In some examples, the propagation of the liquid droplet may be in a rolling motion. In other examples, propagation of the liquid droplet may be in a sliding motion across the surface. In some examples, where there is a lack of phononic structures on the surface, propagation of the SAW and propagation of the resulting liquid droplet are in the same direction. In other examples, where there is a presence of phononic structures on the surface, propagation of SAW and propagation of resulting liquid droplets are in opposing directions or different directions.

In some examples, the hydrophobic material is a polytetrafluoroethylene material (e.g., Teflon®) or a fluorosurfactant (e.g., FluoroPel™) applied to the surface of the superstrate.

Analyte Detection Component

In some embodiments, the analyte detection component may include an array of wells in which molecules, particles, beads, or cells may be isolated for analyte or biological sample detection purpose, TSAWs (traveling surface acoustic waves) generate acoustic streaming over the surface are across the fluid channels to push fluid (either droplets or cells) towards the well array.

The shape and geometry of the wells may vary according to the type of procedure or application required. In some examples, the wells may vary between being deep chambers to shallow chambers. The wells may be any of a variety of shapes, such as, cylindrical with a flat bottom surface, cylindrical with a rounded bottom surface, cubical, cuboidal, frustoconical, inverted frustoconical, or conical. In certain cases, the wells may include a sidewall that may be oriented to facilitate the receiving and retaining of a nanobead or nanoparticle present liquid droplets that have been moved over the well array. In some examples, the wells may include a first sidewall and a second sidewall, where the first sidewall may be opposite the second side wall. In some examples, the first sidewall is oriented at an obtuse angle with reference to the bottom of the wells and the second sidewall is oriented at an acute angle with reference to the bottom of the wells. The movement of the droplets may be in a direction parallel to the bottom of the wells and from the first sidewall to the second sidewall. The array of wells may have sub-femtoliter volume, femtoliter volume, sub-nanolitre volume, nanolitre volume, sub-microliter volume, or microliter volume. For example the array of wells may be array of femoliter wells, array of nanoliter wells, or array of microliter wells. In certain embodiments, the wells in an array may all have substantially the same volume. The array of wells may have a volume up to 100 µl, e.g., about 0.1 femtoliter, 1 femtoliter, 10 femtoliter, 25 femtoliter, 50 femtoliter, 100 femtoliter, 0.1 pL, 1 pL, 10 pL, 25 pL, 50 pL, 100 pL, 0.1 nL, 1 nL, 10 nL, 25 nL, 50 nL, 100 nL, 0.1 microliter, 1 microliter, 10 microliter, 25 microliter, 50 microliter, or 100 microliter.

In certain cases, the sample preparation component and the analyte detection component may be fabricated from a single planar surface using, for example, a continuous web-fed manufacturing process. In such an example, the sample preparation component and the digital analyte detection component may be positioned adjacent to each other.

In some examples, the sample preparation component may include a sample inlet. By "sample inlet" as used herein, refers to a tubular member, channel, or pipe for introducing liquid to the sample preparation component. For example, the sample inlet may introduce a biological sample onto the surface of the substrate. In other example, the sample inlet may introduce a biological sample internally within the substrate.

In other examples, the sample preparation component and the digital analyte detection component may be positioned over one another in a stacked configuration, separated by a space for droplet manipulation. In the example of the sample preparation component being positioned over the analyte detection component in a stacked configuration or vice versa (the analyte detection component being positioned over the sample preparation component), an inlet or channel may be positioned between the two components. The inlet or channel may direct a sample or analyte between the two components.

Phononic structures may be fabricated or included on the superstrate of the sample preparation component. In certain cases, the phononic structures are imprinted or embossed onto the superstrate. In such examples, the embossing or imprinting of the phononic structures is in a single step. In other examples, it may be multiple steps. Imprinting or embossing of phononic structures may be through the combination of an application of pressure, heat, or ultraviolet light in the presence of a mold, mask, or pattern. In one example, pressure elicited from a mold onto the superstrate may induce deformation of the a surface of the superstrate.

After the phononic structures are included on the superstrate, it may be cured for a sufficient period of time to allow for hardening or deformation of the phononic structures. In addition, the phononic structures may be subject to reagents that modify the physical properties of the phononic structures.

In some examples, the reagents for analyte detection may be printed during fabrication of the integrated sample preparation and analyte detection device in a dehydrated form, Rehydration of the reagents occurs through use of a sample or buffer.

In some examples, the array of wells includes individual well chambers, with each well chamber having a first end and a second end. In one example, the first end of the well may be open, while the second end of the well is closed. In other examples, both the first end of the wells and the second end of the well chambers are closed. Closure of the first end of the well chambers may be through both a permanent closure mechanism and a temporary closure mechanism, By "permanent" as used herein is meant that the closure mechanism is intended to remain a fixture of the chamber of the nanowell. By "temporary" as used herein is meant that the closure mechanism can be removed without affecting the structure, integrity, or rigidity of the closure mechanism. In some aspects, the closure of the well chamber first end may be through a combination of a permanent and a temporary closure mechanism. In one example, the temporary closure mechanism may be a liquid, such as an oil fluid, that can fill the first end of the well chamber. In certain examples, the oil drop may fill the first well end after an analyte, biological sample, or analyte related detectable label has been previously deposited into the well. In other examples, the oil drops may be closure of the first end of the well regardless of the presence of an analyte or biological sample within the well.

The array of wells has a pattern of well chambers (e.g., the formation of wells in the array) suitable for receiving a plurality of labels, beads, labeled beads, tags, and the like. The pattern of the array of the wells may vary according to resolution and spacing between well chambers.

In some examples, the pattern of the well array can be fabricated using nanoimprint lithography. In other examples, the pattern of the nanowell array can be fabricated through a combination of anyone of molding, pressure, heat, or laser.

The size of the well array may vary. In some examples, the nanowell array may be fabricated to have individual nanowell chambers with a diameter of 100 nm and with a periodicity of 500 nm.

In some examples the well array may be substantially as described in the section related to digital microfluidics and detection module.

In some examples, detection of the analyte or biological sample of interest may occur through optical signal detection. For example, shining an excitation light (e.g., laser) in order to measure the signal intensity result. In other examples, the analyte desired may be detected by measuring an optical signal emanating from each well chamber and quantified by quantifying the result. For example, the number of positive counts (e.g., wells) is compared to the number of negative counts (e.g., wells) to obtain a digital count. Alternately or in addition, a signal correlated to analyte concentration may be measured (analog quantitation). A variety of signals from the wells of the device may be detected. Exemplary signals include fluorescence, chemiluminescence, colorimetric, turbidimetric, etc, Adjacent Configuration of Sample Preparation and Analyte Detection Device In some embodiments, the array of wells is positioned on the same superstrate as the sample preparation component. In some examples, the superstrate and the array of wells may be positioned on a first substrate. The first substrate may be divided into a proximal portion at which droplets to be analyzed are initially disposed and a distal portion towards which the droplets are moved for analyte detection. The superstrate may be present on the proximal portion of the first substrate and the array of wells may be positioned on a distal portion of the first substrate. As such the superstrate which forms the sample preparation component and the array of wells which form the analyte detection component may be directly adjacent. As used herein, the term "directly adjacent" refers to there being a lack of object separating or dividing the sample prep component and the array of wells. In examples, where the sample prep component and array of wells are directly adjacent to each other, the propagation of the liquid droplets across the surface of the sample prep component is seamlessly transitioned onto the surface of the array of wells. In other examples, the array of wells is positioned indirectly adjacent to the sample prep component. As used herein, the term "indirectly adjacent" refers to there being an object or element separating or dividing the sample prep component.

In some examples, to facilitate liquid movement and improve position accuracy of the droplets into the individual well chambers, the substrate surface of the sample preparation component may be patterned or coated with a hydrophilic material. In other examples, reagents such as oils and emulsions may be used to seal the well arrays.

Figure 13A:
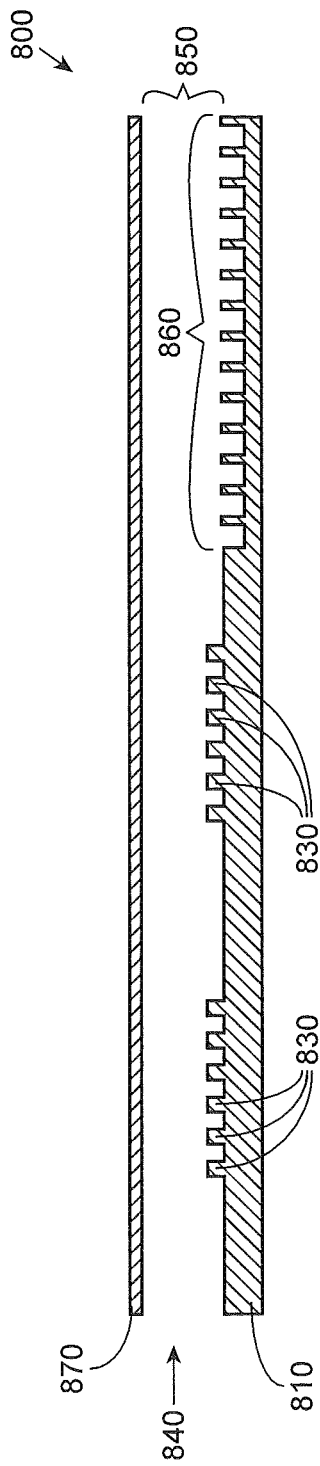
FIG. 13A illustrates a side view of one embodiment of the surface acoustic component of the integrated microfluidic and analyte device and array of wells.

FIG. 13A illustrates an exemplary integrated digital microfluidic and analyte detection device 800. FIG. 13A illustrates a side view of a sample preparation component positioned adjacent to an analyte detection component. As shown in FIG. 13A, the sample preparation component includes a superstrate 810. The superstrate 810 includes a series of phononic structures 830. The size, shape, and dimensions of the phononic structures may vary. As shown in FIG. 13A, the sample preparation component is positioned to be directly adjacent to the analyte detection component comprising an array of wells 860. Where these components are positioned adjacent to each other, liquid propagated across the surface of the superstrate 810 can be collected into individual well chambers on the well array 860. In this particular example, a sample inlet channel 840 is positioned between the superstrate 810 and the cover 870. The superstrate 810 and the cover 870 are separated by space/gap 850 defining a space where liquid droplets are manipulated (e.g., merged, split, agitated, etc.). However, in other examples, a sample inlet channel is not included. The size, dimensions, and variations of the sample inlet channel may vary. For example, the sample inlet channel may introduce a fluid onto the surface of the substrate 810. In other examples, the sample inlet channel may introduce a fluid internally within the substrate 810.

In some examples, a cover seal may be provided over the surface of the sample preparation component. In certain instances, the cover seal may prevent contamination of the liquid contents of the surface. In other instances, the cover seal is a liquid impermeable layer. In other instances, the cover seal is made from a flexible material such as plastics, silicon, or other type of rubber. In other instances, the cover seal is made from a non-flexible material such as a glass or other non-flexible material. In some examples, the cover seal may be impenetrable to heat, ultraviolet light, or other electromagnetic radiation to prevent deformation of either the surface or liquid contents present on the surface of the sample preparation component.

In some examples, a heat sink may be provided in order to dissipate the heat generated by generation of surface acoustic waves across the surface of the substrate.

Stacked Configuration of Sample Preparation and Analyte Detection Device

In some embodiments, the array of wells (detection component) is positioned over the sample preparation component separated by a space where the droplets are manipulated. In some examples, an inlet or channel may be positioned between the two components. The inlet or channel may direct a sample or analyte between the two components.

In some examples, the well array may be imprinted or embossed onto a first substrate and the phononic structure may be present on a superstrate positioned in a spaced apart manner from the first substrate. The superstrate may be supported by a second substrate.

In some examples, the step of coupling the first substrate that includes the array of wells with the superstrate may be facilitated with the use of a bonding agent, adhesive agent, tapes, glues, soldering, or other affixing agent capable of coupling the array of wells to the superstrate. In other examples, the step of coupling the array of wells onto the phononic structures of the sample prep component may be achieved through use of mechanical fasteners, fixers, bolts, and other mechanical components such as latches. In other examples, the step of coupling the array of wells onto the phononic structures of the sample prep component may occur through setting and positioning the array of wells over the phononic structures of the sample prep component. In some examples, the phononic structures of the substrate may be in parallel orientation to the well array component.

The spacing between the phononic structures of the superstrate and the well array may vary according to the type of application to be performed, the size of the liquid droplet being actuated onto the surface of the substrate, the size, shape and arrangement of phononic structures, the size of the sample channel/inlet, and the amplitude of the surface acoustic waves propagating across the surface.

Figure 13B:
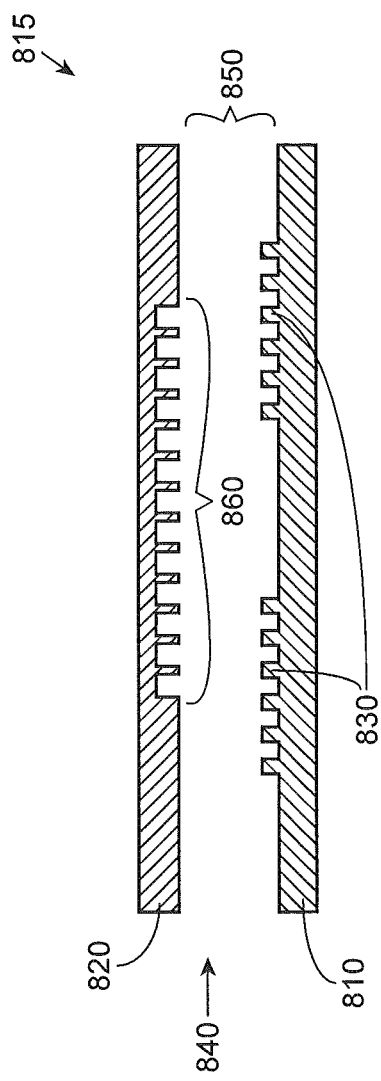
FIG. 13B illustrates a side view of another embodiment of the surface acoustic component of the integrated microfluidic and analyte device and array of wells.

FIG. 13B illustrates a side view of a stacked configuration of a superstrate and well array component. As shown in FIG. 13B, the superstrate 810 includes a series of phononic structures 830. The phononic structures 830 are arranged in an array of repeating structural elements. The size, shape, and dimensions of the phononic structures may vary. In this example, an array of wells 860 is also present. In this example, the array of wells 860 is positioned directly over the superstrate. As illustrated in FIG. 13B, the opening of the wells may be directly opposite the phononic structures. In this particular example, a sample inlet channel 840 is positioned between the well array and the superstrate. However, in other examples, a sample inlet channel is not included. The size, dimensions, and variations of the sample inlet channel may vary. For example, the sample inlet channel may introduce a fluid onto the surface of the superstrate 810. In other examples, the sample inlet channel may introduce a fluid internally within the superstrate 810. The substrate 820 that includes the array of wells 860 is positioned in a spaced apart manner from the superstrate 810 and is separated from the superstrate 810 by a gap/space 850.

The array of wells as shown in FIGS. 13A-133 can vary in size and/or shape. For example, the well array can be substantially shallow or deep. The resolution of the well array is affected by the spacing between each well chamber. For example, minimal spacing between the well chambers allows for a greater number of wells to collect a greater number of analytes or biological samples. In some examples, well array may be formed via ablating the substrate. The pattern of the well array may be formed by using a special pattern or special mask, and subjecting the mask to laser ablation.

Fabricating Surface Acoustic Wave Sample Preparation and Detection Device

Figure 14A:
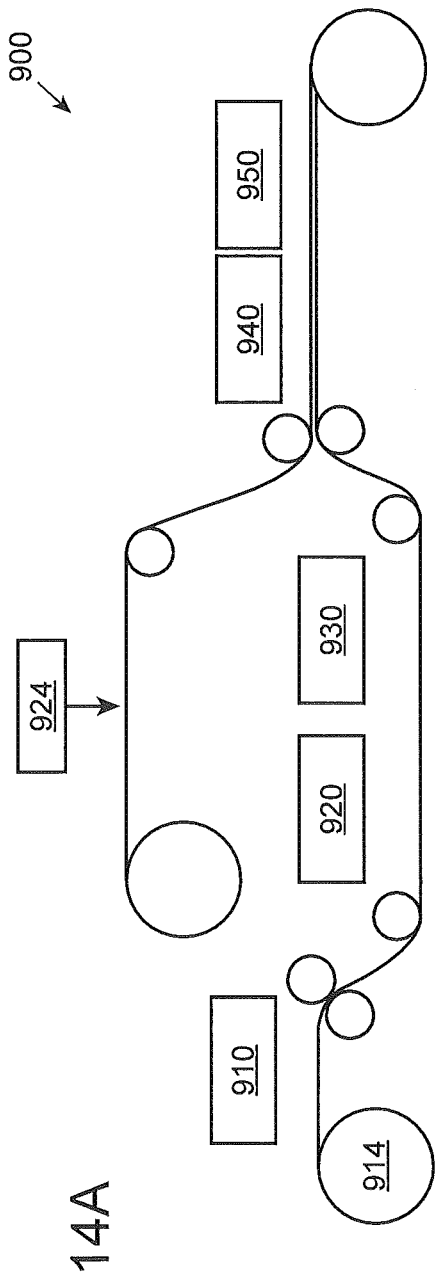
FIGS. 14A and 14B illustrate an example of fabricating the sample preparation component and well array component.
Figure 14B:
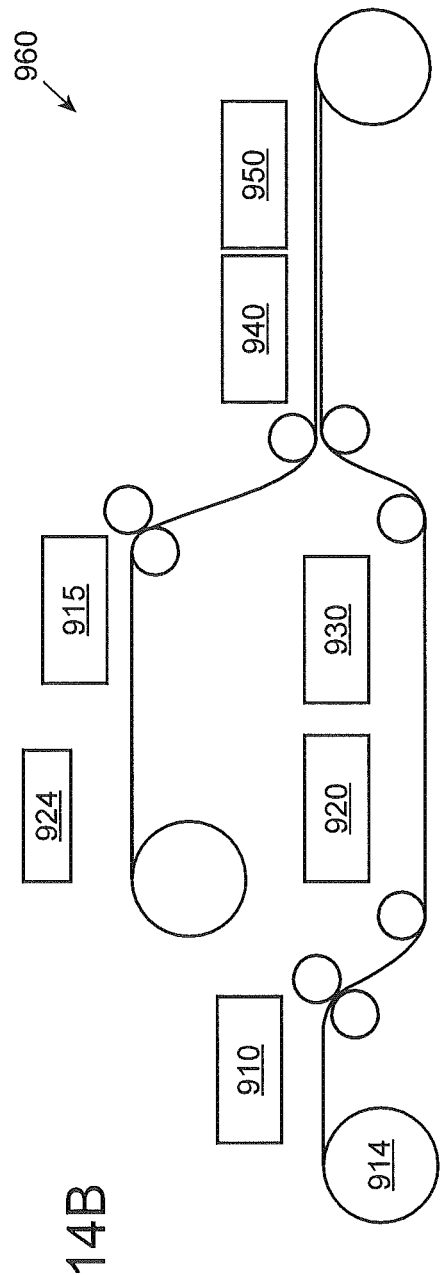

FIGS. 14A-14B illustrate assembly lines 900 and 960 and exemplary methods for separately fabricating the SAW devices disclosed in the foregoing sections. FIG. 14A illustrates that the sample preparation component and nanowell array component are positioned adjacent to each other by fabricating the phononic structures and the array of wells on a single base substrate. A superstrate (see 820) is placed on an assembly line 900. Propagation of the superstrate (see 820) along the assembly line 900 is facilitated by a conveyer belt-like mechanism utilizing a series of rollers. A roll of the superstrate 914 is unspooled and is subjected to an embossing unit 910, which subjects the material to intense heat, pressure, or ultraviolet light in order to form phononic structures on the superstrate or embedded within the superstrate using a mold. Thereafter, the superstrate passes through a plurality of rollers to a surface treatment component 920, which modifies properties of the superstrate. Thereafter, the superstrate passes through an inkjet printer 930 that deposits assay reagents on the superstate. The array of wells is created using a laser ablation 924. In some examples, the resulting structures may be subject to a curing step. In other examples, the resulting structures may be subjected to surface treatment to modify their physical properties, for example, incorporating functionalized reagents required for assay protocols. A cover is them laminated 940 onto the superstrate. Prior to placing the cover on the superstrate, a suitable spacer is placed between the superstrate and the cover to enable liquid droplets to move between the two surfaces. The assembled structure may be diced 950 to generate individual devices.

FIG. 14B illustrates an exemplary assembly line 960 and a method for fabricating the device 815 as depicted in FIG. 13B, The superstrate is subject to a fabrication process using an embossing unit 910, which subjects the superstrate to intense heat, pressure, or ultraviolet light in order to form repeating structural elements of phononic structures in the presence of a mold. Thereafter, the superstrate passes through a surface treatment component 920 to modify properties of the superstrate surface. Thereafter, the superstrate passes through an inkjet printer 930, to deposit assay reagents in situ. To form the detection module comprising an array of wells, a first substrate is subjected to either laser ablation 924 or embossing unit 915. The embossing unit 950 subjects the first substrate to intense, heat, pressure, or ultraviolet light to form well array component on the substrate. At the lamination unit 940, both the superstrate and the first substrate containing well array are combined together and subsequently bonded. As a result, the superstrate and the substrate are aligned vertically within a stack configuration. Thereafter, the stacked substrates are subject to a dicing component 950, for example, to generate individual devices.

The devices and systems and method described herein that propagate droplet actuation may also include a variety of other forces that affect droplet actuation. For example, movement of the droplets across the surfaces may include electric field-mediated forces, electrostatic actuation, electrowetting, dielectrophoresis, electric field gradients or electrode-mediated forces. In embodiments where a combination of surface acoustic waves and digital microarray electrodes are used for droplet manipulation the SAW devices described herein may include a series of electrodes.

The integrated devices disclosed herein may be used to prepare a variety of samples, such as biological sample, for detection of an analyte of interest. In certain cases, the device may be used for carrying out digital immunoassay and detect presence or absence of nanoparticles/nanobeads that are correlated to the presence or absence of an analyte.

The terms "bead" and "particle" are used herein interchangeably and refer to substantially spherical solid support on which the first binding member is immobilized. Beads/particles may be nanobeads/nanoparticles. Magnetic beads/particles may be ferromagnetic, ferrimagnetic, paramagnetic, superparamagnetic or ferrofluidic. Exemplary ferromagnetic materials include Fe, Co, Ni, Gd, Dy, $CrO_2$, MnAs, MnBi, EuO, NiO/Fe. Examples of ferrimagnetic materials include $NiFe_2O_4$, $CoFe_2O_4$, $Fe_3O_4$ (or $FeO.Fe_2O_3$).

Nucleic Acid Amplification and Detection

Nucleic acid testing (NAT) is often used in diagnostic methods involving detecting the presence of a target nucleic acid in a biological sample. Due to the level of amplification of the target nucleic acid needed to reliably detect a target analyte in a biological sample, NAT is an expensive and time consuming process. Further, NAT requires skilled technicians and expensive equipment only available in a laboratory setting. As such, there is a need for NAT that requires minimal amplification and can be carried out in a point of care setting using simplified sample preparation and target analyte detection.

Disclosed herein are methods for NAT that leverage a sensitive detection technique based on digital detection in order to reduce the level of amplification required to reliably detect a target analyte in a sample. The increased sensitivity of the digital detection of the target analyte enables reduction in the amplification cycles needed to detect a target analyte. In comparison, analog detection as used in conventional NAT testing requires a much higher level of amplification in order to overcome background signal. The ultrasensitive digital detection techniques described in U.S. Pat. Nos. 8,415,171; 8,236,574; 8,846,415 may be used in the NAT methods described herein. These detection techniques utilize an array of wells into which capture objects that are associated with an analyte molecule are spatially segregated.

The methods disclosed herein utilize a method for indirect detection and/or measurement of a target nucleic acid in a sample by transforming the NAT into an immunoassay that generates labeled captured objects, where the number of labeled capture objects is proportional to the level of the target analyte in the sample. As described in the Examples section of the application, the disclosed methods lower the limit of detection of NAT to as low as 6000 molecules which requires reduced numbers of amplification cycles, thereby lowering time and cost of reagents. The number of amplification cycles to generate about 6000 molecules of the target nucleic acid may be reduced to 15 cycles or less (e.g., 5-15 cycles, 5-10 cycles, 5-8 cycles, 10-15 cycles, 5 cycles, 7 cycles, or 10 cycles) as compared to the 25 or more rounds of amplification required for the conventional NAT that utilizes standard analog detection techniques. Thus, the time required for generating amplified target nucleic acid that can be detected using the methods and devices described herein may be less than 40 min, less than 10 minutes, less than 5 minutes, e.g., 1 min, 5 min, 10 min, 15 min, 20 min, 25 min, 30 min, 35 min, 40 min, about 15-25 min, about 15-20 min, about 20-25 min, about 25-30 min, about 5-10 min, or about 10-15 min.

In certain embodiments, the detection of the amplified target nucleic acid may be carried out in the array of wells as disclosed in the preceding sections. The array of wells may be part of an integrated device that is used to carry out at least a portion of the sample preparation needed prior to the detection. In certain embodiments, an integrated digital microfluidic and analyte detection device may be used in the detection of a target nucleic acid in a sample. For example, in some cases, the assay processing step and digital counting may be performed by using the integrated digital microfluidic and analyte detection device. In some embodiments, the assay processing step may be performed in the digital microfluidic module of the integrated device and the digital counting may be performed using the analyte detection module of the integrated device.

In certain cases, a biological sample (e.g., human blood sample) that contains or is suspected of containing a target nucleic acid may undergo preparation/processing prior to detection by a system of the present disclosure. The preparation/processing may include the following steps: i) isolation of total nucleic acid that contains a target nucleic acid from the sample, ii) optionally, enrichment of the target nucleic acid, iii) amplification of the target nucleic acid, and iv) processing of the amplified target nucleic acid. Each step can be performed manually, automatically, or by a combination thereof.

Each step may be executed by a separate system or module configured to perform the step. For example, a sample preparation/nucleic acid preparation module may be configured to perform release of and optional purification of total nucleic acid from a sample. Target enrichment of the target nucleic acid can be performed by a target enrichment module. In some cases, sample preparation/nucleic acid preparation and target enrichment can be performed by the module. Amplification of a target nucleic acid sequence can be executed by a module (i.e., amplification module) configured to perform, e.g., isothermal target amplification, polymerase chain reaction, or another method for amplifying a target nucleic acid sequence. An assay processing module can be configured to perform all the procedures necessary for preparing the analyte(s) for detection, for example, capture target amplified nucleic acid sequences (e.g., immunocapture target sequences on a capture object, e.g., beads). A detection module can be configured to perform digital counting of the amplified target nucleic acid molecules.

Each module may function separately, in which each step the module is configured to perform, can be performed automatically by digital microfluidics, surface acoustic wave microfluidics, conventional microfluidics or robotics. Alternatively, each of the steps may be performed manually or robotically. In certain embodiments, some of the steps may be performed manually or robotically while the other steps may be performed automatically using a module as disclosed herein. Each module can alternatively function in an integrated system, wherein the procedures each module performs are carried out automatically by digital microfluidics, surface acoustic wave microfluidics, conventional microfluidics or robotics, or a combination of thereof. The product of each module of such an integrated system may be automatically transferred to the next module. For example, lysed cell sample or isolated nucleic acid from the sample preparation module can be transferred using automation to the amplification module. Such transfer steps can be carried out automatically by digital microfluidics, surface acoustic wave microfluidics, conventional microfluidics or robotics, or a combination thereof.

In some cases, one, two, three, or all modules can be part of a fully integrated system. For example, for nucleic acid testing, the amplification module, assay processing module and detection module can be integrated into one system, which allows for the target nucleic acid to be detected be substantially free from contaminants. As another example, the sample preparation module, amplification module and assay processing module can be integrated into one system. Processed samples can then be transferred to the detection module for detection of a target nucleic acid. Any combination of integrated and non-integrated modules can be employed.

Each module of a system of the present disclosure can be a disposable device. The sample preparation module, amplification module, assay processing module and detection module can each be disposable devices. Each module can also be fully integrated onto the same disposable device. Any combination of modules can be integrated onto a disposable device of the present disclosure.

Sample Preparation

In certain embodiments, an integrated digital microfluidic and analyte detection device may find use in the detection of a target nucleic acid in a given sample. In certain cases, a given sample (e.g., human blood sample) that contains a target nucleic acid may undergo several steps prior to detection by an integrated system of the present disclosure.

Such steps include: i) preparation of total nucleic acid that contains a target nucleic acid from the sample, ii) amplification of the target nucleic acid, and iii) processing of the target nucleic acid. Upon processing of the target nucleic acid, it may be transferred to an integrated system of the present disclosure for detection.

In some cases, a given sample may be whole blood, and nucleic acid detection is performed on only a fraction of the whole blood (e.g., serum, plasma). Serum is the liquid fraction of whole blood that is collected after the blood is allowed to clot. Generally, the clot is removed by centrifugation and the resulting supernatant, called serum, is collected. Plasma is the liquid fraction of whole blood in which the whole blood is not allowed to clot (e.g., has been treated by an anti-coagulant). Methods of plasma and serum preparation are known to those skilled in the art. In cases where a given sample is whole blood, and where nucleic acids are detected from a specific fraction of whole blood, steps to separate such fractions are performed prior to isolating nucleic acids from the sample.

Total nucleic acid is obtained from a given sample (e.g., whole blood, serum, plasma, tissue, etc.) using extraction methods known to those skilled in the art. Such methods may initially include lysis, inactivation of nucleases, and separation of nucleic acids from cell debris. Methods for isolating nucleic acids from extracts employ combinations of extraction/precipitation, chromatography, centrifugation, electrophoresis and affinity separation. Additional methods for isolating nucleic acids will be recognized by those skilled in the art. In some cases, separation of the total nucleic acid from other components of the sample may not be performed. Rather, a lysed sample may be used for the amplification of the target nucleic acid. For Example, the cells in the sample may be lysed using Lyse and Go PCR reagent (Thermo Scientific).

In some cases, extraction/precipitation methods may include solvent extraction performed to eliminate contaminants from nucleic acids (e.g., phenol-chloroform extraction), selective precipitation of nucleic acids using high concentrations of salt or changes in pH to precipitate proteins, and nucleic acid precipitation using isopropanol or ethanol.

In other cases, nucleic acids can be isolated using methods that combine affinity immobilization with magnetic separation. For example, poly(A) mRNA may be bound to streptavidin-coated magnetic particles by biotin-labeled oligo(dT) and the particle complex removed from unbound contaminants using a magnet. Such methods can replace several centrifugation, organic extraction and phase separation steps with a rapid magnetic separation step.

In some cases, chromatography methods to isolate nucleic acids may utilize gel filtration, ion exchange, selective adsorption or affinity binding. For example, nucleic acids may be isolated from extracts by adsorption chromatography which relies on the nucleic acid-binding properties of silica or glass particles in the presence of chaotropic agents (see, e.g., U.S. Pat. Nos. 5,234,809 and 7,517,969, herein incorporated by reference). In certain cases, chromatography and affinity separation is used in combination to isolate nucleic acids from any given sample. For example, silica or glass coated magnetic particles may be added to a sample containing nucleic acids. Upon addition of a chaotropic agent, nucleic acids in the sample will bind to the silica or glass coating. Nucleic acids are then separated from unbound contaminants using a magnet. Suitable chaotropic agents are substances that disrupt the structure of, and denatures, macromolecules such as proteins and nucleic acids, and includes, e.g., butanol, ethanol, guanidinium chloride, guanidinium isothiocyanate, lithium perchlorate, lithium acetate, magnesium chloride, phenol, propanol, sodium dodecyl sulfate, thiourea, urea, and the like.

In certain embodiments, total nucleic acid may be isolated from a given sample by first lysing the sample so that nucleic acids are released into solution. Silica or glass coated magnetic particles are added to the lysed sample together with an effective amount of a chaotropic agent (e.g., 8 M guanidinium chloride), to allow nucleic acids to adsorb onto the surfaces of the magnetic particles. Several wash steps are performed and the nucleic acid-bound magnetic particles are optionally dried (e.g., using a heater). A release agent is added to release the nucleic acids from the magnetic particles. Nucleic acids are then eluted into a buffer of choice before proceeding to downstream processing (e.g., nucleic acid amplification and detection).

In some embodiments, total nucleic acid may be isolated from a given sample by using a method described in Jangam, et al., known as filtration isolation of nucleic acids (FINA) (Jangam, et al., J. Clin. Microbiol., 47(8), 2363-2368 (2009)). Generally, a method for isolation of HIV proviral DNA from leukocyte DNA from whole blood includes the use of a cell separation membrane disk placed in direct contact with an absorbent pad, which drives fluid flow by capillary pressure. Upon transfer of a sample of whole blood onto the disk, leukocytes and erythrocytes are trapped in the cell separation membrane, while plasma flows through into the absorbent pad. Membrane-entrapped cells are lysed, and cell debris etc., are wicked into the absorbent pad. The released nucleic acids are trapped within the membrane for further elution and processing.

In other cases, total nucleic acid may be isolated from a given sample by using commercially available nucleic acid isolation kits that result in isolated nucleic acids ready for downstream processing (e.g., amplification). For example, the commercially available Lyse-N-Go PCR reagent (Pierce) may be added to a given sample, which releases DNA for direct PCR amplification from bacteria, yeast, some animal and plant tissues, whole blood, and cultured mammalian cells.

In certain cases, extraction and purification of nucleic acids may be performed as described in Sur et al. J. Mol. Diagn., 2010, 12 (5): 620-628. A single pass of paramagnetic particles (PMPs), on which nucleic acids are adsorbed, through an immiscible hydrophobic liquid yields pure nucleic acid. Only two aqueous solutions are required: a lysis buffer, in which nucleic acids are captured on PMPs, and an elution buffer, in which they are released for amplification. The PMPs containing the nucleic acids are magnetically transported through a channel containing liquid wax that connects the lysis chamber to the elution chamber in a cartridge. Transporting PMPs through the immiscible phase yields DNA and RNA with equivalent purity as methods that utilize extensive wash steps.

In certain embodiments, extraction of nucleic acids from cells may be performed as described in U.S. Pat. No. 8,017,340, which is herein incorporated by reference in its entirety. Briefly, nucleic acids may be isolated by exposing a sample comprising cells containing nucleic acids to an aqueous mixture comprising a lytic reagent and one or more beads capable of binding the nucleic acid released from the cells to form a nucleic acid-bead complex; and passing the nucleic acid-bead complex through an immiscible liquid layer to separate the nucleic acid from the aqueous mixture, where the one or more beads are magnetic, and the nucleic acid-bead complex is passed through and separated from the immiscible liquid layer with an applied magnetic field. The immiscible liquid layer may be an organic liquid or a wax layer.

In certain embodiments, an integrated digital microfluidic and analyte detection device may find use in the detection of a target nucleic acid in a given sample, wherein the target nucleic acid is an RNA. In such cases, various RNA preparation methods are known to those skilled in the art, and are at least, generally, organic extraction methods, spin basket formats, magnetic particle methods, and direct lysis methods. Isolated RNA may then be reverse transcribed by various methods known in the art into DNA (e.g., cDNA) that can be further used in downstream processing and analysis.

Target Enrichment Methods

In some cases, once total nucleic acid that contains a target nucleic acid has been isolated from a given sample, a target enrichment step is performed to increase the concentration of the target nucleic acid within the sample (i.e., reduce the concentration of non-target contaminating materials). A target nucleic acid may be DNA or RNA. Target enrichment is performed using methods known to those skilled in the art. Such methods may involve a probe capture approach in which magnetic particles coated with capture probes are used. Additional methods for isolating nucleic acids will be recognized by those skilled in the art.

In certain cases, target enrichment is achieved by probe capture. A given sample of isolated total nucleic acid containing a target nucleic acid is mixed with magnetic particles coated with capture probes. Capture probes as used herein hybridize to the target nucleic acid under conditions that favor hybridization. The target nucleic acid-bound magnetic particles are washed and target nucleic acid is released and eluted.

In some cases, a target enrichment method of the present disclosure is a specific target enrichment method. A specific target enrichment method uses a capture probe that contains a sequence that hybridizes specifically to a target sequence in the target nucleic acid (e.g., see U.S. Pat. Nos. 6,110,678, 6,280,952, and 6,534,273). In general, a specific target enrichment method may use a capture probe made up of a target-specific sequence that hybridizes specifically to a target sequence in the target nucleic acid and a tail region that hybridizes to an immobilized probe (e.g., bound to a magnetic particle). The specific target capture method may use a two-step hybridization in which the first hybridization condition favors a solution-phase hybridization of the capture probe's target-specific sequence to the target sequence, and then a second hybridization condition that maintains the complex of the capture probe:target nucleic acid and allows hybridization of the capture probe's tail region to an immobilized probe on a support, forming on the support a complex made up of the immobilized probe, capture probe and target nucleic acid. The support and attached complex may then be separated from the other sample components that remain in the solution phase (e.g., by a magnet).

In some cases, a target enrichment method of the present disclosure is a non-specific target enrichment method. A non-specific target enrichment method of the present disclosure may make use of a capture probe that hybridizes nonspecifically to target nucleic acid in a sample by using alternative base pairing properties of a portion of the capture probe (compared to standard DNA or RNA hydrogen bonding) (see, e.g. U.S. Pat. No. 9,051,601).

In certain embodiments, the steps of total nucleic acid isolation from a given sample followed by target enrichment are carried out by one module of an integrated digital microfluidic and analyte detection device of the present disclosure. In some cases, these steps are carried out by systems that employ digital microfluidics, surface acoustic wave microfluidics, conventional microfluidics, and/or robotics, in ambient temperatures (e.g., room temperature). In some cases, total nucleic acid isolation from a given sample followed by target enrichment can be achieved in about 15 min, e.g., in about 10 min, 11 min, 12 min, 13 min, 14 min, 16 min, 17 min, 18 min, 19 min, 20 min, in at least 5 min, e.g., 20 min or more, 25 min or more, 30 min or more.

In certain embodiments, isolated total nucleic acid is transferred to a location in which target enrichment occurs. This may be done manually, or through automated methods, e.g., digital microfluidics, surface acoustic wave microfluidics, conventional microfluidics, and/or robotics.

Target Amplification Methods

Nucleic acid containing the target nucleic acid may be obtained by using an integrated device as described herein or by using a standard nucleic acid isolation procedure known in the art which procedure may be performed manually, automatically (e.g., robotically), or by a combination thereof. Upon isolation of a target nucleic acid (as present in an isolated nucleic acid preparation), wherein the target nucleic acid can be DNA or RNA, target amplification may be performed to amplify the target to concentrations that are detectable by analyte detection device (such as, an integrated digital microfluidic and analyte detection device) of the present disclosure. Nucleic acid amplification may be achieved by various formats, e.g., exponential amplification, asymmetric amplification, linked linear amplification, ligation-based amplification and transcription-based amplification. Polymerase chain reaction is an example of exponential nucleic acid amplification (see, U.S. Pat. No. 4,582,788 herein incorporated by reference). Ligation-based amplification, e.g., ligation amplification reaction (LAR), is described in Wu et al., Genomics, 1989. 4(4):560-569. As noted herein, target amplification may also be carried out on a sample in which the cells have been lysed to release the total nucleic acid in absence of purification of the total nucleic acid. The total nucleic acid may be genomic DNA or genomic RNA (e.g., nuclear DNA, mitochondrial DNA, viral DNA, viral RNA) or transcribed RNA. A "polynucleotide" means a single strand or a double-stranded nucleic acid. The term "oligonucleotide" refers to short polynucleotides, generally, no greater than about 50 nucleotides.

"Primer" refers to a polynucleotide that is capable of specifically hybridizing to a designated polynucleotide template and providing a point of initiation for synthesis of a complementary polynucleotide. Such synthesis occurs when the polynucleotide primer is placed under conditions in which synthesis is induced, i.e., in the presence of nucleotides, a complementary polynucleotide template, and an agent for polymerization such as a polymerase. A primer is typically single-stranded, but may be double-stranded. Primers are typically deoxyribonucleic acids, but a wide variety of synthetic and naturally occurring primers are useful for many applications. A primer is complementary to the template to which it is designed to hybridize to serve as a site for the initiation of synthesis, but need not reflect the exact sequence of the template. In such a case, specific hybridization of the primer to the template depends on the stringency of the hybridization conditions. As noted herein primers can include a tag that can be bound by a binding member. "Probe" refers to a polynucleotide that is capable of specifically hybridizing to a designated sequence of another polynucleotide. A probe specifically hybridizes to a target complementary polynucleotide, but need not reflect the exact complementary sequence of the template. In such a case, specific hybridization of the probe to the target depends on the stringency of the hybridization conditions.

In some cases, target amplification can be achieved by various polymerase chain reaction (PCR) methods known to a person skilled in the art, a method based on multiple cycles of denaturation, hybridization of two oligonucleotide primers, each to opposite strands of the target nucleic acid, and primer extension by a nucleotide polymerase to produce multiple double stranded copies of the target nucleic acid. Many variations of PCR have been described, and is used for amplification of DNA or RNA nucleic acid sequences, sequencing, mutation analysis and others. Thermocycling-based methods that employ a single primer have also been described. Other methods that are dependent on thermal cycling are the ligase chain reaction (LCR) and the related repair chain reaction (RCR). Target nucleic acid amplification in the thermal cycling based methods is carried out through multiple cycles of incubations at various temperatures.

In certain embodiments, isothermal target amplification methods are used to amplify target nucleic acid sequences for detection by an integrated digital microfluidic and analyte detection device of the present disclosure. Isothermal target amplification methods do not require a thermocycler, and can be easily adapted and integrated into systems and devices of the present disclosure. As used interchangeably herein, "isothermal amplification reaction", "isothermal target amplification" and other variations, refers to a target amplification reaction, wherein the temperature does not significantly change during the reaction, i.e. the target amplification reaction is carried out substantially at a single temperature. The temperature of an isothermal amplification reaction does not change over the course of the reaction by more than, e.g., 10° C., 9° C., 8° C., 7° C., 6° C., 5° C., 4° C., 3° C., 2° C., 1° C.

Depending on the method of isothermal amplification of nucleic acids, different enzymes are required for the amplification reaction. Known isothermal methods for amplification of nucleic acids are e.g., helicase-dependent amplification (HDA) (Vincent et al, EMBO reports, 2004. 5(8): 795-800), thermostable HDA (tHDA) (An et al, J. Biol. Chem., 2005. 280(32): 28952-28958), strand displacement amplification (SDA) (Walker et al, Nucleic Acids Res, 1992. 20(7):1691-6), multiple displacement amplification (MDA) (Dean et al, Proc. Natl. Acad. Sci., 2002. 99(8): 5261-5266), rolling circle amplification (Liu et al, J. Am. Chem. Soc., 1996 118:1587-1594), single primer isothermal amplification (SPIA) (Dafforn et al, Biotechniques, 2004. 37(5):854-7), restriction aided RCA (Wang et al, Genome Res., 2004. 14:2357-2366), transcription mediated amplification (TMA) (Vuorinen et al, J. Clin. Microbiol., 1995. 33:1856-1859), Nucleic Acid Sequence Based Amplification (NASBA) (Kievits et al, J. Virol. Methods, 1991. 35:273-286) and amplification reactions using nicking enzymes, e.g., nicking enzyme amplification reaction (NEAR) (U.S. Patent Application No. US2009017453), amplification reactions using recombination proteins, e.g., recombinase polymerase amplification (RPA) (Piepenburg et al, PLoS Biol., 2004. 4(7): e204), and Loop-mediated isothermal amplification (LAMP) (Notomi et al, Nucleic Acids Res., 2000. 28(12): e63) wherein the at least one mesophilic enzyme for amplifying nucleic acids under isothermal conditions is selected from the group consisting of helicase, mesophilic polymerases, mesophilic polymerases having strand displacement activity, nicking enzymes, recombination proteins, ligases, glycosylases and nucleases.

In some embodiments, amplification of a target nucleic acid for subsequent detection on an integrated digital microfluidic and analyte detection device of the present disclosure is achieved by recombinase polymerase amplification (RPA) (see, U.S. Pat. Nos. 7,270,981; 7,485,428 and 8,460,875 herein incorporated by reference). RPA is a single tube isothermal amplification reaction. In some cases, reverse transcriptase can be added to an RPA reaction in order to amplify RNA targets. RPA methods employ three enzymes: a recombinase, a single-stranded DNA binding protein (e.g., E. coli SSB) and a strand-displacing polymerase. Generally: first, a recombinase agent is contacted with a first and a second nucleic acid primer to form a first and a second nucleoprotein primer. Second, the first and second nucleoprotein primers are contacted to a double stranded target nucleic acid sequence to form a first double stranded structure at a first portion of said first strand and form a double stranded structure at a second portion of said second strand so the 3' ends of said first nucleic acid primer and said second nucleic acid primer are oriented towards each other on a given template nucleic acid molecule. Third, the 3' end of said first and second nucleoprotein primers are extended by a strand-displacing polymerase to generate first and second double stranded nucleic acids, and first and second displaced strands of nucleic acid. The second and third steps are repeated until a desired degree of amplification is achieved. A person skilled in the art will be able to recognize and carry out variations on the general RPA method as described above.

A recombinase agent is an enzyme that can coat single-stranded DNA (ssDNA) to form filaments, which can then scan double-stranded DNA (dsDNA) for regions of sequence homology. When homologous sequences are located, the nucleoprotein filament (comprising the recombinase agent) strand invades the dsDNA creating a short hybrid and a displaced strand bubble known as a D-loop. Suitable recombinase agents include the E. coli RecA protein or any homologous protein or protein complex from any phyla. These RecA homologues are generally named Rad51 after the first member of this group to be identified. Other recombinase agents may be utilized in place of RecA, for example as RecT or RecO. Recombinase agents generally require the presence of ATP, ATPγS, or other nucleoside triphosphates and their analogs. Recombinase agents are commonly used in a reaction environment in which regeneration of targeting sites can occur shortly following a round of D-loop stimulated synthesis. This will avoid a stalling of amplification or inefficient linear amplification of ssDNA caused by oscillating single-sided synthesis from one end to the other.

In some embodiments, amplification of a target nucleic acid for subsequent detection on an integrated digital microfluidic and analyte detection device of the present disclosure is achieved by loop-mediated isothermal amplification (LAMP). LAMP is described in U.S. Pat. No. 6,410,278, herein incorporated by reference. Generally, LAMP uses 4-6 primers recognizing 6-8 distinct regions of the target nucleic acid. A strand-displacing DNA polymerase initiates synthesis and two of the primers form loop structures to facilitate subsequent rounds of amplification. A person skilled in the art will be able to recognize and carry out variations on the general LAMP method as described above.

In some embodiments, amplification of a target nucleic acid for subsequent detection on an integrated digital microfluidic and analyte detection device of the present disclosure is achieved by helicase-dependent amplification (HDA). HDA is based on the unwinding activity of a DNA helicase.

HDA relies on one or more helicases to separate (melt, or unwind) two strands of a target nucleic acid duplex. HDA further utilizes a DNA or RNA polymerase to extend primers which are hybridized to single stranded nucleotide sequences to form complementary primer extension products. This process repeats itself so that exponential amplification can be achieved at a single temperature. A person skilled in the art will be able to recognize and carry out variations on the general HDA method as described above. "Complementary" as used herein refers to the complementarity between two nucleic acids, e.g., two DNA molecules. When a nucleotide position in both of the molecules is occupied by nucleotides normally capable of base pairing with each other, then the nucleic acids are considered to be complementary to each other at this position. Thus, two nucleic acids are complementary to each other when a substantial number (at least 50%) of corresponding positions in each of the molecules are occupied by nucleotides which normally base pair with each other (e.g., A:T and G:C nucleotide pairs).

"Helicase" as used herein refers to any enzyme capable of enzymatically unwinding a double stranded nucleic acid. Any helicase that translocates along DNA or RNA in a 5' to 3' direction or in the opposite 3' to 5' direction may be used. This includes helicases obtained from prokaryotes, viruses, archaea, and eukaryotes or recombinant forms of naturally occurring enzymes as well as analogues or derivatives having the specified activity. Examples of naturally occurring DNA helicases, described by Kornberg and Baker in chapter 11 of their book, DNA Replication, W. H. Freeman and Company ($2^{nd}$ ed. (1992)), include *E. coli* helicase I, II, III, & IV, Rep, DnaB, PriA, PcrA, T4 Gp41 helicase, T4 Dda helicase, T7 Gp4 helicases, SV40 Large T antigen, yeast RAD. Additional helicases that may be useful in HDA include RecQ helicase (Harmon and Kowalczykowski, J. Biol. Chem., 2001. 276:232-243), thermostable UvrD helicases from *T. tengcongensis* and *T. thermophilus* (Collins and McCarthy, Extremophiles. 2003, 7:35-41), thermostable DnaB helicase from *T. aquaticus* (Kaplan and Steitz, J. Biol. Chem., 1999. 274:6889-6897), and MCM helicase from archaeal and eukaryotic organisms (Grainge et al, Nucleic Acids Res., 2003. 31:4888-4898).

In certain embodiments, isolated total nucleic acid and/or enriched target nucleic acid is transferred to a location in which target amplification occurs. This may be done manually, or through automated methods, e.g., digital microfluidics, surface acoustic wave microfluidics, conventional microfluidics, and/or robotics.

In certain embodiments, the steps of target amplification of a target nucleic acid sequence are carried out by one module of an integrated digital microfluidic and analyte detection device of the present disclosure. In some cases, these steps are carried out by automated systems that employ digital microfluidics, surface acoustic wave microfluidics, conventional microfluidics, and/or robotics, at temperatures that allow for target amplification. Generally, these automated systems perform steps comprising: i) transferring isolated and/or enriched target nucleic acid, ii) adding enzymes and labelled primers or probes to a reaction tube or microfluidic chamber, iii) adding activators if necessary for target amplification, iv) heating the reaction mixture and v) optionally, quenching the amplification reaction. Systems that carry out the steps of target amplification in an isothermal target amplification reaction are substantially held at a single temperature, depending on the optimal temperature enzymes of various isothermal amplification reactions operate at. In some cases, target amplification carried out by an integrated digital microfluidic and analyte detection device of the present disclosure can employ the RPA method, wherein the target amplification module of the integrated device is held at substantially a single temperature, e.g., at about 37° C., e.g., 35-37° C., 37-39° C., 36-38° C., 35-39° C., 32-42° C. For other isothermal methods, the integrated device is held at a substantially single temperature, e.g., at a temperature of 40° C., or higher, e.g., 50° C.-70° C., such as 60° C.-65° C. In some cases, target amplification of a target nucleic acid sequence is carried out within 30 min, e.g., in about 25 min, 35 min, 27 min, 29 min, 31 min, 33 min, in at least 10 min e.g., 15 min or more, 20 min or more, 30 min or more.

In some cases, amplification of a target nucleic acid sequence is performed for a period of 30 min or less, e.g., 5 min, 10 min, 15 min, 20 min, or 25 min, e.g., 5 min-30 min, 5 min-25 min, 5 min-20 min, 5 min-25 min, 5 min-10 min, 10 min-30 min, 10 min-25 min, 10 min-20 min, 15 min-30 min, 15 min-25 min, or 15 min-20 min.

In some embodiments, amplification of a target nucleic acid is performed by isothermal amplification, e.g., LAMP, where the amplification is performed for 10 min or less, e.g., 9 min, 8 min, 7 min, 6 min, 5 min, 4 min, 3 min, 2 min, 1 min, 30 sec, 15 sec, or less, e.g., 15 sec-10 min, 30 sec-10 min, 1 min-10 min, 1 min-5 min, or 5 min-10 min.

In certain embodiments, the NAT methods disclosed herein detect a target nucleic acid present at a concentration as low as 1 aM. In certain embodiments, the NAT methods disclosed herein detect a target nucleic acid present at a concentration of at least 1 aM or more, e.g., 10 aM, 100 aM, 1 fM, 10 fM, 100 fM, 1 pM, 10 pM, 100 pM, or more. In certain embodiments, the NAT methods disclosed herein detect an amplification product generated from a target nucleic acid, where the amplification product is present at a concentration of 25 aM-10 fM. Thus, the presently disclosed detection methods can detect a target nucleic acid present in a sample at a concentration of less than 1 aM, prior to amplification. In most instance, an amplification of only 15 times, 10 times, 5 times, 2 times or no amplification is needed to provide sufficient quantities of the target nucleic acid for detection.

In certain embodiments, the disclosed methods can detect an amplification product produced from increasing copy number of the target nucleic acid by amplification, where as low as 1000 molecules of the amplification product are produced. Thus, in certain embodiments, a method for detecting presence of a target nucleic acid in a fluid sample may include amplifying the target nucleic acid in the sample by amplification to generate as low as 1000 molecules of an amplification product, wherein the amplifying incorporates a tag into the amplification product; capturing the amplification product on a plurality of capture objects comprising a binding member that specifically binds to the tag thereby generating a complex comprising capture object-amplification product; detectably labeling the amplification product in the complex to generate a detectably labeled complex; spatially segregating the capture objects into a plurality of wells such that each well contains no more than one capture object; and detecting the presence of the detectably labeled complex in the plurality of wells.

Figure 20A:
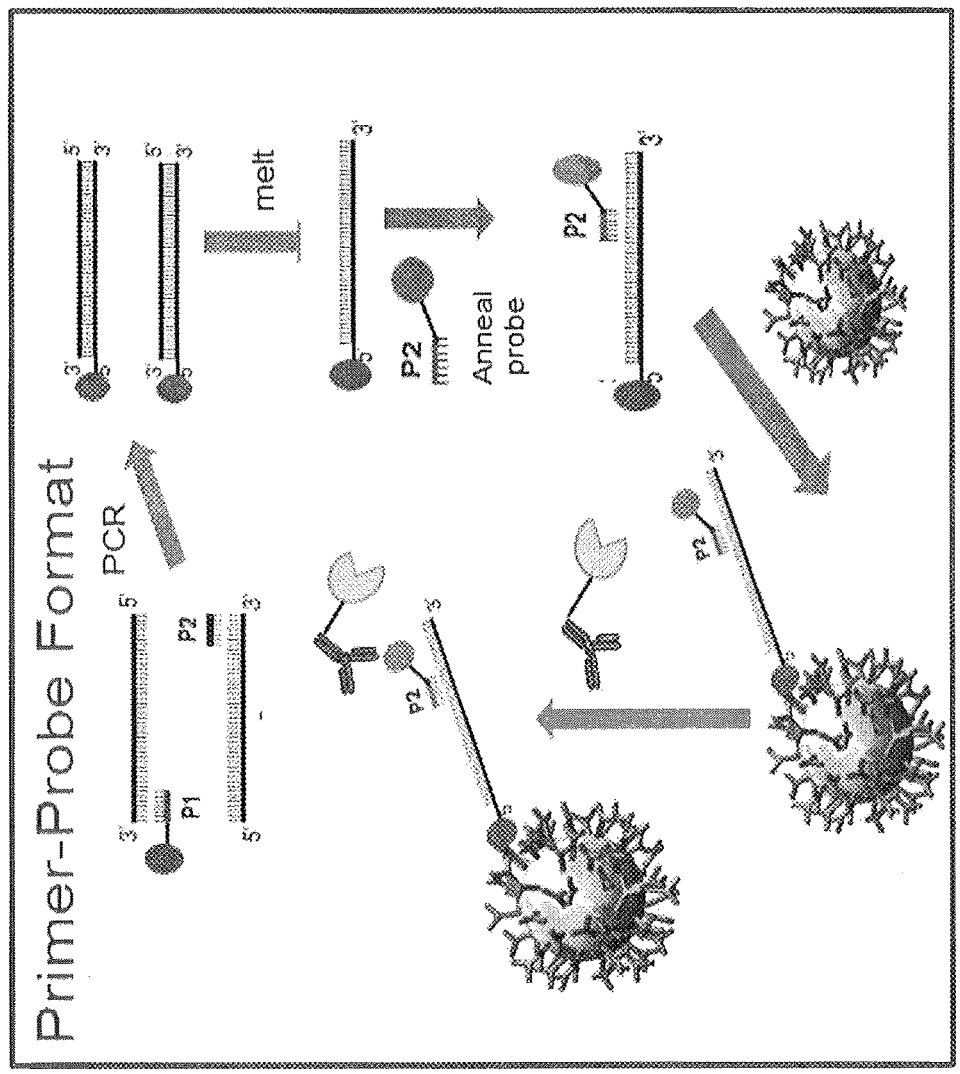
FIGS. 20A-20C depict exemplary labeling methods for digital detection of nucleic acid.
Figure 20B:
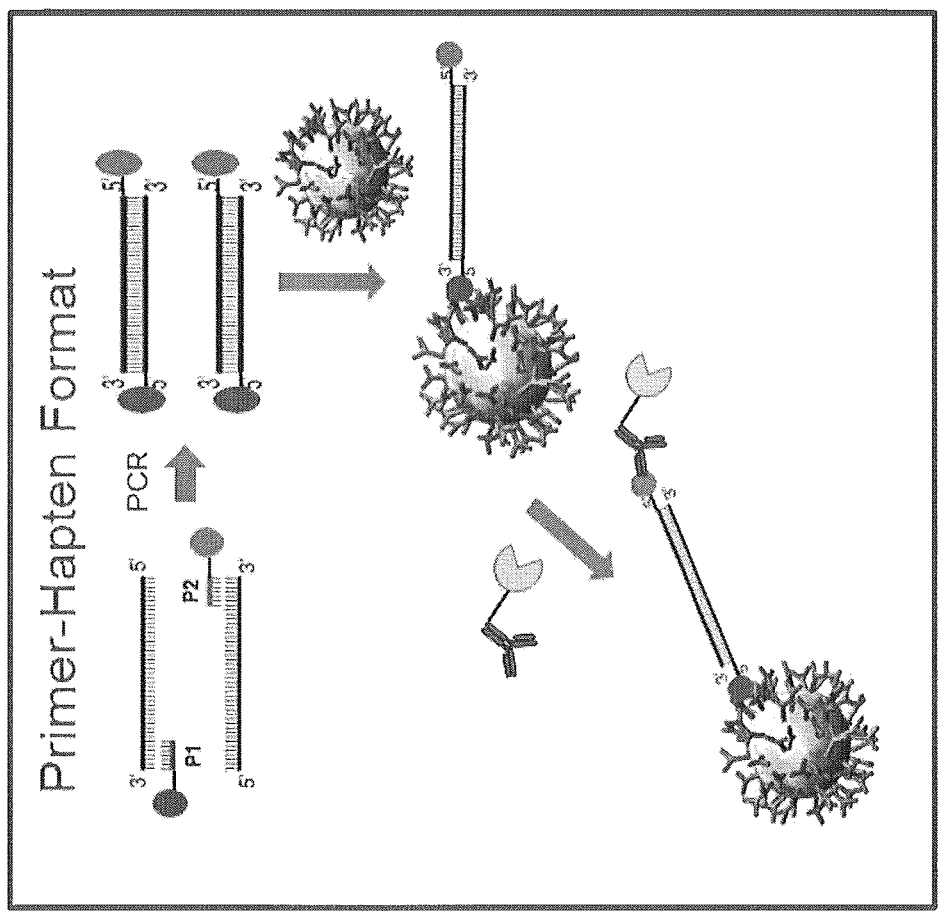
Figure 20C:
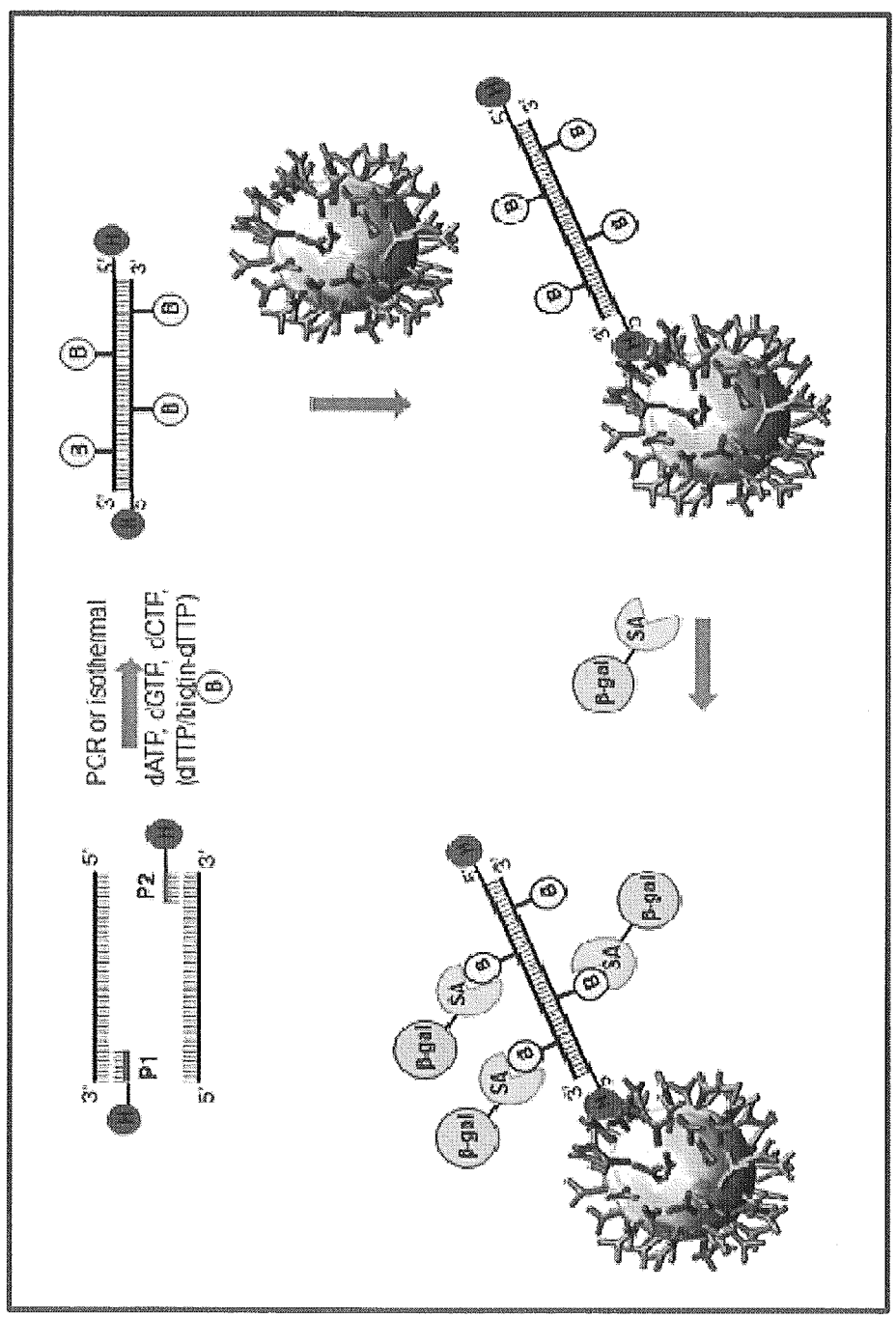

The primers or nucleotides used for the amplification reaction may be include a tag, such as, a hapten for incorporation of the tag into the amplified target nucleic acid. Any suitable tag may be utilized. For example, the tag may be a hapten for which a binding member that specifically binds to the hapten is available. For example, the hapten may be a small molecule for which antibodies that specifically bind to the hapten are available. Exemplary haptens include, avidin, biotin, digoxygenin, dinitrophenyl, dansyl-X, and derivatives thereof. In certain embodiments, the hapten may not be directly optically detectable, i.e., the hapten may not be a dye or a fluorescent molecule because such a hapten may interfere with the digital counting. Exemplary amplification formats for producing tagged amplification products are shown in FIGS. 20A-20C.

Assay Processing and Detection

Once a desired degree of target nucleic acid sequence amplification is achieved, the amplification product is transferred to an assay processing module (described above) of an integrated digital microfluidic and analyte detection device of the present disclosure. Various formats of assay processing can be employed. For example, an immunoassay can be performed to capture target amplified nucleic acid sequences using the tag incorporated into the amplified target nucleic acid. It is notable that the NAT methods disclosed herein do not utilize hybridization of nucleic acid sequences to capture the amplified nucleic acid sequence on a capture object. In other words, the capture object (such as, a bead, e.g., a magnetic bead) does not include a capture nucleic acid that is complementary to a sequence in the amplified target nucleic acid and can anneal to the amplified target nucleic acid. Rather, the capture object includes a binding member of a specific binding pair and captures the amplified target nucleic acid via interaction of the member of the binding pair with the other member of the binding pair, which other member that has been introduced into the amplified target nucleic acid during amplification. The members of a specific binding pair do not include nucleic acids that are complementary to each other. Thus, the capture object is not coated with a nucleic acid that can bind to the of the amplified target nucleic acid.

A number of immunoassay formats that generate a target nucleic acid related signal may be used. Exemplary immunoassay formats are depicted in FIGS. 20A-20C. In some embodiments, a sample droplet containing the target nucleic acid may be merged with a droplet containing magnetic beads on which a first binding member that specifically binds to the target nucleic acid present in the sample is attached. Merging creates a single droplet which may be incubated for a time sufficient to allow binding of the first binding member to a target nucleic acid present in the sample droplet. Optionally, the single droplet may be agitated to facilitate mixing of the sample with the first binding member. Mixing may be achieved by moving the single droplet back and forth, moving the single droplet around over a plurality of electrodes, splitting a droplet and then merging the droplets, or using SAWs, and the like. Next, the single droplet may be subjected to a magnetic force to retain the beads at a location in the device while the droplet may be moved away to a waste chamber or pad and replaced with a droplet containing a second binding member. The second binding member may be detectably labeled. The label may be any label that can be optically detected. The label may be a fluorescent label. An optional wash step may be performed, prior to adding the second binding member, by moving a droplet of wash buffer to the location at which the beads are retained using the magnetic force. The beads may or may not be resuspended in the wash buffer; a magnetic force is applied to the magnetic beads and the wash buffer is transported to a waste location. After a period of time sufficient for the second binding member to bind the analyte bound to the first binding member, the droplet containing the second binding member may be moved away while the beads are retained at the location. The beads may be washed using a droplet of wash buffer. Following the wash step, the magnetic force may be removed and a droplet containing the labeled beads which has a complex of the first binding member, analyte and the second binding member may be moved over to the detection module. As explained herein, the immunoassay may be carried out in the assay processing module. In certain cases, the assay processing for capturing and detectably labeling the amplified target nucleic acid may be carried out in the integrated microfluidics and analyte detection device as described herein. For example, in some embodiments, the assay processing for capturing and detectably labeling the amplified target nucleic acid may be performed in an integrated device depicted in FIGS. 1-14. The labeled beads may be allowed to settle into the array of wells in the detection module. The beads may settle using gravitational force or by applying electric or magnetic force. Following a wash step to remove any beads not located inside the wells, the wells may be sealed by using a hydrophobic liquid. For example, the labeled beads may be segregated into a plurality of wells which wells are sized to contain no more than one bead per well. The detection module containing the array of wells may include an analyte detection device illustrated in FIGS. 1-14. In some embodiments, the assay processing and detection may be carried out in an integrated device as described herein and with exemplary embodiments depicted in FIGS. 1-14.

In another embodiment, the second binding member may be attached to a particle or a bead via a cleavable linker. Following the wash step to remove any unbound second binding member, the particle or bead attached to the second binding member may be cleaved either chemically or by photocleavage. The cleaved particles/beads may be moved to the detection module and the particles/beads present in the wells quantitated.

In some cases, the particles/beads attached to the second binding member may be labeled. For example, the particles/beads may be color coded or fluorescent.

In another embodiment, the second binding member may be attached to a cleavable label. Following the wash step to remove any unbound second binding member, the label attached to the second binding member may be cleaved either chemically or by photocleavage. The cleaved label may be moved to the detection module, where the label is allowed to diffuse into the wells. Following removal of any label not deposited in the wells, the wells may be sealed with a hydrophobic fluid and the label may be quantitated.

A second immunoassay format that can generate a target nucleic acid related signal may also be used. In some embodiments, a sample droplet containing the target nucleic acid may be merged with a droplet containing labeled target nucleic acid or labeled competitor molecule to produce a single droplet. The labeled target nucleic acid or labeled competitor molecule competes with the target nucleic acid for binding to a first binding member. The label may be any label that can be optically detected. The label may be a fluorescent label. The single droplet may be agitated to facilitate mixing which may be achieved by moving the single droplet back and forth, moving the single droplet around over a plurality of electrodes, splitting a droplet and then merging the droplets, or using SAWs, and the like. The single droplet may then be merged with a droplet containing magnetic beads on which a first binding member that specifically binds the target nucleic acid and the labeled target nucleic acid (or the labeled competitor molecule) is attached. Merging creates a second single droplet which may be incubated for a time sufficient to allow either target nucleic acid or labeled target nucleic acid (or the labeled competitor molecule) present in the droplet to competitively bind with the first binding member. Optionally, the second single droplet may be agitated to facilitate mixing of the target nucleic acid-labeled target nucleic acid mixture with the first binding member. Next, the second single droplet may be subjected to a magnetic force to retain the beads at a location in the device while the droplet may then be moved away to a waste reservoir/pad and the beads may be contacted with a droplet containing a wash buffer. If a fluorescent label is used, the beads may be re-suspended in the wash buffer and then the beads may be moved over to the detection module.

If the label used is an enzyme, then a magnetic force is applied to capture the magnetic beads and the wash buffer is transported to a waste location. A droplet which contains enzyme substrate may be contacted with the magnetic beads which have a complex of the first binding member, analyte and labeled analyte. Optional mixing may be performed, after which the beads may be moved over to the detection module. As explained herein, the immunoassay may be carried out in the sample preparation module. The labeled beads may be allowed to settle into the array of wells in the detection module. The beads may settle using gravitational force or by applying electric or magnetic force. Following a wash step to remove any beads not located inside the wells, the wells may be sealed by using an immiscible liquid.

In certain cases, at least one of the binding members may be an aptamer, a nucleic acid, such as, DNA, RNA, oligonucleotides, and the like.

In certain embodiments, the binding member binds specifically to the target nucleic acid. By "specifically bind" or "binding specificity," refers to binding between members of a specific binding pair. The members of a specific binding pair bind to each other while not substantially binding to other molecules. For example, a specific binding pair of a hapten and an antibody is an antibody that binds the hapten with specificity sufficient to differentiate between the hapten and other components or contaminants of the test sample. For example, an antibody specific for an antigen binds to the antigen while does not bind significantly bind to other molecules under immunoassay conditions known to those of skilled in the art.

In certain embodiments, the steps of assay processing of a target nucleic acid sequence are carried out by one module of an integrated digital microfluidic and analyte detection device of the present disclosure. In some cases, these steps are carried out by automated systems that employ digital microfluidics, surface acoustic wave microfluidics, conventional microfluidics, and/or robotics, at temperatures that allow for target amplification. Systems and devices that carry out the steps of assay processing may be substantially held at a single temperature, depending on the optimal temperature enzymes used in assay processing operate at. In some cases, assay processing carried out by an integrated digital microfluidic and analyte detection device of the present disclosure can employ an immunoassay format, wherein the assay processing module of the integrated device is held at substantially a single temperature, e.g., at about 37° C., e.g., 35-37° C., 37-39° C., 36-38° C., 35-39° C., 32-42° C., 60-65° C. In some cases, assay processing is carried out within 20 min, e.g., in about 15 min, 25 min, 17 min, 19 min, 21 min, 23 min, in at least 5 min e.g., 10 min or more, 15 min or more, 20 min or more.

The placement of single nanobeads/nanoparticles/target nucleic acid molecules in the wells of a detection module allows for either a digital readout or analog readout. For example, for a low number of positive wells (≤~1% positive) Poisson statistics can be used to quantitate the target nucleic acid concentration in a digital format; for high numbers of positive wells (>~1%) the relative average intensities of signal-bearing wells are compared to the signal intensity generated from a single nanobead/nanoparticle/target nucleic acid molecule, respectively, and used to generate an analog signal. A digital signal may be used for lower target nucleic acid concentrations, whereas an analog signal may be used for higher analyte concentrations. A combination of digital and analog quantitation may be used, which may expand the linear dynamic range. As used herein, a "positive well" refers to a well that has a signal related to presence of a nanobead/nanoparticle/target nucleic acid molecule, which signal is above a threshold value. As used herein, a "negative well" refers to a well that may not have a signal related to presence of a nanobead/nanoparticle/target nucleic molecule. In certain embodiments, the signal from a negative well may be at a background level, i.e., below a threshold value. The placement of single nanobeads/nanoparticles/target nucleic acid molecules in the wells of a detection module can be achieved, e.g., using automation that employs digital microfluidics, surface acoustic wave microfluidics. Detection of a "positive" or "negative" well can be performed using various automated imaging systems known in the art.

Detection of a digital signal allows amplification time in a target amplification step to be reduced. A digital detection module of the present disclosure has a limit of detection of approximately at least 6,000 molecules, e.g., more than approximately 5,000 molecules, more than approximately 5,200 molecules, more than approximately 5,400 molecules, more than approximately 5,600 molecules, more than approximately 5,800 molecules, more than approximately 6,000 molecules. Using an isothermal target amplification method as described above (e.g., LAMP, RPA, and the like), the limit of detection of the digital detection module can be achieved in about 10 cycles of isothermal amplification, e.g., in about 5 cycles, in about 6 cycles, in about 7 cycles, in about 8 cycles, in about 9 cycles, in about 11 cycles, in about 12 cycles, in about 13 cycles, in about 14 cycles of isothermal amplification depending on the starting material. These numbers of cycles can be achieved in about 10-30 min of isothermal amplification, e.g. 1 min, 5 min, 10 min, 15 min, 20 min, 25 min, 30 min, 35 min, 40 min, about 15-25 min, about 15-20 min, about 20-25 min, about 25-30 min, about 5-10 min, about 10-15 min of isothermal amplification.

Isothermal amplification methods coupled with digital detection allows for ultrasensitive detection. It allows for approximately 16,000-fold enhanced sensitivity over amplification methods that required thermocycling coupled with analog detection. This enhanced sensitivity allows for approximately 45-80% less amplification time required.

Figure 18A:
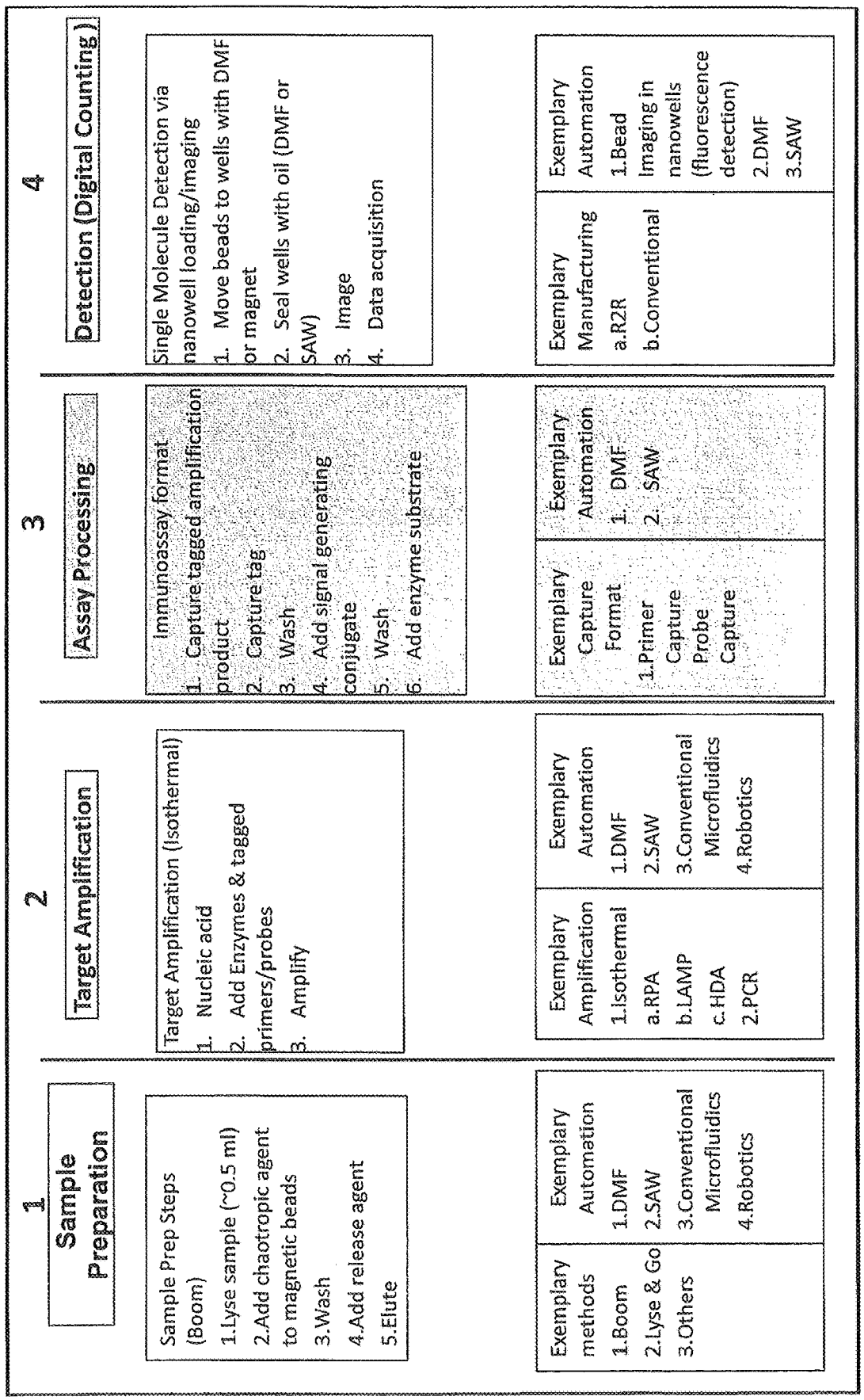
FIGS. 18A and 18B depict exemplary methods for nucleic acid testing (NAT).
Figure 18B:
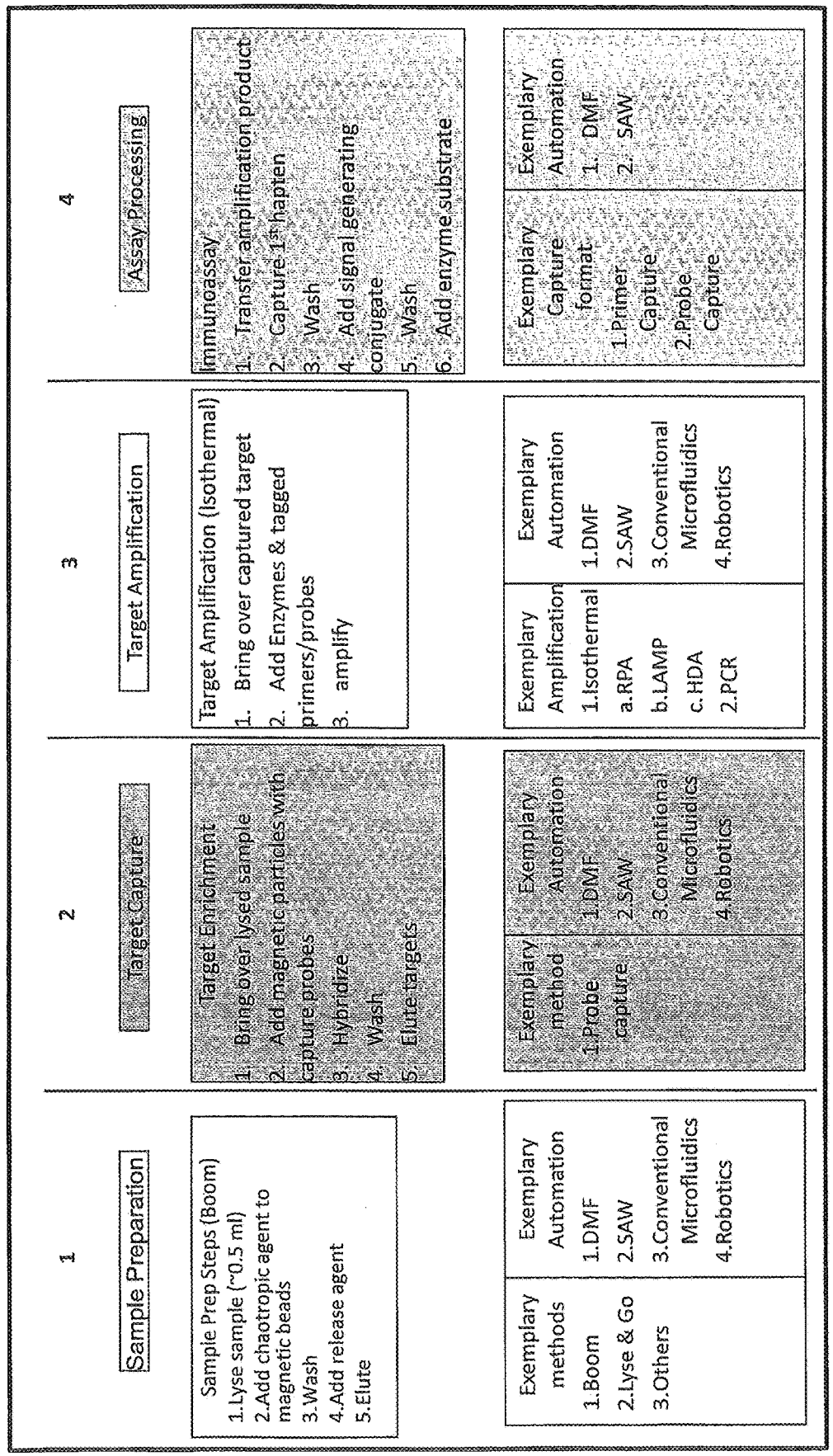

Exemplary embodiments of methods and devices for NAT are depicted in FIGS. 18A and 18B. FIG. 18A depicts NAT in which target capture step (enrichment) is not included. FIG. 18B depicts NAT utilizing a target enrichment step. The abbreviations are as follows: Digital microfluidics (DMF), surface acoustic waves (SAW), recombinase polymerase amplification (RPA), Loop-mediated isothermal amplification (LAMP), helicase-dependent amplification (HDA), reel-to-reel (R2R). FIG. 18A illustrates that NAT testing may be performed by utilizing four basic processes carried out sequentially in a device(s) as described herein. FIG. 18B illustrates that NAT testing may be performed by utilizing five basic processes carried out sequentially in a device(s) as described herein. As noted herein, FIG. 18B includes an optional target enrichment step. It is noted that in FIG. 18B, the next step after assay processing is the detection step illustrated in FIG. 18A. Step 1 of sample preparation for amplification of the target nucleic acid may be carried out using any suitable method. Exemplary methods are outlined in FIGS. 18A and 18B. Boom chemistry is described in R Boom, et al., J. Clin. Microbiol. March 1990 vol. 28 no. 3 495-503. In some cases, extraction and purification of nucleic acids may be performed as described in Sur et al. J. Mol. Diagn., 2010, 12 (5): 620-628. In some cases, separation of the nucleic acid from other cellular material may not be performed. Thus, the sample preparation step may simply include cell lysis to release the nucleic acid and the amplification of the target nucleic acid may be performed using the lysed sample. For example, the cells in a sample may be lysed using Lyse and Go PCR Reagent (Thermo Scientific) and the target nucleic acid amplified using an aliquot of the lysed sample. As noted in FIGS. 18A and 18B, the sample preparation step may be automated. Thus, the sample preparation may be performed using DMF or SAW as described herein. Sample preparation may also be carried out using a conventional microfluidics device or robotics.

The next step depicted in FIGS. 18A and 18B (after the optional target capture step) is the amplification of the target nucleic acid. While amplification methods are known in the art, exemplary amplification methods are depicted. The target amplification step may also be automated. Further, as explained in FIG. 19, in some embodiments, sample preparation and target nucleic acid amplification may be performed in performed in an integrated device.

Following target amplification, assay processing for immunoassay may be carried out as depicted in step 3 of FIG. 18A or step 4 of FIG. 18B. A primer capture format or a probe capture format may be used. In some examples, immunoassay may be performed as described in FIGS. 20A-20C. In certain cases, the amplification and tagging of the target nucleic acid may be carried out as described in U.S. Pat. No. 6,294,326. The assay processing step may also be automated.

Detection of the amplified target nucleic acid may be performed using digital counting. For example, the amplified target nucleic acid captured onto a capture object (e.g., beads, see step 4 in FIG. 18A) may be partitioned into nanowells and detected. As noted in FIG. 18A, the nanowells may be those available commercially. In some cases, the nanowells may be nanowells as described herein, such as, those manufactured using the roll-to-roll manufacturing process.

Target capture step depicted in FIG. 18B may be performed using any suitable technology. For example, target capture may be performed by using the methods described in U.S. Pat. No. 5,780,224 or 5,750,338.

Figure 19:
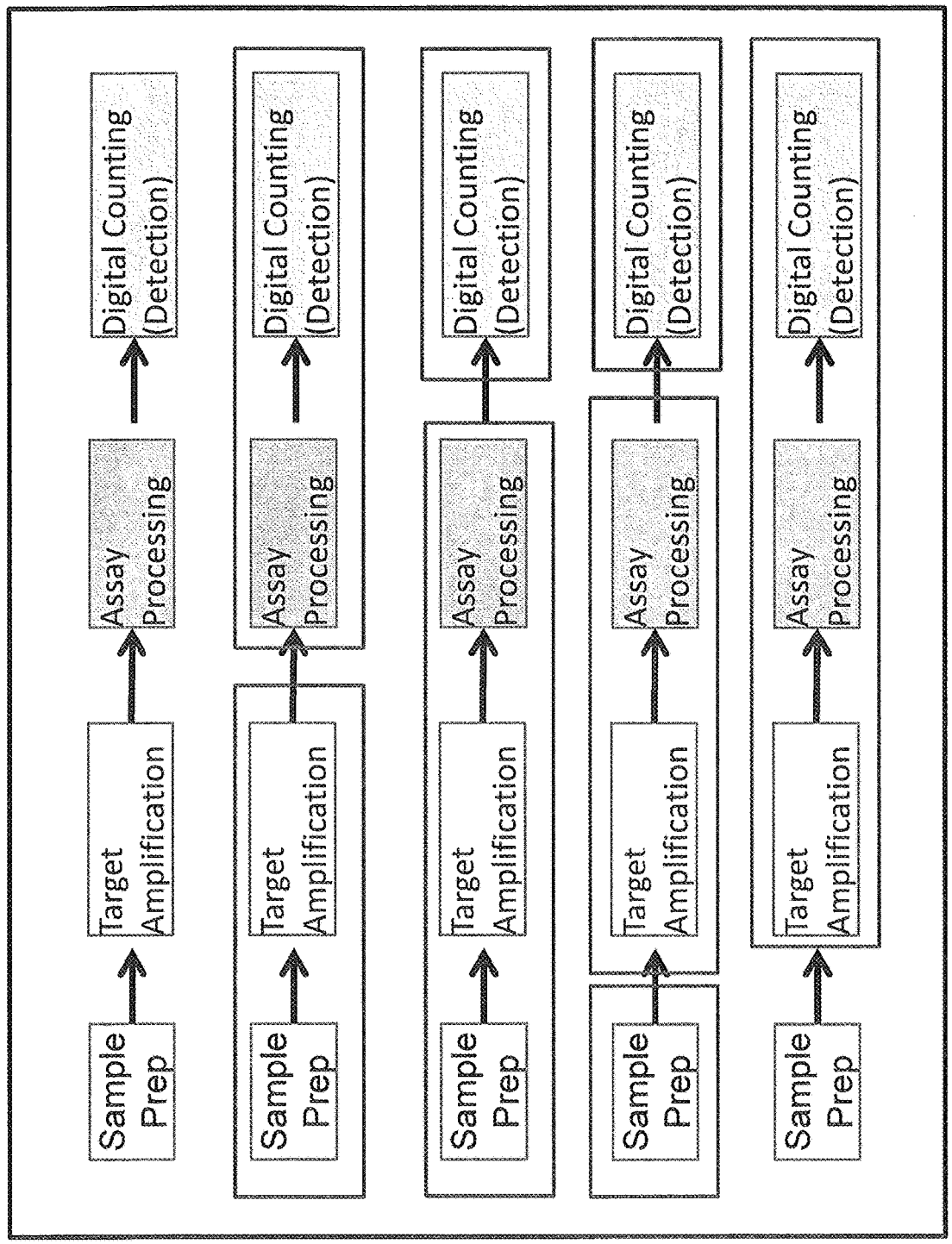
FIG. 19 depicts embodiment of integration of the modules for NAT.

Exemplary levels of integration of the modules for NAT are depicted in FIG. 19. Five exemplary embodiments are depicted. In a first embodiment, each of sample preparation, target amplification, assay processing, and digital counting is performed by a separate device and the end product from each device is transferred to the next device manually using for example, a robot. In a second embodiment, the sample preparation and target amplification are performed in an integrated device and assay processing and digital counting is performed on a separate integrated device. In a third embodiment, sample preparation, target amplification and assay processing are performed in an integrated device and digital counting is performed on a separate device. In a fourth embodiment, sample processing is carried out on a first device, target amplification and assay processing is carried out in an integrated device and digital counting is performed on a separate device. In a fifth embodiment, sample processing is carried out on a first device and target amplification, assay processing and digital counting are performed in a single integrated device.

Exemplary methods for converting a target nucleic acid into an immunologically detectable analyte is depicted in FIGS. 20A-20C. In FIG. 20A, an isolated target nucleic acid (e.g., in a purified solution of nucleic acid extracted from a sample) is amplified using a primer pair (P1 and P2). Primer P1 is conjugated to a first hapten at the 5'end while primer P2 is unlabeled. The amplification incorporates the P1 primer conjugated to the first hapten yielding nucleic acid labeled with the first hapten. The labeled nucleic acid is subsequently hybridized to a probe (after melting) that is conjugated to a second hapten. The labeled nucleic acid is captured on magnetic microparticles coated with a first antibody that specifically binds to the first hapten. After removing any unbound nucleic acid, the captured nucleic acid is contacted with a second antibody or a second molecule that binds to the second hapten. For example, the second hapten may be biotin and the second antibody may bind to biotin and may be conjugated to an enzyme that produces a detectable product. In another example, the detectable molecule may be biotin and the second molecule may be avidin (e.g., streptavidin) conjugated to $\square$-galactosidase, alkaline phosphatase or another enzyme. Any unbound second antibody or the second molecule may be removed and the magnetic microparticles exposed to a substrate for the enzyme and partitioned into a plurality of wells configured to contain no more than one microparticle. The wells may be sealed and the enzyme product, which is fluorescent, visualized with an optical detector capable of visualizing the microparticles in both white light and under excitation wavelengths for fluorescence detection (for detection of fluorescent reaction product). While not depicted in FIG. 20A, it is understood that nucleic acid labeled with the first and second haptens may be captured on microparticles that are coated with an antibody (or a molecule) that specifically binds to the second hapten. The first hapten may then be contacted with an antibody that specifically binds to the first hapten and is conjugated to an enzyme that catalyzes a reaction yielding a fluorescent molecule.

The amplified nucleic acid may be quantitated by determining the ratio of microparticles bound to the amplified nucleic acid and microparticles not bound to the amplified nucleic acid and using the Poisson equation to determine the number of targets nucleic acid detected on the array. In this manner, the target nucleic acid may be quantitated digitally.

In FIG. 20B, the target nucleic acid is amplified using a primer pair that amplifies a sequence in the target nucleic acid. Each of the primers P1 and P2 are conjugated at the 5'end to a first and a second hapten, respectively. The amplification yields nucleic acid that is labeled with both haptens. The labeled nucleic acid is captured using a magnetic bead coated with an antibody that binds to the first hapten. After removing any unbound nucleic acid, the nucleic acid attached to the beads is contacted with a second antibody that specifically binds to the second hapten. The second antibody may be conjugated to an enzyme that acts on a substrate to produce a fluorescent signal. The subsequent steps are as explained in the context of FIG. 20A. It is understood that the second hapten may be targeted for capture on the beads while the nucleic acid attached to the beads may be detected using an antibody (or another molecule) that binds to the first hapten. The antibody (or the other molecule) is conjugated to an enzyme that acts on a substrate to produce a fluorescent reaction product.

FIG. 20C depicts an alternate format for labeling of an amplified target nucleic acid for NAT. Isolated target nucleic acid is subjected to amplification using two primers P1 and P2 which are both labeled at the 5'end with a first hapten. Alternatively, only one of the primers may be labeled. During amplification, a labeled nucleotide triphosphate, such as biotin-16-aminoallyl-2'-dUTP (Trilink), can be included in the reaction mixture, where the ratio of unlabeled dUTP to labeled nucleotide can be changed, depending on the level of labeling desired in the final amplified product. After amplification, the target nucleic acid labeled with the first hapten is captured on magnetic microparticles coated with a capture antibody/a binding member, which specifically binds to the first hapten. Notably, the capture method does not utilize capture objects that are coated with a nucleic acid that hybridizes to the amplified target nucleic acid. Avoiding use of such capture objects avoids false positives that may arise from capture methods utilizing hybridization of nucleic acid sequences. After several washes to remove uncaptured material the beads are incubated with an enzyme-labeled conjugate molecule (i.e. streptavidin-beta-galactoside (SA-□-gal), or a similar detection molecule), which binds to the biotin moieties in the labeled target. The beads are washed again several times to remove any unbound material. An enzyme substrate is added, which produces a fluorescent product upon turnover with the enzyme conjugate. The beads are then deposited into femtoliter-sized nanowell arrays, with each nanowell holding a maximum of 1 bead. The wells are sealed and the fluorescent product is visualized with an optical detector, which is capable of visualizing beads in both white light and under excitation wavelengths for fluorescence detection.

In certain embodiments, the primers used to amplify a target nucleic acid may include a tag molecule and may generate tagged amplification products where the tag is incorporated at a 5' end of the amplified nucleic acid. In contrast, when a tag is introduced into the amplification product by incorporation of a tagged nucleotide, the tag may be incorporated into a plurality of regions of the amplified product, depending on the sequence of the target nucleic acid and the concentration level of the tagged nucleotide. In certain embodiments, a tagged probe may be annealed to the captured amplification product (e.g., to a first nucleic acid strand or a second strand). The probe may bind to any region of the amplification product.

As used herein, a first nucleic acid strand or a second nucleic acid strand refers to the two strands of a double stranded DNA.

As noted herein, members of a specific binding pair, especially wherein one member is bound to a capture object or a solid support (e.g., a bead) find use in the immunoassays described herein. Exemplary specific binding pairs include antibody-antigen; antibody-hapten; receptor-ligand; protein-co-factor; enzyme-co-factor and protein-ligand (such as biotin-streptavidin). One member of the specific binding pair is conjugated to a detectable moiety, e.g., an enzyme that produces a detectable reaction product.

In certain embodiments, the number of capture objects may be in excess of the number of amplified target nucleic acid sequences such that at most a single amplified target nucleic acid sequence (which may be single stranded or double stranded) is captured on a single capture object.

Targets are quantitated by determining the ratio of positive/negative beads and using the Poisson equation to determine the number of targets detected on the array. In this manner, the nucleic acid targets are quantitated digitally.

Any target nucleic acid of interest may be detected and/or quantitated by the methods disclosed herein. Any nucleic acid detected using standard NAT may be detected and/or measured by the disclosed methods. The target nucleic acid may be RNA or DNA. The target nucleic acid may be nucleic acid of a pathogen. For example, the target nucleic acid may be a viral RNA or DNA, a bacterial RNA or DNA, a fungal RNA or DNA. In certain embodiments, the virus may be human immunodeficiency virus (HIV), hepatitis B virus (HBV), hepatitis C virus (HCV), or the like. The target DNA or RNA may also be from eukaryotic cells and/or cell lines.

EXAMPLES

Example 1: Ribonucleic Acid Testing Using Digital Detection

This examples demonstrates that digital detection allows the amplification time to be reduced compared to the amplification time required for analog-based detection. Digital detection technology based on stochastic confinement of labeled target can detect approx. 6,000 molecules, whereas standard analog-based detection requires a minimum of approx. 90 million molecules.

In this example, a blood sample containing 50 copies of HIV per ml is used as the starting material. The 1 ml sample is subjected to RNA extraction/purification. The RNA extraction/purification may be carried out using Boom chemistry (R Boom, et al., J. Clin. Microbiol. March 1990 vol. 28 no. 3 495-503). For this example, the purified total RNA is resuspended in 1 ml of reverse transcription (RT) buffer in preparation for cDNA synthesis. The RT buffer contains a RT primer (specific or random), dNTP mixture, salt, and a reverse transcriptase (AMV RT, MMLV, or SuperScript, etc.). The reaction is allowed to proceed at a temperature range of 37° C. to 55° C., depending on the reverse transcriptase, for 10-60 minutes. It is assumed that the total reaction volume may be smaller than 1 ml, depending on the available concentration of target RNA. It is also comprehended that some level of amplification may occur during the cDNA step. After reverse transcription, the newly created cDNA target is ready to be transferred to the target amplification reaction.

The constituents that make up the amplification buffer are amenable to the amplification method (i.e., PCR, isothermal, etc.) and contain amplification primers (labeled and/or unlabeled), deoxynucleotide triphosphates (unlabeled and/or labeled), salt, and a DNA polymerase (i.e. Taq polymerase, Bst polymerase, or Klenow fragment, etc.). For isothermal amplification, other protein constituents may also be included. Approx. 150 ml of this buffer would contain approx. 8 copies or more of cDNA target.

The solution is subjected to subsequent rounds of exponential amplification, where the number of targets double with each amplification cycle until the target reaches the minimum number of copies required for detection. An example of PCR amplification conditions would include a melt step (i.e. ~94° C., ~10 sec), primer anneal step (i.e. ~60° C. (~5° C. below Tm of primers), ~20 sec), and extension step (i.e. ~72° C., ~20 sec). An example of isothermal amplification conditions includes a constant reaction temperature ranging from 30° to 65° for 10-30 minutes, depending on the isothermal amplification method. After amplification, amplified target is processed using standard immunoassay methods (i.e. immunocapture on solid support, wash steps, conjugate addition, etc.).

Digital detection is accomplished by transferring labeled beads from the processed sample into an array of femtoliter-sized nanowells such that each well contains no more than one bead, followed by sealing and optical detection of a fluorescent substrate. The array of femtoliter wells are imaged with a camera and the ratio of positive to negative beads is used to quantitate the target (for quantitative assays), or detect the presence of a target (for qualitative assays).

For comparison, analog detection is accomplished by running a TaqMan assay, for example, where the target is quantitated using threshold cycle. For qualitative assays, the presence of a target is determined by using a minimum threshold cycle (i.e. without quantitation).

For digital detection, the minimum (approx. 6,000 molecules) is reached in approx. 10 cycles of amplification, starting with approx. 8 copies; for analog-based detection, the minimum (90,000,000 molecules) is reached in approx. 24 amplification cycles. The difference of 14 cycles represents a sensitivity enhancement of approx. 16,400 over analog-based detection, with a time saving of 30-45 minutes.

Example 2: Deoxyribonucleic Acid Testing Using Digital Detection

This example demonstrates that digital detection allows detection of a lower number of target DNA than required for detection using analog-based detection. In this example, a blood sample containing 50 copies of HBV per ml is used as the starting material. The 1 ml sample is subjected to DNA extraction/purification using, for example, Boom chemistry. For this example, the purified total nucleic acid is resuspended in 1 ml of amplification buffer. The constituents that make up the amplification buffer are amenable to the amplification method (i.e. PCR, isothermal, etc.) and contain amplification primers (labeled and/or unlabeled), deoxynucleotide triphosphates (unlabeled and/or labeled), salt, and a DNA polymerase (i.e. Taq polymerase, Bst polymerase, Klenow fragment, etc.). For isothermal amplification, other protein constituents may be included. Approx. 150 ml of this buffer contains approx. 8 copies of DNA target.

The solution is subjected to subsequent rounds of exponential amplification, where the number of targets double with each amplification cycle until the target reaches the minimum number of copies required for detection. An example of PCR amplification conditions would include a melt step (i.e. ~94° C., ~10 sec), primer anneal step (i.e. ~60° C. (~5° C. below Tm of primers), ~20 sec), and extension step (i.e. ~72° C., ~20 sec). An example of isothermal amplification conditions would include a constant reaction temperature ranging from 30° C. to 65° C. for 10-30 minutes, depending on the isothermal amplification method. After amplification, amplified target is processed using standard immunoassay methods (i.e. immunocapture on solid support, wash steps, conjugate addition, etc.).

Digital detection is accomplished by transferring labeled beads from the processed sample into an array of femtoliter-sized nanowells such that each well contains no more than one bead, followed by sealing and optical detection of a fluorescent substrate. The array of femtoliter wells are imaged with a camera and the ratio of positive to negative beads is used to quantitate the target (for quantitative assays), or detect the presence of a target (for qualitative assays).

Analog detection is carried out by running a TaqMan assay, for example, where the target is quantitated using threshold cycle. For qualitative assays, the presence of a target is determined by using a minimum threshold cycle (i.e. without quantitation).

For digital detection, the minimum (6,000 molecules) is reached in approx. 10 cycles of amplification; for analog-based detection, the minimum (90,000,000 molecules) is reached in approx. 24 amplification cycles. The difference of 14 cycles represents a sensitivity enhancement of approx. 16,400 over analog-based detection, with a time saving of 30-45 minutes.

The difference in amplification required for digital detection vs. analog detection of a nucleic acid (RNA or DNA) is depicted in FIG. 21.

Example 3: Deoxyribonucleic Acid Testing Using Digital Detection

Figure 22:
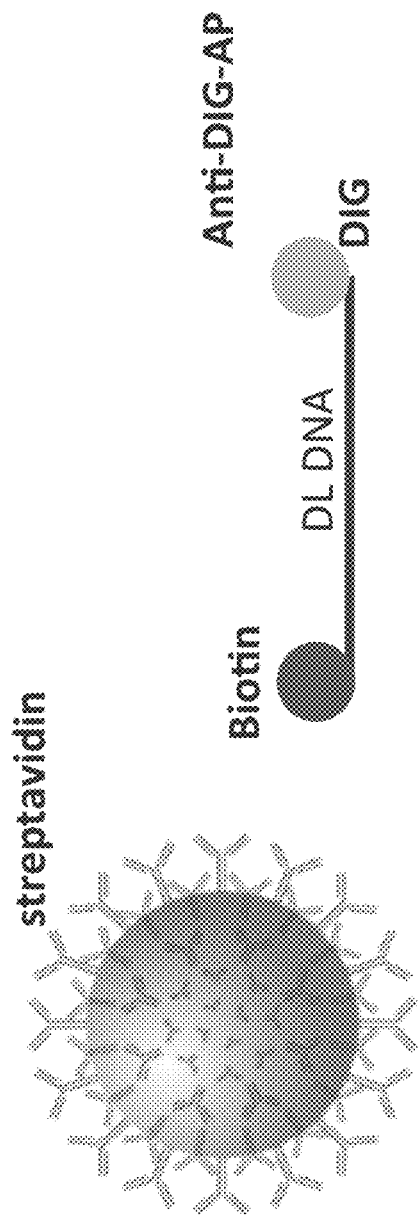
FIG. 22 depicts streptavidin coated beads and DNA double labeled (DL-DNA) with biotin and digoxygenin (DIG).
Figure 24:
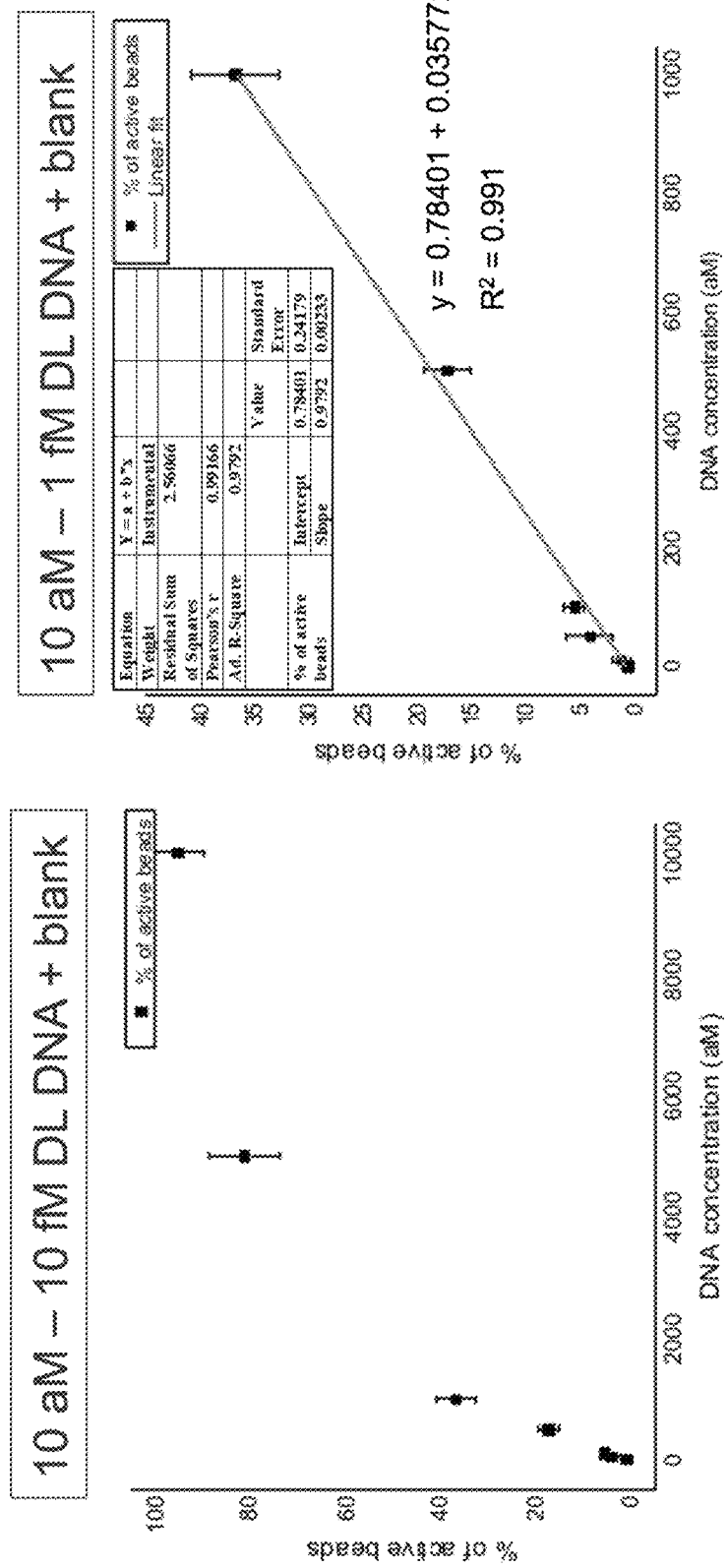
FIG. 24 shows a graph of percent of active beads (positive beads) as a function of increasing concentration of the DL-DNA.

In order to determine the limit of detection (LOD) of digital detection method utilizing capture of the target nucleic acid on beads and separation of the beads into an array of wells where each well contains no more than one bead, the target nucleic acid was synthesized chemically as a single stranded DNA and was double-labeled (DL) with biotin at one end and digoxygenin (DIG) at the opposite end. The DL single stranded DNA was captured on streptavidin coated beads which were detected by binding of alkaline-phosphatase (AP) labeled anti-DIG antibodies (see FIG. 22). The DL single stranded DNA present at a concentration of 100 aM (about 6000 molecules) was detectable (see FIG. 23). The LOD of method was about 24.6 aM (about 1481 molecules) (see FIG. 24).

140,000 beads were used for capture of DL DNA in a volume of 100 pl. The concentration of the DL DNA measured using the disclosed method was 10 fM (602,200 molecules), 5 fM (301,100 molecules), 1 fM (60,220 molecules), 500 aM (30,110 molecules), 100 aM (6,022 molecules), 10 aM (602 molecules), and 0 M. Average number of enzyme (i.e., AP labeled anti-DIG antibodies) per bead (AEB) was proportional to concentration of the target DL DNA. FIG. 23, $F_{off}$=fraction of beads that are negative; $F_{on}$=fraction of beads that are positive; expected signal=theoretical percentage of beads that are positive; measure signal=actual percentage of beads that are positive.

What is claimed is:

1. A method for detecting a target nucleic acid in a fluid sample, the method comprising:
   (a) amplifying the target nucleic acid in the sample to generate an amplification product,
   wherein the amplifying incorporates a tag into the amplification product,
   wherein the amplification comprises less than or equal to 15 cycles of amplification;
   (b) capturing the amplification product on a plurality of capture objects in droplets, each capture object comprising one or more binding members that specifically binds to the tag thereby generating a complex comprising capture object-amplification product;
   (c) detectably labeling the amplification product in the complex to generate a detectably labeled complex;
   (d) spatially segregating the droplets containing the capture objects into a plurality of wells such that each well contains no more than one capture object; and
   (e) detecting the presence of the detectably labeled complex in the plurality of wells, wherein the combination of the tag and the binding member that specifically binds to the tag is selected from the group consisting of antibody-antigen, antibody-hapten, receptor-ligand, protein-co-factor, enzyme-co-factor, and protein-ligand;

wherein the method is performed using an integrated digital microfluidic and analyte detection device comprising an amplification module and an analyte detection module, the amplification module is configured to perform the step (a); and the analyte detection module is configured to perform the steps (b) to (e), the analyte detection module comprising:

a first substrate and a second substrate, wherein the second substrate is positioned over the first substrate and is separated from the first substrate by a gap; the first substrate comprising: a series of electrodes positioned on an upper surface of the first substrate; a proximal portion at which the droplets containing the capture objects are introduced; an array of wells comprising the plurality of wells, wherein the array of wells is positioned in only a distal portion of the first substrate; and wherein the series of electrodes extend from the proximal portion to the distal portion of the first substrate, wherein the series of electrodes manipulate the droplets containing the capture objects and droplets containing reagents for labeling and detecting the amplification products to spatially segregate in step (d) the capture objects into the plurality of wells such that each well in the plurality of wells contains no more than one capture object.

2. The method of claim 1, wherein the amplification comprises less than 14 cycles of amplification.

3. The method of claim 1, wherein the amplification comprises less than 13 cycles of amplification.

4. The method of claim 1, wherein the amplification comprises less than 12 cycles of amplification.

5. The method of claim 1, wherein the amplification comprises less than 11 cycles of amplification.

6. The method of claim 1, wherein the amplification comprises less than 10 cycles of amplification.

7. The method of claim 1, wherein the amplification comprises 5-15 cycles of amplification.

8. The method of claim 1, wherein the amplification comprises 5-13 cycles of amplification.

9. The method of claim 1, wherein the amplification comprises 6-15 cycles of amplification.

10. The method of claim 1, wherein the amplification comprises 6-10 cycles of amplification.

11. The method of claim 1, wherein the amplification comprises 8-15 cycles of amplification.

12. The method of claim 1, wherein the amplification comprises 8-13 cycles of amplification.

13. The method of claim 1, wherein the amplification comprises 8-10 cycles of amplification.

14. The method of claim 1, wherein the amplification generates about 1000 molecules of the amplification products.

15. The method of claim 1, wherein the amplification generates about 3000 molecules of the amplification products.

16. The method of claim 1, wherein the amplification generates about 6000 molecules of the amplification products.

17. The method of claim 1, wherein the method further comprises determining a percentage of wells containing the detectably labeled complex, wherein the percentage of wells is used to determine a concentration of the target nucleic acid in the fluid sample.

18. The method of claim 1, wherein the method further comprises determining a measure of the concentration of the target nucleic acid in the fluid sample based at least in part on a measured intensity level of a signal of the delectably labeled complex in the wells.

19. The method of claim 1, wherein the method comprises prior to the capturing the amplification product on a plurality of capture objects:

denaturing the amplification product to generate a first nucleic acid strand and a second nucleic acid strand, wherein the first nucleic acid strand includes the tag, wherein the tag is a first tag;

annealing a probe to the first nucleic acid strand, wherein the probe is complementary to a segment of the first nucleic acid strand to generate a dual-tagged amplification product, wherein the probe comprises a second tag which is different from the first tag;

capturing the dual-tagged amplification product comprising the first nucleic acid strand comprising the first tag on the plurality of capture objects each comprising one or more binding members, which are first binding members that specifically bind to the first tag to generate a capture object-first nucleic acid complex;

contacting the capture object-first nucleic acid complex with a second binding member that specifically binds to the second tag in the probe, wherein the second binding member is detectably labeled, thereby generating the detectably labeled complex, and wherein the combination of the tag and the binding member that specifically binds to the tag is selected from the group consisting of antibody-antigen, antibody-hapten, receptor-ligand, protein-co-factor, enzyme-co-factor and protein-ligand.

20. The method of claim 1, wherein the amplification product comprises a first nucleic acid strand and a second nucleic acid strand and wherein the amplifying incorporates a first tag in the first nucleic acid strand and a second tag into the second nucleic acid strand, wherein the capturing the amplification product comprises:

a) capturing the first nucleic acid strand on a plurality of capture objects each comprising one or more first binding members that specifically bind to the first tag thereby generating the complex comprising capture object-amplification product, wherein detectably labeling the amplification product in the complex to generate the detectably labeled complex comprises:

contacting the complex with a second binding member that specifically binds to the second tag, wherein the second binding member is detectably labeled, thereby generating the detectably, labeled complex; or b) capturing the second nucleic acid strand on a plurality of capture objects each comprising one or more second binding members that specifically bind to the second tag thereby generating a complex comprising capture object-amplification product, wherein detectably labeling the amplification product in the complex to generate the detectably labeled complex comprises:

contacting the complex with a first binding member that specifically binds to the first tag, wherein the first binding member is detectably labeled, thereby generating the detectably labeled complex, and wherein the combination of the tag and the binding member that specifically binds to the tag is selected from the group consisting of antibody-antigen, antibody-hapten, receptor-ligand, protein-co-factor, enzyme-co-factor, and protein-ligand.

21. The method of claim 1, wherein a first nucleic acid strand in the amplification product comprises a first tag and wherein the plurality of capture objects each comprise one or more first binding members that specifically bind to the first tag and wherein the first nucleic acid strand comprises a plurality of nucleotides that comprise a second tag, wherein capturing the amplification product comprises contacting the amplification product with the plurality of capture objects each comprising the one or more first binding members to generate the complex comprising the capture object-amplification product, wherein the detectably labeling the amplification product in the complex to generate a detectably labeled complex comprises:

contacting the complex with a second binding member that specifically binds to the second tag, wherein the second binding member is detectably labeled, thereby generating the detectably labeled complex, and wherein the combination of the tag and the binding member that specifically binds to the tag is selected from the group consisting of antibody-antigen, antibody-hapten, receptor-ligand, protein-co-factor, enzyme-co-factor and protein-ligand.

22. The method of claim 1, wherein the detectably labeled complex comprises a signaling moiety that produces a detectable signal.

23. The method of claim 22, wherein the signaling moiety is an enzyme that acts on a substrate to produce a detectable signal.

24. A method for detecting a target nucleic acid in a fluid sample, the method comprising:
  (a) amplifying the target nucleic acid in the sample to generate an amplification product,
  wherein the amplifying incorporates a tag into the amplification product,
  wherein the amplification is performed for a period of time less than 10 minutes;
  (b) capturing the amplification product on a plurality of capture objects in droplets, each comprising one or more binding members that specifically binds to the tag thereby generating a complex comprising capture object-amplification product;
  (c) detectably labeling the amplification product in the complex to generate a detectably labeled complex;
  (d) spatially segregating the droplets containing the capture objects into a plurality of wells such that each well contains no more than one capture object;
  (e) detecting the presence of the detectably labeled complex in the plurality of wells,
  wherein the combination of the tag and the binding member that specifically binds to the tag is selected from the group consisting of antibody-antigen, antibody-hapten, receptor-ligand, protein-co-factor, enzyme-co-factor, and protein-ligand;
  wherein the method is performed using an integrated digital microfluidic and analyte detection device comprising an amplification module and an analyte detection module,
  the amplification module is configured to perform the step (a); and
  the analyte detection module is configured to perform the steps (b) to (e), the analyte detection module comprising:
  a first substrate and a second substrate, wherein the second substrate is positioned over the first substrate and is separated from the first substrate by a gap; the first substrate comprising: a series of electrodes positioned on an upper surface of the first substrate; a proximal portion at which the droplets containing the capture objects are introduced; an array of wells comprising the plurality of wells, wherein the array of wells is positioned in only a distal portion of the first substrate; and wherein the series of electrodes extend from the proximal portion to the distal portion of the first substrate,
  wherein the series of electrodes manipulate the droplets containing the capture objects and droplets containing reagents for labeling and detecting the amplification products to spatially segregate in step (d) the capture objects into the plurality of wells such that each well in the plurality of wells contains no more than one capture object.

25. The method of claim 24, wherein the amplification is performed for a period of time of 1-5 minutes.

26. A method for detecting a target nucleic acid in a fluid sample, the method comprising:
  (a) amplifying the target nucleic acid in the sample to generate as low as 1000 molecules of an amplification product,
  wherein the amplifying incorporates a tag into the amplification product,
  (b) capturing the amplification product on a plurality of capture objects in droplets, each comprising one or more binding members that specifically binds to the tag thereby generating a complex comprising capture object-amplification product;
  (c) detectably labeling the amplification product in the complex to generate a detectably labeled complex;
  (d) spatially segregating the droplets containing the capture objects into a plurality of wells such that each well contains no more than one capture object; and
  (e) detecting the presence of as low as 1000 molecules of the amplification product in the detectably labeled capture object-amplification product complex in the plurality of wells,
  wherein the combination of the tag and the binding member that, specifically binds to the tag is selected from the group consisting of antibody-antigen, antibody-hapten, receptor-ligand, protein-co-factor, enzyme-co-factor, and protein-ligand;
  wherein the method is performed using an integrated digital microfluidic and analyte detection device comprising an amplification module and an analyte detection module,
  the amplification module is configured to perform the step (a); and
  the analyte detection module is configured to perform the steps (b) to (e), the analyte detection module comprising:
  a first substrate and a second substrate, wherein the second substrate is positioned over the first substrate and is separated from the first substrate by a gap; the first substrate comprising: a series of electrodes positioned on an upper surface of the first substrate; a proximal portion at which the droplets containing the capture objects are introduced; an array of wells comprising the plurality of wells, wherein the array of wells is positioned in only a distal portion of the first substrate; and wherein the series of electrodes extend from the proximal portion to the distal portion of the first substrate, wherein the series of electrodes manipulate the droplets containing the capture objects and droplets containing reagents for labeling and detecting the amplification products to spatially segregate in step (d) the capture objects into the plurality of wells such that each well in the plurality of wells contains no more than one capture object.

27. The method of claim 26, comprising detecting presence of as low as 2000 molecules of the amplification product.

28. The method of claim 26, further comprising detecting the presence of as low as 3000 molecules of the amplification product.

29. The method of claim 26, further comprising detecting the presence of as low as 6000 molecules of the amplification product.

30. A method for detecting a target nucleic acid in a fluid sample, the method comprising:
(a) amplifying the target nucleic acid in the sample to generate an amplification product at a concentration as low as 10 aM,
wherein the amplifying incorporates a tag into the amplification product,
(b) capturing the amplification product on a plurality of capture objects in droplets, each comprising one or more binding members that specifically binds to the tag thereby generating a complex comprising capture object-amplification product;
(c) detectably labeling the amplification product in the complex to generate a detectably labeled complex;
(d) spatially segregating the droplets containing the capture objects into a plurality of wells such that each well contains no more than one capture object;
(e) detecting the presence of the detectably labeled complex in the plurality of wells, and wherein the combination of the tag and the binding member that specifically binds to the tag is selected from the group consisting of antibody-antigen, antibody-hapten, receptor-ligand, protein-co-factor, enzyme-co-factor, and protein-ligand;

wherein the method is performed using an integrated digital microfluidic and analyte detection device comprising an amplification module and an analyte detection module, the amplification module is configured to perform the step (a); and the analyte detection module is configured to perform the steps (b) to (e), the analyte detection module comprising:

a first substrate and a second substrate, wherein the second substrate is positioned over the first substrate and is separated from the first substrate by a gap; the first substrate comprising: a series of electrodes positioned on an upper surface of the first substrate; a proximal portion at which the droplets containing the capture objects are introduced; an array of wells comprising the plurality of wells, wherein the array of wells is positioned in only a distal portion of the first substrate; and wherein the series of electrodes extend from the proximal portion to the distal portion of the first substrate, wherein the series of electrodes manipulate the droplets containing the capture objects and droplets containing reagents for labeling and detecting the amplification products to spatially segregate in step (d) the capture objects into the plurality of wells such that each well in the plurality of wells contains no more than one capture object.

31. The method of claim 30, wherein the concentration of the amplification product is as low as 20 aM.

32. The method of claim 30, wherein the concentration of the amplification product is as low as 30 aM.

33. The method of claim 30, wherein the concentration of the amplification product is as low as 100 aM.

* * * * *

UNITED STATES PATENT AND TRADEMARK OFFICE
CERTIFICATE OF CORRECTION

PATENT NO. : 11,578,358 B2
APPLICATION NO. : 16/312489
DATED : February 14, 2023
INVENTOR(S) : Mark A. Hayden et al.

Page 1 of 2

It is certified that error appears in the above-identified patent and that said Letters Patent is hereby corrected as shown below:

In the Specification

In Column 3, Line 38, delete "comprises;" and insert -- comprises: --.

In Column 9, Line 39, delete "(FTC))," and insert -- (FTO), --.

In Column 30, Line 8, delete "SAW" and insert -- SAW; --.

In Column 32, Line 67, delete "Impermeable" and insert -- impermeable --.

In Column 33, Line 37, delete "purpose," and insert -- purpose. --.

In Column 34, Line 40, delete "the a" and insert -- the --.

In Column 34, Line 49, delete "form," and insert -- form. --.

In Column 34, Line 59, delete "mechanism," and insert -- mechanism. --.

In Column 35, Line 38, delete "etc," and insert -- etc. --.

In Column 37, Line 36, delete "13A-133" and insert -- 13A-13B --.

In Column 38, Line 14, delete "13B," and insert -- 13B. --.

In Column 49, Line 34, before "amplified" delete "of the".

In the Claims

In Column 60, Line 9, in Claim 18, delete "delectably" and insert -- detectably --.

Signed and Sealed this
Fourth Day of April, 2023

Katherine Kelly Vidal
*Director of the United States Patent and Trademark Office*

CERTIFICATE OF CORRECTION (continued)
U.S. Pat. No. 11,578,358 B2

In Column 60, Line 39, in Claim 19, delete "enzyme-co-factor" and insert -- enzyme-co-factor, --.

In Column 61, Line 24, in Claim 21, delete "delectably" and insert -- detectably --.

In Column 61, Line 30, in Claim 21, delete "enzyme-co-factor" and insert -- enzyme-co-factor, --.

In Column 62, Line 47, in Claim 26, delete "that," and insert -- that --.

In Column 63, Line 13, in Claim 27, after "26," insert -- further --.

In Column 63, Line 13, in Claim 27, after "detecting" insert -- the --.